(12) United States Patent
Baldwin et al.

(10) Patent No.: US 8,084,485 B2
(45) Date of Patent: Dec. 27, 2011

(54) 6-(AMINOALKYL)INDAZOLES

(75) Inventors: John J. Baldwin, Gwynedd Valley, PA (US); David A. Claremon, Maple Glen, PA (US); Lawrence W. Dillard, Yardley, PA (US); Alexey V. Ishchenko, Somerville, MA (US); Jing Yuan, Lansdale, PA (US); Zhenrong Xu, Horsham, PA (US); Gerard McGeehan, Garnet Valley, PA (US); Wenguang Zeng, Lawrenceville, NJ (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 88 days.

(21) Appl. No.: 12/225,756

(22) PCT Filed: Mar. 30, 2007

(86) PCT No.: PCT/US2007/008180
§ 371 (c)(1),
(2), (4) Date: Sep. 15, 2010

(87) PCT Pub. No.: WO2007/120523
PCT Pub. Date: Oct. 25, 2007

(65) Prior Publication Data
US 2010/0331287 A1    Dec. 30, 2010

Related U.S. Application Data

(60) Provisional application No. 60/788,082, filed on Mar. 31, 2006.

(51) Int. Cl.
*A61K 31/416* (2006.01)
*C07D 231/56* (2006.01)

(52) U.S. Cl. ...................................... 514/405; 548/362.5

(58) Field of Classification Search ................... 514/405; 548/362.5
See application file for complete search history.

(56) References Cited

U.S. PATENT DOCUMENTS
5,627,182 A    5/1997    Göschke et al.

FOREIGN PATENT DOCUMENTS
| WO | WO 97/09311 A1 | 3/1997 |
| WO | WO 99/23077 A1 | 5/1999 |
| WO | WO 03/050073 | 6/2003 |
| WO | WO 2005/070877 | 8/2005 |
| WO | WO 2006/083924 A1 | 8/2006 |
| WO | WO 2007/031558 A1 | 3/2007 |
| WO | WO 2007/120523 A3 | 10/2007 |
| WO | WO 2007/123718 A1 | 11/2007 |

OTHER PUBLICATIONS

Wood, J., et al., "Structure-based Design of Aliskiren, a Novel Orally Effective Renin Inhibitor," *Biochemical and Biophysical Research Communications*, 308(4): 698-705 (2003).
PCT International Search Report from PCT/US2007/007961, Dated: Sep. 28, 2007.
PCT Written Opinion of the International Searching Authority from PCT/US2007/007961, Dated: Sep. 28, 2007.
PCT International Preliminary Report on Patentability from PCT/US2007/007961, Dated: Oct. 9, 2008.
PCT International Search Report from PCT/US2006/003489, Dated: Jun. 20, 2006.
PCT Written Opinion of the International Searching Authority from PCT/US2006/003489, Dated: Jun. 20, 2006.
PCT International Preliminary Report on Patentability from PCT/US2006/003489, Dated: Aug. 16, 2007.
PCT International Preliminary Report on Patentability from PCT/US2007/008180, Dated: Oct. 9, 2008.
PCT International Search Report, Nov. 2, 2007, PCT/US2007/008180.
PCT Written Opinion of the International Searching Authority, Nov. 2, 2007, PCT/US2007/008180.
United States Patent and Trademark Office, Restriction Requirement dated Sep. 14, 2011, U.S. Appl. No. 11/883,518.
United States Patent and Trademark Office, Restriction Requirement dated Nov. 1, 2011, U.S. Appl. No. 12/225,757.
United States Patent and Trademark Office, Restriction Requirement dated Nov. 10, 2011, U.S. Appl. No. 11/883,518.

*Primary Examiner* — Rebecca Anderson
*Assistant Examiner* — Samantha Shterengarts
(74) *Attorney, Agent, or Firm* — Hamilton, Brook, Smith & Reynolds, P.C.

(57) ABSTRACT

6-(Aminoalkyl)indazoles of formula (I) and the salts thereof have renin-inhibiting properties and can be used as antihypertensive, and renal, cardiac and vascular protecting medicinally active ingredients.

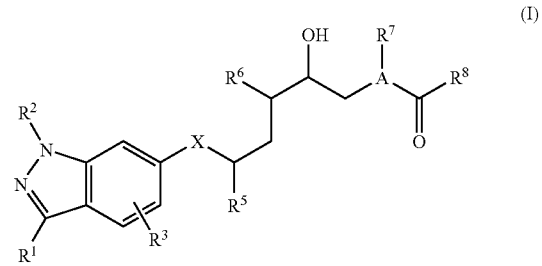

15 Claims, No Drawings

6-(AMINOALKYL)INDAZOLES

RELATED APPLICATIONS

This application is the U.S. National Stage of International Application No. PCT/US2007/008180, filed Mar. 30, 2007, published in English, and claims priority under 35 U.S.C. § 119 or 365 to U.S. Provisional Application No. 60/788,082, filed Mar. 31, 2006, the entire teachings of which are incorporated herein by reference.

BACKGROUND

In the renin-angiotensin-aldosterone system (RAAS) the biologically active peptide angiotensin II (Ang II) is generated by a two-step mechanism. The highly specific aspartic protease renin cleaves angiotensinogen to angiotensin I (Ang I), which is then further processed to Ang II by the less specific angiotensin-converting enzyme (ACE). Ang II is known to work on at least two receptor subtypes called $AT_1$ and $AT_2$. Whereas $AT_1$ seems to transmit most of the known functions of Ang II, the role of $AT_2$ is still unknown.

Modulation of the RAAS represents a major advance in the treatment of cardiovascular diseases (Zaman, M. A. et al *Nature Reviews Drug Discovery* 2002, 1, 621-636). ACE inhibitors and $AT_1$ blockers have been accepted as treatments of hypertension (Waeber B. et al., "The renin-angiotensin system: role in experimental and human hypertension", in Berkenhager W. H., Reid J. L. (eds): *Hypertension*, Amsterdam, Elsevier Science Publishing Co, 1996, 489-519; Weber M. A., *Am. J. Hypertens.*, 1992, 5, 247S). In addition, ACE inhibitors are used for renal protection (Rosenberg M. E. et al., *Kidney International*, 1994, 45, 403; Breyer J. A. et al., *Kidney International*, 1994, 45, S156), in the prevention of congestive heart failure (Vaughan D. E. et al., *Cardiovasc. Res.*, 1994, 28, 159; Fouad-Tarazi F. et al., *Am. J. Med.*, 1988, 84 (Suppl. 3A), 83) and myocardial infarction (Pfeffer M. A. et al., *N Engl. J. Med*, 1992, 327, 669).

Interest in the development of renin inhibitors stems from the specificity of renin (Kleinert H. D., *Cardiovasc. Drugs*, 1995, 9, 645). The only substrate known for renin is angiotensinogen, which can only be processed (under physiological conditions) by renin. In contrast, ACE can also cleave bradykinin besides Ang I and can be bypassed by chymase, a serine protease (Husain A., *J. Hypertens.*, 1993, 11, 1155). In patients, inhibition of ACE thus leads to bradykinin accumulation causing cough (5-20%) and potentially life-threatening angioneurotic edema (0.1-0.2%) (Israili Z. H. et al., *Annals of Internal Medicine*, 1992, 117, 234). Chymase is not inhibited by ACE inhibitors. Therefore, the formation of Ang II is still possible in patients treated with ACE inhibitors. Blockade of the ATI receptor (e.g., by losartan) on the other hand overexposes other AT-receptor subtypes to Ang II, whose concentration is dramatically increased by the blockade of AT1 receptors. In summary, renin inhibitors are not only expected to be superior to ACE inhibitors and $AT_1$ blockers with regard to safety, but more importantly also with regard to their efficacy in blocking the RAAS.

Only limited clinical experience (Azizi M. et al., *J. Hypertens.*, 1994, 12, 419; Neutel J. M. et al., *Am. Heart*, 1991, 122, 1094) has been generated with renin inhibitors because their peptidomimetic character imparts insufficient oral activity (Kleinert H. D., *Cardiovasc. Drugs*, 1995, 9, 645). The clinical development of several compounds has been stopped because of this problem together with the high cost of goods. Only one compound has entered clinical trials (Rahuel J. et al., *Chem. Biol.*, 2000, 7, 493; Mealy N. E., *Drugs of the Future*, 2001, 26, 1139). Thus, metabolically stable, orally bioavailable and sufficiently soluble renin inhibitors that can be prepared on a large scale are not available. Recently, the first non-peptide renin inhibitors were described which show high in vitro activity (Oefner C. et al., *Chem. Biol.*, 1999, 6, 127; Patent Application WO 97/09311; Maerki H. P. et al., *II Farmaco*, 2001, 56, 21). The present invention relates to the unexpected identification of renin inhibitors of a non-peptidic nature and of low molecular weight. Orally active renin inhibitors which are active in indications beyond blood pressure regulation where the tissular renin-chymase system may be activated leading to pathophysiologically altered local functions such as renal, cardiac and vascular remodeling, atherosclerosis, and restenosis, are described.

All documents cited herein are incorporated by reference.

SUMMARY OF THE INVENTION

It has now been found that 6-(aminoalkyl)indazoles of formula I

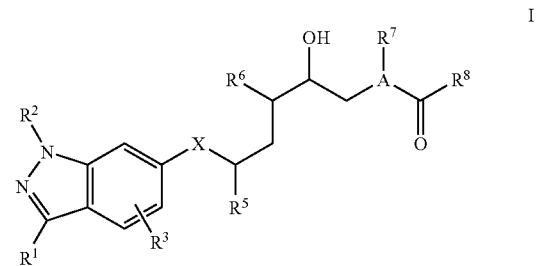

and the salts thereof have renin-inhibiting properties and can be used as antihypertensive, and renal, cardiac and vascular protecting medicinally active ingredients.

DETAILED DESCRIPTION

An embodiment of the invention is a compound of formula I

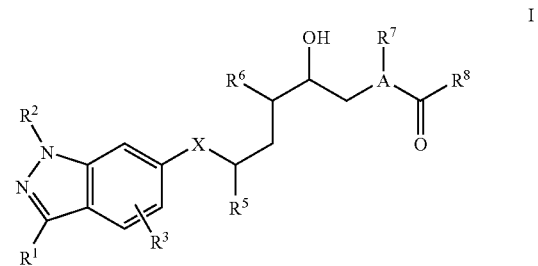

wherein $R^1$ is H, lower alkyl, cycloalkyl, lower haloalkyl, halocycloalkyl, amino, cyano, carboxy, aminocarbonyl, N-mono-lower alkyl-aminocarbonyl, N,N-di-lower alkyl-aminocarbonyl, cycloalkyl-lower alkyl, halocycloalkyl-loweralkyl, cyano-lower alkyl, hydroxy-lower alkyl, lower alkoxy-lower alkyl, lower haloalkoxy-lower alkyl, lower alkoxy-lower alkoxy-lower alkyl, lower haloalkoxy-lower alkoxy-lower alkyl, cycloalkoxy-lower alkyl, halocycloalkoxy-lower alkyl, lower alkanoylamino-lower alkyl, lower alkoxycarbonyl-amino-lower alkyl, aminocarbonylamino-lower alkyl, lower alkylaminocarbonylamino-lower alkyl, di(lower alkyl)aminocarbonylamino-lower alkyl, aminosulfonylamino-lower alkyl, lower alkylaminosulfonylamino-lower alkyl, di(lower alkyl)aminosulfonylamino-lower alkyl, lower haloalkoxy-lower alkyl, aminocarbonyl-lower alkyl, N-mono-lower alkyl-aminocarbonyl-lower alkyl, N,N-di-lower alkyl-aminocarbonyl-lower alkyl, carbamoyl-lower alkyl, or N-mono- or N,N-di-lower alkylcarbamoyl-lower alkyl;

$R^2$ is lower alkyl, lower haloalkyl, cycloalkyl, halocycloalkyl, cycloalkyl-lower alkyl, halocycloalkyl-loweralkyl, cyano-lower alkyl, hydroxy-lower alkyl, lower alkoxy-lower alkyl, lower haloalkoxy-lower alkyl, lower alkoxy-lower alkoxy-lower alkyl, lower haloalkoxy-lower alkoxy-lower alkyl, cycloalkoxy-lower alkyl, halocycloalkoxy-lower alkyl, lower alkanoylamino-lower alkyl, lower alkoxycarbonyl-amino-lower alkyl, aminocarbonylamino-lower alkyl, lower alkylaminocarbonylamino-lower alkyl, di(lower alkyl)aminocarbonylamino-lower alkyl, aminosulfonylamino-lower alkyl, lower alkylaminosulfonylamino-lower alkyl, di(lower alkyl)aminosulfonylamino-lower alkyl, lower haloalkoxy-lower alkyl, aminocarbonyl-lower alkyl, N-mono-lower alkyl-aminocarbonyl-lower alkyl, N,N-di-lower alkyl-aminocarbonyl-lower alkyl, carbamoyl-lower alkyl, or N-mono- or N,N-di-lower alkylcarbamoyl-lower alkyl;

$R^3$ is H, halogen, cyano, lower alkyl, or lower haloalkyl;

X is methylene, hydroxymethylene, or lower alkanoyloxymethylene;

$R^5$ is lower alkyl, lower haloalkyl, cycloalkyl, halocycloalkyl, lower alkyl-cycloalkyl, lower haloalkyl-cycloalkyl, cycloalkyl-lower alkyl, aryl, aryl-lower alkyl, heterocyclyl, or heterocyclyl-lower alkyl;

$R^6$ is amino or lower alkylamino;

A is N or CH;

$R^7$ is hydrogen, lower alkyl, lower haloalkyl, cycloalkyl, lower alkoxy-lower alkyl, or lower haloalkoxy-lower alkyl;

$R^8$ is 1) lower alkyl, lower haloalkyl, $C_8$-$C_{15}$alkyl, $C_8$-$C_{15}$haloalkyl, cycloalkyl, halocycloalkyl, lower alkyl-cycloalkyl, cycloalkyl-lower alkyl, halocycloalkyl-lower alkyl, lower alkoxy-loweralkyl, lower haloalkoxy-lower alkyl, cycloalkoxy-lower alkyl, cycloalkoxy-cycloalkyl, lower alkylthio-lower alkyl, lower haloalkylthio-lower alkyl, lower alkanesulfonyl-lower alkyl, lower haloalkanesulfonyl-lower alkyl, lower alkylthio-cycloalkyl, lower haloalkylthio-cycloalkyl, lower alkanesulfonyl-cycloalkyl, lower haloalkanesulfonyl-cycloalkyl, aryl, aryl-lower alkyl, aryl-lower hydroxyalkyl, arylcycloalkyl, aryloxy-lower alkyl, aryloxy cycloalkyl, arylthio-lower alkyl, arylsulfonyl-lower alkyl, arylthio-cycloalkyl, arylsulfonyl-cycloalkyl, lower alkanoyl-lower alkyl, hydroxy-lower alkyl, amino-lower alkyl, lower alkanoylamino-lower alkyl, N-mono-lower alkylamino-lower alkyl, N,N-di-lower alkylamino-lower alkyl, piperidino-lower alkyl, hydroxypiperidino-lower alkyl, lower alkoxypiperidino-lower alkyl, morpholino-lower alkyl, dimethylmorpholino-lower alkyl, thiomorpholino-lower alkyl, S,S-dioxothiomorpholino-lower alkyl, carboxy-lower alkyl, lower alkoxycarbonyl-lower alkyl, carbamoyl-lower alkyl, N-mono-lower alkylcarbamoyl-lower alkyl, N,N-di-lower alkylcarbamoyl-lower alkyl, carboxy-(hydroxy)-lower alkyl, lower alkoxycarbonyl-(hydroxy)-lower alkyl, carbamoyl-(hydroxy)-lower alkyl, N-mono-lower alkylcarbamoyl-(hydroxy)-lower alkyl, N,N-di-lower alkylcarbamoyl-(hydroxy)-lower alkyl, 5- or 6-membered carboxycycloalkyl-lower alkyl, 5- or 6-membered lower alkoxycarbonyl-cycloalkyl-lower alkyl, 5- or 6-membered carbamoylcycloalkyl-lower alkyl, 5- or 6-membered N-mono-alkylcarbamoylcycloalkyl-lower alkyl, N,N-di-lower alkylcarbamoylcycloalkyl-lower alkyl, cyano-lower alkyl, sulfamoyl-lower alkyl, lower alkylsulfamoyl-lower alkyl, di-lower alkylsulfamoyl-lower alkyl, imidazolyl-lower alkyl, oxopyrrolidinyl-lower alkyl, benzimidazolyl-lower alkyl, oxadiazolyl-lower alkyl, pyridyl-lower alkyl, oxopiperidinyl-lower alkyl, quinolinyl-lower alkyl, piperidin-4-yl-lower alkyl, or lower alkanoylpiperidin-4-yl-lower alkyl, wherein said aryl, imidazolyl, benzimidazolyl, oxadiazolyl, pyridyl, quinolinyl, aryloxy, arylthio, and arylsulfonyl groups are optionally substituted with up to four groups independently selected from halo, cyano, nitro, optionally halogenated lower alkyl, optionally halogenated lower alkoxy, optionally halogenated lower alkylthio, optionally halogenated lower alkanesulfonyl, and lower alkoxycarbonyl; or

2) $NR^9R^{10}$;

$R^9$ is 1) hydrogen, lower alkyl, lower haloalkyl, lower alkenyl, $(C_8$-$C_{15})$alkyl, $(C_8$-$C_{15})$haloalkyl, cycloalkyl, halocycloalkyl, lower alkyl-cycloalkyl, cycloalkyl-lower alkyl, halocycloalkyl-lower alkyl, lower alkoxy-loweralkyl, lower haloalkoxy-lower alkyl, cycloalkoxy-lower alkyl, cycloalkoxy-cycloalkyl, lower alkylthio-lower alkyl, lower haloalkylthio-lower alkyl, lower alkanesulfonyl-lower alkyl, lower haloalkanesulfonyl-lower alkyl, lower alkylthio-cycloalkyl, lower haloalkylthio-cycloalkyl, lower alkanesulfonyl-cycloalkyl, lower haloalkanesulfonyl-cycloalkyl, aminocarbonyl-lower alkyl, lower alkylaminocarbonyl-lower alkyl, or di(lower alkyl)-aminocarbonyl-lower alkyl, or 2) aryl, aryl-lower alkyl, aryloxy-lower alkyl, arylthio-lower alkyl, or arylsulfonyl-lower alkyl wherein the aryl groups are optionally substituted with up to four groups independently selected from halo, cyano, optionally halogenated lower alkyl, optionally halogenated lower alkoxy, optionally halogenated lower alkylthio, and optionally halogenated lower alkanesulfonyl;

$R^{10}$ is 1) hydrogen, lower alkyl, lower haloalkyl, $(C_8$-$C_{15})$alkyl, $(C_8$-$C_{15})$haloalkyl, cycloalkyl, halocycloalkyl, cycloalkyl-lower alkyl, halocycloalkyl-lower alkyl, lower alkoxy-lower alkyl, lower haloalkoxy-lower alkyl, alkylthio-lower alkyl, lower haloalkylthio-lower alkyl, lower alkanesulfonyl-lower alkyl, lower haloalkanesulfonyl-lower alkyl, or 2) aryl or aryl-lower alkyl wherein the aryl groups are optionally substituted with up to four groups independently selected from halo, cyano, optionally halogenated lower alkyl, optionally halogenated lower alkoxy, optionally halogenated lower alkylthio, and optionally halogenated lower alkanesulfonyl;

or an enantiomer, diastereomer, or salt thereof.

Another embodiment of the invention is a compound of Formula I, or an enantiomer, diastereomer, or salt thereof wherein:

$R^1$ is H, lower alkyl, cycloalkyl, lower haloalkyl, halocycloalkyl; and the remainder of the variables are as defined in the paragraphs above.

Another embodiment of the invention is a compound of Formula I wherein:

$R^1$ is H or methyl;

$R^2$ is lower alkyl, cycloalkyl-lower alkyl, cyano-lower alkyl, hydroxy-lower alkyl, lower alkoxy-lower alkyl, lower alkoxy-lower alkoxy-lower alkyl, lower haloalkoxy-lower alkoxy-lower alkyl, cycloalkoxy-lower alkyl, halocycloalkoxy-lower alkyl, lower alkanoylamino-lower alkyl, lower alkoxycarbonyl-amino-lower alkyl, aminocarbonylamino-lower alkyl, lower alkylaminocarbonylamino-lower alkyl, di(lower alkyl)aminocarbonylamino-lower alkyl, aminosulfonylamino-lower alkyl, lower alkylaminosulfonylamino-lower alkyl, di(lower alkyl)aminosulfonylamino-lower alkyl, aminocarbonyl-lower alkyl, N-mono-lower alkyl-aminocarbonyl-lower alkyl, carbamoyl-lower alkyl, or N-mono-lower alkylcarbamoyl-lower alkyl;

$R^3$ is H, fluorine, cyano, methyl, or trifluoromethyl;

X is methylene, hydroxymethylene, or acetoxymethylene;

$R^5$ is lower alkyl or cycloalkyl;

$R^6$ is amino,

A is N or CH;

$R^7$ is H, lower alkyl, or cycloalkyl;

$R^8$ is 1) $(C_3-C_{11})$alkyl, $(C_3-C_{11})$haloalkyl, $(C_3-C_7)$cycloalkyl, $(C_3-C_{11})$cycloalkylalkyl, $(C_3-C_{11})$alkoxyalkyl, aryl, aryl$(C_1-C_3)$alkyl, aryl$(C_3-C_6)$cycloalkyl, arylhydroxy$(C_1-C_3)$alkyl, aryloxy$(C_1-C_5)$alkyl, or aryloxy$(C_3-C_6)$cycloalkyl wherein aryl or aryloxy may be unsubstituted or substituted with one to three groups independently selected from halogen, cyano, $(C_1-C_3)$alkyl, halo$(C_1-C_3)$alkyl, $(C_1-C_3)$alkoxy, halo$(C_1-C_3)$alkoxy; or

2) $NR_9R_{10}$;

$R^9$ is 1) hydrogen, $(C_1-C_{10})$alkyl, $(C_3-C_7)$alkenyl, $(C_3-C_7)$cycloalkyl, $(C_3-C_6)$cycloalkyl$(C_1-C_5)$alkyl, $(C_1-C_6)$alkoxy$(C_1-C_6)$alkyl, or aminocarbonyl$(C_1-C_5)$alkyl, or 2) aryl or aryl$(C_1-C_4)$alkyl wherein the aryl moiety is optionally substituted with up to 4 groups independently selected from fluorine, chlorine, cyano, $(C_1-C_3)$alkyl, halo$(C_1-C_3)$alkyl, $(C_1-C_3)$alkoxy, halo$(C_1-C_3)$alkoxy, and $(C_1-C_3)$alkanesulfonyl;

$R^{10}$ is hydrogen, lower alkyl, or lower haloalkyl; and or an enantiomer, diastereomer, or salt thereof.

A third embodiment of the invention is a compound of Formula I wherein:

$R^1=R^3=R^7=H$;

$R^2$ is lower alkyl, cycloalkyl-lower alkyl, hydroxy-lower alkyl, lower alkoxy-lower alkyl, cycloalkoxy-lower alkyl, lower alkanoylamino-lower alkyl, lower alkoxycarbonylamino-lower alkyl, aminocarbonyl-lower alkyl, or N-mono-lower alkyl-aminocarbonyl-lower alkyl;

X is methylene or hydroxymethylene;

$R^5$ is isopropyl;

$R^6$ is amino,

A is N;

$R^8$ is $(C_1-C_{10})$alkyl, $(C_3-C_7)$cycloalkyl, $(C_3-C_6)$cycloalkyl$(C_1-C_5)$alkyl, $(C_1-C_6)$alkoxy$(C_1-C_6)$alkyl, aminocarbonyl$(C_1-C_5)$alkyl, or phenyl$(C_1-C_4)$alkyl;

or an enantiomer, diastereomer, or salt thereof.

A fourth embodiment of the invention is a compound of Formula I wherein:

$R^1=R^3=R^{10}=H$;

$R^2$ is lower alkyl, cycloalkyl-lower alkyl, hydroxy-lower alkyl, lower alkoxy-lower alkyl, cycloalkoxy-lower alkyl, lower alkanoylamino-lower alkyl, lower alkoxycarbonylamino-lower alkyl, aminocarbonyl-lower alkyl, or N-mono-lower alkyl-aminocarbonyl-lower alkyl;

X is methylene or hydroxymethylene;

$R^5$ is isopropyl;

$R^6$ is amino,

A is CH;

$R^7$ is isopropyl;

$R^8$ is $NR^9R^{10}$;

$R^9$ is $(C_1-C_{10})$alkyl, $(C_3-C_7)$cycloalkyl, $(C_3-C_6)$cycloalkyl$(C_1-C_5)$alkyl, $(C_1-C_6)$alkoxy$(C_1-C_6)$alkyl, aminocarbonyl$(C_1-C_5)$alkyl, or phenyl$(C_1-C_4)$alkyl;

or an enantiomer, diastereomer, or salt thereof.

A fifth embodiment of the invention is a compound of Formula I wherein:

$R^1=R^3=R^7=H$;

$R^2$ is cyclopropylethyl, 3-methoxypropyl, 3-ethoxypropyl, or 3-isopropoxypropyl;

X is methylene or hydroxymethylene;

$R^5$ is isopropyl;

$R^6$ is amino;

A is N;

$R^8$ is 2-methyl-2-hexyl;

or an enantiomer, diastereomer, or salt thereof.

A sixth embodiment of the invention is a compound of Formula I wherein:

$R^1=R^3=R^{10}=H$;

$R^2$ is cyclopropylethyl, 3-methoxypropyl, 3-ethoxypropyl, or 3-isopropoxypropyl;

X is methylene or hydroxymethylene;

$R^5$ is isopropyl;

$R^6$ is amino;

A is CH;

$R^7$ is isopropyl;

$R^8$ is $NR^9R^{10}$;

$R^9$ is $-CH_2C(Me)_2CONH_2$;

or an enantiomer, diastereomer, or salt thereof.

Especially effective are those compounds of formula I wherein at least one, two, or preferably all three of the asymmetric carbon atoms of the main chain have the stereochemical configuration shown in formula Ia

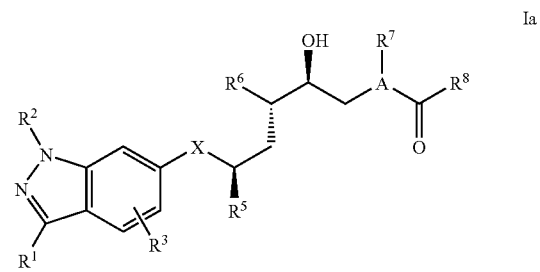

Ia or a pharmaceutically acceptable salt thereof.

The following are compounds of the invention:

I-1 N-(3-amino-2-hydroxy-5-((1-(3-methoxypropyl)-1H-indazol-6-yl)methyl)-6-methylheptyl)-2,2-dimethylhexanamide I-2 N-(3-amino-5-((1-(2-cyclopropylethyl)-1H-indazol-6-yl)(hydroxy)methyl)-2-hydroxy-6-methylheptyl)-2,2-dimethylhexanamide I-3 N-(3-amino-2-hydroxy-5-(hydroxy(1-(3-methoxypropyl)-1H-indazol-6-yl)methyl)-6-methylheptyl)-2,2-dimethylhexanamide I-4 N-(3-amino-5-((1-(3-ethoxypropyl)-1H-indazol-6-yl)(hydroxy)methyl)-2-hydroxy-6-methylheptyl)-2,2-dimethylhexanamide I-5 N-(3-amino-2-hydroxy-5-(hydroxy(1-(3-isopropoxypropyl)-1H-indazol-6-yl)methyl)-6-methylheptyl)-2,2-dimethylhexanamide I-6 5-amino-N-(3-amino-2,2-dimethyl-3-oxopropyl)-4-hydroxy-2-isopropyl-7-((1-(3-methoxypropyl)-1H-indazol-6-yl)methyl)-8-methylnonanamide I-7 4-amino-6-(2,2-dimethylhexanamido)-5-hydroxy-2-isopropyl-1-(1-(3-methoxypropyl)-1H-indazol-6-yl)hexyl acetate or an enantiomer, diastereomer, or salt thereof.

The following are preferred compounds of the invention:

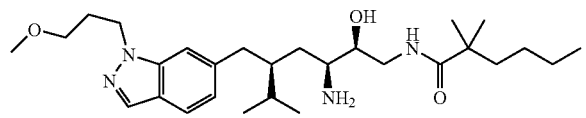

I-1a

N-((2S,3S,5S)-3-amino-2-hydroxy-
5-((1-(3-methoxypropyl)-1H-indazol-
6-yl)methyl)-6-methylheptyl)-2,2-
dimethylhexanamide

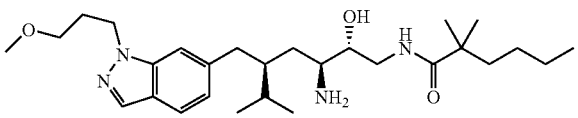

I-1b

N-((2R,3S,5S)-3-amino-2-hydroxy-
5-((1-(3-methoxypropyl)-1H-indazol-
6-yl)methyl)-6-methylheptyl)-2,2-
dimethylhexanamide

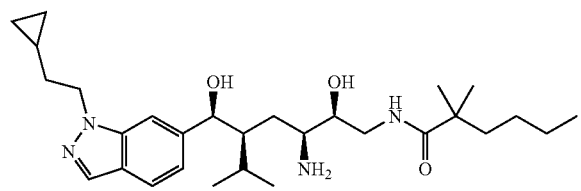

I-2a

N-((2S,3S,5S)-3-amino-5-((S)-(1-(2-
cyclopropylethyl)-1H-indazol-6-
yl)(hydroxy)methyl)-2-hydroxy-6-
methylheptyl)-2,2-
dimethylhexanamide

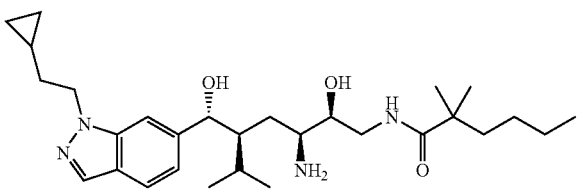

I-2b

N-((2S,3S,5S)-3-amino-5-((R)-(1-(2-
cyclopropylethyl)-1H-indazol-6-
yl)(hydroxy)methyl)-2-hydroxy-6-
methylheptyl)-2,2-
dimethylhexanamide

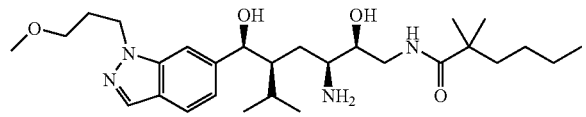

I-3a

N-((2S,3S,5S)-3-amino-2-hydroxy-
5-((S)-hydroxy(1-(3-methoxypropyl)-
1H-indazol-6-yl)methyl)-6-
methylheptyl)-2,2-
dimethylhexanamide

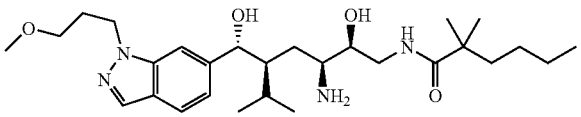

I-3b

N-((2S,3S,5S)-3-amino-2-hydroxy-
5-((R)-hydroxy(1-(3-
methoxypropyl)-1H-indazol-6-
yl)methyl)-6-methylheptyl)-2,2-
dimethylhexanamide

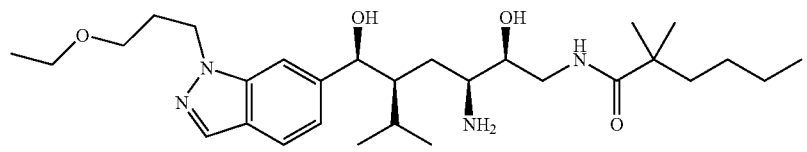

I-4a

N-((2S,3S,5S)-3-amino-5-((S)-(1-(3-
ethoxypropyl-1H-indazol-6-
yl)(hydroxy)methyl)-2-hydroxy-6-
methylheptyl)-2,2-
dimethylhexanamide

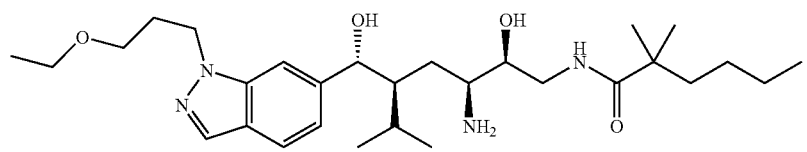

I-4b

N-((2S,3S,5S)-3-amino-5-((R)-(1-(3-
ethoxypropyl-1H-indazol-6-
yl)(hydroxy)methyl)-2-hydroxy-6-
methylheptyl)-2,2-
dimethylhexanamide -continued

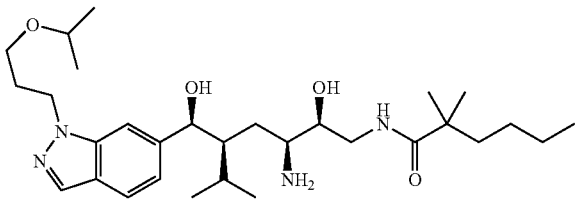

I-5a

N-((2S,3S,5S)-3-amino-2-hydroxy-5-((S)-hydroxy(1-(3-isopropoxypropyl)-1H-indazol-6-yl)methyl)-6-methylheptyl)-2,2-dimethylhexanamide

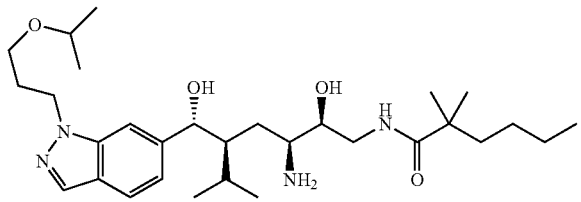

I-5b

N-((2S,3S,5S)-3-amino-2-hydroxy-5-((R)-hydroxy(1-(3-isopropoxypropyl)-1H-indazol-6-yl)methyl)-6-methylheptyl)-2,2-dimethylhexanamide

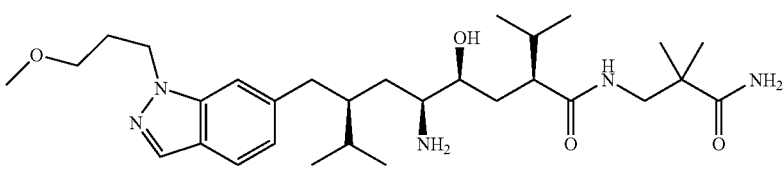

I-6a (2S,4S,5S,7S)-5-amino-N-(3-amino-2,2-dimethyl-3-oxopropyl)-4-hydroxy-2-isopropyl-7-((1-(3-methoxypropyl)-1H-indazol-6-yl)methyl)-8-methylnonanamide

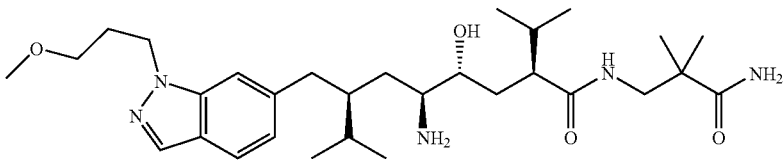

I-6b (2S,4R,5S,7S)-5-amino-N-(3-amino-2,2-dimethyl-3-oxopropyl)-4-hydroxy-2-isopropyl-7-((1-(3-methoxypropyl)-1H-indazol-6-yl)methyl)-8-methylnonanamide

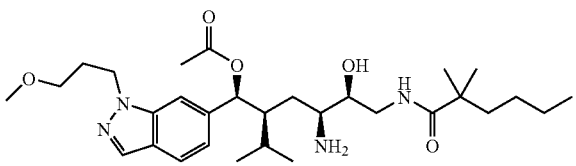

I-7a (1S,2S,4S,5S)-4-amino-6-(2,2-dimethylhexanamido)-5-hydroxy-2-isopropyl-1-(1-(3-methoxypropyl)-1H-indazol-6-yl)hexyl acetate

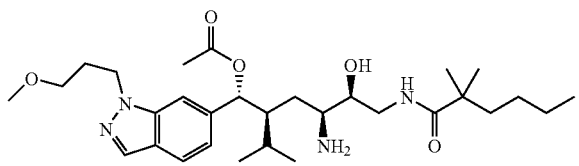

I-7b (1R,2S,4S,5S)-4-amino-6-(2,2-dimethylhexanamido)-5-hydroxy-2-isopropyl-1-(1-(3-methoxypropyl)-1H-indazol-6-yl)hexyl acetate Pharmaceutically acceptable salts of the compounds shown immediately above are also included.

The following are more preferred compounds of the invention: I-2a, I-3a and I-6a.

The following terms are used herein.

Aryl and aryl in aryloxy, arylthio, arylsulfonyl, aryl-lower alkoxy, aryl-lower alkyl and the like are, for example, phenyl or naphthyl that is unsubstituted or mono-, di- or tri-substituted by optionally halogenated lower alkyl, optionally halogenated lower alkoxy, hydroxy, amino, lower alkylamino, di-lower alkylamino, halogen, cyano, carbamoyl, lower alkoxycarbonyl, trifluoromethoxy, and/or by trifluoromethyl.

Cycloalkoxy and cycloalkoxy in cycloalkoxy-lower alkoxy is, for example, 3- to 8-membered, preferably 3-, 5- or 6-membered, cycloalkoxy, such as cyclopropyloxy, cyclopentyloxy, cyclohexyloxy, also cyclobutyloxy, cycloheptyloxy, or cyclooctyloxy.

Cycloalkyl is, for example, 3- to 8-membered, preferably 3-, 5- or 6-membered cycloalkyl, such as cyclopropyl, cyclopentyl, cyclohexyl, also cyclobutyl, cycloheptyl, or cyclooctyl.

Heterocyclyl is, for example, a 3- to 8-membered, preferably a 5- or 6-membered, saturated heterocycle, for example tetrahydrofuryl, tetrahydrothienyl, pyrrolidinyl, tetrahydropyranyl, tetrahydrothiopyranyl, and piperidinyl.

Free or esterified or amidated carboxy-lower alkoxy is, for example, carboxy-lower alkoxy, lower alkoxycarbonyl-lower alkoxy, carbamoyl-lower alkoxy, or N-mono- or N,N-di-lower alkylcarbamoyl-lower alkoxy.

Optionally lower alkanoylated, halogenated or sulfonylated hydroxy-lower alkoxy is, for example, lower alkanoyloxy-lower alkyl, hydroxy-lower alkoxy, halo-(hydroxy)-lower alkoxy, or lower alkanesulfonyl-(hydroxy)-lower alkoxy.

Optionally hydrogenated heteroaryl-lower alkoxy is, for example, optionally partially hydrogenated or N-oxidized pyridyl-lower alkoxy, thiazolyl-lower alkoxy, thiazolinyl-lower alkoxy or especially morpholino-lower alkoxy.

Optionally hydrogenated heteroarylthio-lower alkoxy is, for example, optionally partially or fully hydrogenated heteroarylthio-lower alkoxy, such as thiazolylthio-lower alkoxy, thiazolinylthio-lower alkoxy, imidazolylthio-lower alkoxy, imidazolinylthio-lower alkoxy optionally N-oxidized pyridylthio-lower alkoxy, or pyrimidinylthio-lower alkoxy.

Free or esterified or amidated carboxy-lower alkyl is, for example, carboxy-lower alkyl, lower alkoxycarbonyl-lower alkyl, carbamoyl-lower alkyl, or N-mono- or N,N-di-lower alkylcarbamoyl-lower alkyl.

Optionally halogenated lower alkyl is, for example, lower alkyl, monohalo-lower alkyl or polyhalo-lower alkyl.

Optionally halogenated lower alkoxy is, for example, lower alkoxy, monohalo-lower alkoxy or polyhalo-lower alkoxy.

Optionally S-oxidized lower alkylthio-lower alkyl is, for example, lower alkylthio-lower alkyl, lower alkanesulfinyl-lower alkyl, or lower alkanesulfonyl-lower alkyl.

Optionally S-oxidized lower alkylthio-lower alkoxy is, for example, lower alkylthio-lower alkoxy, lower alkanesulfinyl-lower alkoxy or lower alkanesulfonyl-lower alkoxy.

Optionally hydrogenated heteroaryl-lower alkyl or optionally N-oxidized heteroaryl-lower alkyl is, for example, optionally partially hydrogenated or N-oxidized pyridyl-lower alkyl.

Optionally hydrogenated heteroarylthio-lower alkyl or optionally N-oxidized heteroarylthio-lower alkyl is, for example, thiazolylthio-lower alkyl or thiazolinylthio-lower alkyl, imidazolylthio-lower alkyl, optionally N-oxidized pyridylthio-lower alkyl, or pyrimidinylthio-lower alkyl.

Amino-lower alkyl that is unsubstituted or N-mono- or N,N-di-lower alkylated, N-lower alkanoylated or N-lower alkanesulfonylated or N,N-disubstituted by lower alkylene, by unsubstituted or N'-lower alkylated or N'-lower alkanoylated aza-lower alkylene, by oxa-lower alkylene or by optionally S-oxidized thia-lower alkylene is, for example, amino-lower alkyl, lower alkylamino-lower alkyl, di-lower alkylamino-lower alkyl, lower alkanoylamino-lower alkyl, lower alkanesulfonylamino-lower alkyl, polyhalo-lower alkanesulfonylamino-lower alkyl, pyrrolidine-lower alkyl, piperidino-lower alkyl, piperazino-, N'-lower alkylpiperazino- or N'-lower alkanoylpiperazino-lower alkyl, morpholino-lower alkyl, thiomorpholino-, S-oxothiomorpholino-, or S,S-dioxothiomorpholino-lower alkyl.

Amino-lower alkoxy that is unsubstituted or N-mono- or N,N-di-lower alkylated, N-lower alkanoylated or N-lower alkanesulfonylated or N,N-disubstituted by lower alkylene, by unsubstituted or N'-lower alkylated amino-lower alkylene or lower alkanoylated-amino-lower alkylene, by oxa-lower alkylene or by optionally S-oxidized thia-lower alkylene is, for example, amino-lower alkoxy, lower alkylamino-lower alkoxy, di-lower alkylamino-lower alkoxy, lower alkanoylamino-lower alkoxy, lower alkanesulfonylamino-lower alkoxy, polyhalo-lower alkanesulfonylamino-lower alkoxy, pyrrolidino-lower alkoxy, piperidino-lower alkoxy, piperazino-, N'-lower alkylpiperazino- or N'-lower alkanoylpiperazino-lower alkoxy, morpholino-lower alkoxy, thiomorpholino-, S-oxothiomorpholino-, or S,S-dioxothiomorpholino-lower alkoxy.

Unsubstituted or N-mono- or N,N-di-lower alkylated or N-lower alkanoylated amino is, for example, amino, lower alkylamino, di-lower alkylamino, or lower alkanoylamino.

Free or aliphatically esterified or etherified hydroxy-lower alkyl is, for example, hydroxy-lower alkyl, lower alkanoyloxy-lower alkyl, lower alkoxy-lower alkyl, or lower alkenyloxy-lower alkyl.

Amino-lower alkyl that is unsubstituted or N-lower alkanoylated, N-mono- or N,N-di-lower alkylated or N,N-disubstituted by lower alkylene, by hydroxy-, lower alkoxy- or lower alkanoyloxy-lower alkylene, by unsubstituted or lower alkanoylated-amino-lower alkylene, by oxa-lower alkylene or by optionally S-oxidized thia-lower alkylene is, for example, amino-lower alkyl, lower alkanoylamino-lower alkyl, N-mono- or N,N-di-lower alkylamino-lower alkyl, optionally hydroxylated or lower alkoxylated piperidino-lower alkyl, such as piperidino-lower alkyl, hydroxypiperidino-lower alkyl or lower alkoxy-piperidino-lower alkyl, piperazino-, ω-lower alkylpiperazino- or N'-lower alkanoyl-piperazino-lower alkyl, unsubstituted or lower alkylated morpholino-lower alkyl, such as morpholino-lower alkyl or dimethylmorpholino-lower alkyl, or optionally S-oxidized thio-morpholino-lower alkyl, such as thiomorpholino-lower alkyl or S,S-dioxothiomorpholino-lower alkyl.

Free or esterified or amidated carboxy-(hydroxy)-lower alkyl is, for example, carboxy-(hydroxy)-lower alkyl, lower alkoxycarbonyl-(hydroxy)-lower alkyl or carbamoyl-(hydroxy)-lower alkyl.

Free or esterified or amidated carboxycycloalkyl-lower alkyl is, for example, 5- or 6-membered carboxycycloalkyl-lower alkyl, lower alkoxycarbonylcycloalkyl-lower alkyl, carbamoylcycloalkyl-lower alkyl, or N-mono- or N,N-di-lower alkylcarbamoylcyclo-alkyl-lower alkyl.

Unsubstituted or N-mono- or N,N-di-lower alkylated sulfamoyl-lower alkyl is, for example, sulfamoyl-lower alkyl, lower alkylsulfamoyl-lower alkyl, or di-lower alkyl-sulfamoyl-lower alkyl.

Lower radicals and compounds are, for example, those having up to and including 7, preferably up to and including 4, carbon atoms.

5- or 6-Membered carboxycycloalkyl-lower alkyl, lower alkoxycarbonylcycloalkyl-lower alkyl, carbamoylcycloalkyl-lower alkyl, N-mono- or N,N-di-lower alkylcarbamoylcyclo-alkyl-lower alkyl is, for example, ω-(1-carboxycycloalkyl)-$C_1$-$C_4$ alkyl, ω-(1-lower alkoxycarbonylcycloalkyl)-$C_1$-$C_4$ alkyl, ω-(1-carbamoylcycloalkyl)-$C_1$-$C_4$ alkyl, ω-(1-lower alkylcarbamoylcycloalkyl)-$C_1$-$C_4$ alkyl, or ω-(1-di-lower alkylcarbamoylcycloalkyl)-$C_1$-$C_4$ alkyl, wherein cycloalkyl is, for example, cyclopentyl or cyclohexyl; lower alkoxycarbonyl is, for example, $C_1$-$C_4$ alkoxycarbonyl, such as methoxy- or ethoxycarbonyl; lower alkylcarbamoyl is, for example, $C_1$-$C_4$ alkylcarbamoyl, such as methylcarbamoyl; di-lower alkylcarbamoyl is, for example, di-$C_1$-$C_4$ alkylcarbamoyl, such as dimethylcarbamoyl; and lower alkyl is, for example, $C_1$-$C_4$ alkyl, such as methyl, ethyl, propyl, or butyl, especially (1-carboxycyclopentyl)methyl.

5- or 6-Membered cycloalkoxy-lower alkoxy is, for example, cyclopentyloxy-($C_1$-$C_4$)alkoxy or cyclohexyloxy-($C_1$-$C_4$)alkoxy, such as cyclopentyloxy-methoxy, cyclohexyloxy-methoxy, 2-cyclopentyloxy-ethoxy, 2-cyclohexyloxy-ethoxy, 2- or 3-cyclopentyloxy-propyloxy, 2- or 3-cyclohexyloxy-propyloxy, 4-cyclopentyloxy-butyloxy or 4-cyclohexyloxy-butyloxy, especially cyclopentyloxy-methoxy or cyclohexyloxy-methoxy.

5- or 6-Membered cycloalkoxy-lower alkyl is, for example, cyclopentyloxy-($C_1$-$C_4$)alkyl or cyclohexyloxy-($C_1$-$C_4$)alkyl, such as cyclopentyloxy-methyl, cyclohexyloxy-methyl, 2-cyclopentyloxy-ethyl, 2-cyclohexyloxy-ethyl, 2- or 3-cyclopentyloxy-propyl, 2- or 3-cyclohexyloxypropyl, 2-cyclopentyloxy-2-methyl-propyl, 2-cyclohexyloxy-2-methyl-propyl, 2-cyclopentyloxy-2-ethyl-butyl, 2-cyclohexyloxy-2-ethyl-butyl, 4-cyclopentyloxy-butyl or 4-cyclohexyloxy-butyl, especially cyclopentyloxy-methyl or cyclohexyloxy-methyl.

Amino-lower alkoxy is, for example, amino-$C_1$-$C_4$ alkoxy, such as 2-aminoethoxy or 5-aminopentyloxy, also 3-aminopropyloxy or 4-aminobutyloxy.

Amino-lower alkyl is, for example, amino-$C_1$-$C_4$alkyl, such as 2-aminoethyl, 3-aminopropyl or 4-aminobutyl.

Carbamoyl-(hydroxy)-lower alkyl is, for example, carbamoyl-$C_1$-$C_7$ (hydroxy)alkyl, such as 1-carbamoyl-2-hydroxyethyl.

Carbamoyl-lower alkoxy is, for example, carbamoyl-$C_1$-$C_4$ alkoxy, such as carbamoylmethoxy, 2-carbamoylethoxy, 3-carbamoylpropyloxy, or 4-carbamoylbutyloxy, especially carbamoylmethoxy.

Carbamoyl-lower alkyl is, for example, carbamoyl-$C_1$-$C_7$ alkyl, such as carbamoylmethyl, 2-carbamoylethyl, 3-carbamoylpropyl, 2-(3-carbamoyl)propyl, 2-carbamoylpropyl, 3-(1-carbamoyl)propyl, 2-(2-carbamoyl)propyl, 2-(carbamoyl-2-methyl)propyl, 4-carbamoylbutyl, 1-carbamoylbutyl, 1-(1-carbamoyl-2-methyl)butyl, or 3-(4-carbamoyl-2-methyl)butyl.

Carboxy-(hydroxy)-lower alkyl is, for example, carboxy-$C_1$-$C_7$ (hydroxy)alkyl, such as 1-carboxy-2-hydroxy-ethyl.

Carboxy-lower alkoxy is, for example, carboxy-$C_1$-$C_4$ alkoxy, such as carboxymethoxy, 2-carboxyethoxy, 2- or 3-carboxypropyloxy, or 4-carboxybutyloxy, especially carboxy-methoxy.

Carboxy-lower alkyl is, for example, carboxy-$C_1$-$C_4$ alkyl, such as carboxymethyl, 2-carboxyethyl, 2- or 3-carboxypropyl, 2-carboxy-2-methyl-propyl, 2-carboxy-2-ethyl-butyl, or 4-carboxybutyl, especially carboxymethyl.

Cyano-lower alkoxy is, for example, cyano-$C_1$-$C_4$ alkoxy, such as cyanomethoxy, 2-cyano-ethoxy, 2- or 3-cyanopropyloxy, or 4-cyanobutyloxy, especially cyanomethoxy.

Cyano-lower alkyl is, for example, cyano-$C_1$-$C_4$ alkyl, such as cyanomethyl, 2-cyanoethyl, 2- or 3-cyanopropyl, 2-cyano-2-methyl-propyl, 2-cyano-2-ethyl-butyl, or 4-cyanobutyl, especially cyanomethyl.

Di-(N-mono- or N,N-di-lower alkylcarbamoyl)-lower alkyl is, for example, di-(N-mono- or N,N-di-$C_1$-$C_4$ alkylcarbamoyl)-$C_1$-$C_4$ alkyl, such as 1,2-di-(N-mono- or N,N-di-$C_1$-$C_4$ alkylcarbamoyl)ethyl, or 1,3-di-(N-mono- or N,N-di-$C_1$-$C_4$ alkylcarbamoyl)propyl.

Dicarbamoyl-lower alkyl is, for example, dicarbamoyl-$C_1$-$C_4$ alkyl, such as 1,2-dicarbamoylethyl or 1,3-dicarbamoylpropyl.

Dimethylmorpholino-lower alkoxy can be N-oxidized and is, for example, 2,6-dimethylmorpholino- or 3,5-dimethylmorpholino-$C_1$-$C_4$ alkoxy, such as 2,6-dimethylmorpholino- or 3,5-dimethylmorpholino-methoxy, 2-(2,6-dimethylmorpholino- or 3,5-dimethylmorpholino)-ethoxy, 3-(2,6-dimethylmorpholino- or 3,5-dimethylmorpholino)-propyloxy, 2-(2,6-dimethylmorpholino- or 3,5-dimethylmorpholino-3-methyl)propyloxy, or 1- or 2-[4-(2,6-dimethylmorpholino- or 3,5-dimethylmorpholino)]-butyloxy.

Dimethylmorpholino-lower alkyl can be N-oxidized and is, for example, 2,6-dimethylmorpholino- or 3,5-dimethylmorpholino-$C_1$-$C_4$ alkyl, such as 2,6-dimethylmorpholino- or 3,5-dimethylmorpholino-methoxy, 2-(2,6-dimethylmorpholino- or 3,5-dimethylmorpholino)-ethoxy, 3-(2,6-dimethylmorpholino- or 3,5-dimethylmorpholino)-propyl, 2-(2,6-dimethylmorpholino- or 3,5-dimethylmorpholino-3-methyl)-propyl, or 1- or 2-[4-(2,6-dimethylmorpholino- or 3,5-dimethylmorpholino)]-butyl.

Di-lower alkylamino is, for example, di-$C_1$-$C_4$ alkylamino, such as dimethylamino, N-methyl-N-ethylamino, diethylamino, N-methyl-N-propylamino, or N-butyl-N-methylamino.

Di-lower alkylamino-lower alkoxy is, for example, N,N-di-$C_1$-$C_4$ alkylamino-$C_1$-$C_4$ alkoxy, such as 2-dimethylaminoethoxy, 3-dimethylaminopropyloxy, 4-dimethylaminobutyloxy, 2-diethylaminoethoxy, 2-(N-methyl-N-ethyl-amino)ethoxy, or 2-(N-butyl-N-methyl-amino)ethoxy.

Di-lower alkylamino-lower alkyl is, for example, N,N-di-$C_1$-$C_4$ alkylamino-$C_1$-$C_4$ alkyl, such as 2-dimethylaminoethyl, 3-dimethylaminopropyl, 4-dimethylaminobutyl, 2-diethylaminoethyl, 2-(N-methyl-N-ethyl-amino)ethyl, or 2-(N-butyl-N-methyl-amino)ethyl.

Di-lower alkylcarbamoyl-lower alkoxy is, for example, N,N-di-$C_1$-$C_4$ alkylcarbamoyl-$C_1$-$C_4$ alkoxy, such as methyl- or dimethyl-carbamoyl-$C_1$-$C_4$ alkoxy, such as N-methyl-, N-butyl- or N,N-dimethyl-carbamoylmethoxy, 2-(N-methylcarbamoyl)ethoxy, 2-(N-butylcarbamoyl)ethoxy, 2-(N,N-dimethylcarbamoyl)ethoxy, 3-(N-methylcarbamoyl)propyloxy, 3-(N-butylcarbamoyl)propyloxy, 3-(N,N-dimethylcarbamoyl)propyloxy or 4-(N-methylcarbamoyl)butyloxy, 4-(N-butylcarbamoyl)-butyloxy, or 4-(N,N-dimethylcarbomoyl)butyloxy, especially N-methyl-, N-butyl- or N,N-dimethyl-carbamoylmethoxy.

Di-lower alkylcarbamoyl-lower alkyl is, for example, N,N-di-$C_1$-$C_4$ alkylcarbamoyl-$C_1$-$C_4$ alkyl, such as 2-dimethylcarbamoylethyl, 3-dimethylcarbamoylpropyl, 2-dimethylcarbamoylpropyl, 2-(dimethylcarbamoyl-2-methyl)propyl, or 2-(1-dimethylcarbamoyl-3-methyl)butyl.

Di-lower alkylsulfamoyl-lower alkyl is, for example, N,N-di-$C_1$-$C_4$ alkylsulfamoyl-$C_1$-$C_4$ alkyl, N,N-dimethylsulfamoyl-$C_1$-$C_4$ alkyl, such as N,N-dimethylsulfamoylmethyl, 2-(N,N-dimethylcarbamoyl)ethyl, 3-(N,N-dimethylcarbamoyl)propyl, or 4-(N,N-dimethylcarbamoyl)butyl, especially N,N-dimethylcarbamoylmethyl.

Unsubstituted or N-lower alkanoylated piperidyl-lower alkyl is, for example, 1-$C_1$-$C_7$-lower alkanoylpiperidin-4-yl-$C_1$-$C_4$ alkyl, such as 1-acetylpiperidinylmethyl or 2-(1-acetyl-piperidinyl)ethyl.

Optionally partially hydrogenated pyridyl-lower alkoxy or N-oxidized pyridyl-lower alkoxy is, for example, optionally partially hydrogenated pyridyl-$C_1$-$C_4$ alkoxy or N-oxopyridyl-$C_1$-$C_4$ alkoxy, such as pyridyl-methoxy, dihydropyridyl-methoxy or N-oxopyridyl-methoxy, 2-(pyridyl)ethoxy, 2-(pyridyl)propyloxy, 3-(pyridyl)propyloxy, or 4-(pyridyl)butyloxy, especially (3-pyridyl)methoxy or (4-pyridyl)methoxy.

Optionally partially hydrogenated pyridyl-lower alkyl or N-oxidized pyridyl-lower alkyl is, for example, optionally partially hydrogenated pyridyl-$C_1$-$C_4$ alkyl or N-oxopyridyl-$C_1$-$C_4$ alkyl, such as pyridyl-methyl, dihydropyridyl-methyl, N-oxopyridyl-methyl, 2-(pyridyl)ethyl, 2-(pyridyl)propyl, 3-(pyridyl)propyl, or 4-(pyridyl)butyl, especially (3-pyridyl)methyl or (4-pyridyl)methyl.

Halo-(hydroxy)-lower alkoxy is, for example, halo-$C_1$-$C_7$ (hydroxy)alkoxy, especially halo-$C_2$-$C_4$ (hydroxy)alkoxy, such as 3-halo-, such as 3-chloro-2-hydroxy-propyloxy.

Hydroxy-lower alkoxy is, for example, hydroxy-$C_2$-$C_7$ alkoxy, especially hydroxy-$C_2$-$C_4$ alkoxy, such as 2-hydroxybutyloxy, 3-hydroxypropyloxy or 4-hydroxybutyloxy.

Hydroxy-lower alkyl is, for example, hydroxy-$C_2$-$C_7$ alkyl, especially hydroxy-$C_2$-$C_4$ alkyl, such as 2-hydroxyethyl, 3-hydroxypropyl or 4-hydroxybutyl.

Hydroxypiperidino-lower alkyl is, for example, 3- or 4-hydroxypiperidino-$C_1$-$C_4$ alkyl, such as 3-hydroxypiperidinomethyl, 4-hydroxypiperidinomethyl, 2-(3-hydroxypiperidino)ethyl, 2-(4-hydroxypiperidino)ethyl, 3-(3-hydroxypiperidino)propyl, 3-(4-hydroxypiperidino)propyl, 4-(3-hydroxypiperidino)butyl or 4-(4-hydroxypiperidino)butyl.

Imidazolyl-lower alkyl is, for example, imidazolyl-$C_1$-$C_4$ alkyl, such as imidazol-4-yl-methyl, 2-(imidazol-4-yl)ethyl, 3-(imidazol-4-yl)propyl, or 4-(imidazol-4-yl)butyl.

Imidazolyl-lower alkoxy is, for example, imidazolyl-$C_1$-$C_4$ alkoxy, such as imidazol-4-yl-methoxy, 2-(imidazol-4-yl)ethoxy, 3-(imidazol-4-yl)propyloxy, or 4-(imidazol-4-yl)butyloxy.

Morpholinocarbonyl-lower alkyl is, for example, morpholinocarbonyl-$C_1$-$C_4$ alkyl, such as 1-morpholinocarbonylethyl, 3-morpholinocarbonylpropyl, or 1-(morpholinocarbonyl-2-methyl)propyl.

Morpholino-lower alkyl can be N-oxidized and is, for example, N-oxomorpholino-$C_1$-$C_4$ alkyl, such as N-oxomorpholinomethyl, 2-(N-oxomorpholino)ethyl, 3-(N-oxomorpholino)propyl, or 4-(N-oxomorpholino)butyl.

Morpholino-lower alkoxy is, for example, morpholino-$C_1$-$C_4$ alkoxy, such as 1-morpholinoethoxy, 3-morpholinopropyloxy, or 1-(morpholino-2-methyl)propyloxy.

Morpholino-lower alkoxy can be N-oxidized and is, for example, N-oxomorpholino-$C_1$-$C_4$ alkoxy, such as N-oxomorpholinomethoxy, 2-(N-oxomorpholino)ethoxy, 3-(N-oxomorpholino)propyloxy, or 4-(N-oxomorpholino)butyloxy.

Lower alkanoyl is, for example, $C_1$-$C_7$ alkanoyl, especially $C_2$-$C_6$ alkanoyl, such as acetyl, propionyl, butyryl, isobutyryl or pivaloyl.

Lower alkanoylamino is, for example, N—$C_1$-$C_7$alkanoylamino, such as acetylamino or pivaloylamino.

Lower alkanoylamino-lower alkyl is, for example, N—$C_1$-$C_4$ alkanoylamino-$C_1$-$C_4$ alkyl, such as 2-acetylaminoethyl.

Lower alkanoyl-lower alkoxy (oxo-lower alkoxy) carries the lower alkanoyl group in a position higher than the α-position and is, for example, $C_1$-$C_7$ alkanoyl-$C_1$-$C_4$ alkoxy, such as 4-acetoxy-butoxy.

Lower alkanoyloxy-lower alkyl carries the lower alkanoyloxy group in a position higher than the α-position and is, for example, $C_1$-$C_7$ alkanoyloxy-$C_1$-$C_4$ alkyl, such as 4-acetoxybutyl.

Lower alkanesulfonyl-(hydroxy)-lower alkoxy is, for example, $C_1$-$C_7$ alkanesulfonyl-$C_1$-$C_4$ (hydroxy)alkoxy, such as 3-methanesulfonyl-2-hydroxy-propyloxy.

Lower alkanesulfonyl-lower alkoxy is, for example, $C_1$-$C_7$ alkanesulfonyl-$C_1$-$C_4$ alkoxy, such as methanesulfonyl-methoxy or 3-methanesulfonyl-propyloxy.

Lower alkanesulfonylamino-lower alkoxy is, for example, $C_1$-$C_7$ alkanesulfonylamino-$C_1$-$C_4$ alkoxy, such as ethanesulfonylaminomethoxy, 2-ethanesulfonylaminoethoxy, 3-ethane-sulfonylaminopropyloxy, or 3-(1,1-dimethylethanesulfonylamino)propyloxy.

Lower alkanesulfonylamino-lower alkyl is, for example, $C_1$-$C_7$ alkanesulfonylamino-$C_1$-$C_4$ alkyl, such as ethanesulfonylaminomethyl, 2-ethanesulfonylaminoethyl, 3-ethanesulfonyl-aminopropyl, or 3-(1,1-dimethylethanesulfonylamino)propyl.

Lower alkanesulfonyl-lower alkyl is, for example, $C_1$-$C_7$ alkanesulfonyl-$C_1$-$C_4$ alkyl, such as ethanesulfonylmethyl, 2-ethanesulfonylethyl, 3-ethanesulfonylpropyl, or 3-(1,1-dimethyl-ethanesulfonyl)propyl.

Lower alkenyl is, for example, $C_2$-$C_7$ alkenyl, such as vinyl or allyl.

Lower alkenyloxy is, for example, $C_2$-$C_7$ alkenyloxy, such as allyloxy.

Lower alkenyloxy-lower alkoxy is, for example, $C_3$-$C_7$ alkenyloxy-$C_1$-$C_4$ alkoxy, such as allyloxymethoxy.

Lower alkenyloxy-lower alkyl is, for example, $C_3$-$C_7$ alkenyloxy-$C_1$-$C_4$ alkyl, such as allyloxymethyl.

Lower alkoxy is, for example, $C_1$-$C_7$ alkoxy, preferably $C_1$-$C_5$ alkoxy, such as methoxy, ethoxy, propyloxy, isopropyloxy, butyloxy, isobutyloxy, secondary butyloxy, tertiary butyloxy, pentyloxy, or a hexyloxy or heptyloxy group.

Lower alkoxycarbonyl is, for example, $C_1$-$C_7$ alkoxycarbonyl, preferably $C_1$-$C_5$ alkoxycarbonyl, such as methoxycarbonyl, ethoxycarbonyl, propyloxycarbonyl, isopropyloxycarbonyl, butyloxycarbonyl, isobutyloxycarbonyl, secondary butyloxycarbonyl, tertiary butyloxy, pentyloxycarbonyl, or a hexyloxycarbonyl or heptyloxycarbonyl group.

Lower alkoxycarbonyl-(hydroxy)-lower alkyl is, for example, $C_1$-$C_4$ alkoxycarbonyl-$C_1$-$C_7$ (hydroxy)alkyl, such as 1-methoxycarbonyl- or 1-ethoxycarbonyl-2-hydroxyethyl.

Lower alkoxycarbonylamino-lower alkoxy is, for example, $C_1$-$C_7$ alkoxycarbonylamino-$C_2$-$C_7$ alkoxy, preferably $C_2$-$C_5$ alkoxycarbonylamino-$C_2$-$C_7$ alkoxy, such as methoxycarbonylamino-$C_2$-$C_7$ alkoxy, ethoxycarbonylamino-$C_2$-$C_7$ alkoxy, propyloxycarbonylamino-$C_2$-$C_7$ alkoxy, isobutyloxycarbonylamino-$C_2$-$C_7$ alkoxy, butyloxycarbonylamino-$C_2$-$C_7$ alkoxy, isobutyloxycarbonylamino-$C_2$-$C_7$ alkoxy, secondary butyloxycarbonylamino-$C_2$-$C_7$ alkoxy or tertiary butyloxyamino-$C_2$-$C_7$ alkoxy, wherein $C_2$-$C_7$ alkoxy is, for example, methoxy, ethoxy, propyloxy, butyloxy, pentyloxy, or hexyloxy.

Lower alkoxycarbonylamino-lower alkyl is, for example, $C_1$-$C_7$ alkoxycarbonylamino-$C_2$-$C_7$ alkyl, preferably $C_2$-$C_5$ alkoxycarbonylamino-$C_2$-$C_7$ alkyl, such as methoxycarbonyl-$C_2$-$C_7$ alkyl, ethoxycarbonylamino-$C_2$-$C_7$-alkyl, propyloxycarbonylamino-$C_2$-$C_7$ alkyl isopropyloxy-carbonylamino-$C_2$-$C_7$ alkyl, butyloxycarbonylamino-$C_2$-$C_7$ alkyl, isobutyloxycarbonylamino-$C_2$-$C_7$ alkyl, secondary butyloxycarbonylamino-$C_2$-$C_7$ alkyl, or tertiary butyloxyamino-$C_2$-$C_7$ alkyl, wherein $C_2$-$C_7$ alkyl is, for example, ethyl, propyl, butyl, pentyl, or hexyl.

Lower alkoxycarbonyl-lower alkoxy is, for example, $C_1$-$C_4$ alkoxycarbonyl-$C_1$-$C_4$ alkoxy, such as methoxycarbonyl- or ethoxycarbonyl-methoxy, 2-methoxycarbonyl- or 2-ethoxycarbonyl-ethoxy, 2- or 3-methoxycarbonyl- or 2- or 3-ethoxycarbonyl-propyloxy or 4-methoxycarbonyl- or 4-ethoxycarbonyl-butyloxy, especially methoxycarbonyl- or ethoxycarbonyl-methoxy, or 3-methoxycarbonyl- or 3-ethoxycarbonyl-propyloxy.

Lower alkoxycarbonyl-lower alkyl is, for example, $C_1$-$C_4$ alkoxycarbonyl-$C_1$-$C_4$ alkyl, such as methoxycarbonyl-methyl, ethoxycarbonyl-methyl, 2-methoxycarbonyl-ethyl, 2-ethoxycarbonyl-ethyl, 3-methoxycarbonyl-propyl, 3-ethoxycarbonyl-propyl or 4-ethoxycarbonyl-butyl.

Lower alkoxy-lower alkenyl is, for example, $C_1$-$C_4$ alkoxy-$C_2$-$C_4$ alkenyl, such as 4-methoxybut-2-enyl.

Lower alkoxy-lower alkoxy is, for example, $C_1$-$C_4$ alkoxy-$C_2$-$C_4$ alkoxy, such as 2-methoxy-, 2-ethoxy- or 2-propyloxy-ethoxy, 3-methoxy- or 3-ethoxy-propyloxy, or 4-methoxybutyloxy, especially 3-methoxypropyloxy or 4-methoxybutyloxy.

Lower alkoxy-lower alkoxy-lower alkyl is, for example, $C_1$-$C_4$ alkoxy-$C_1$-$C_4$ alkoxy-$C_1$-$C_4$ alkyl, such as 2-methoxy-, 2-ethoxy- or 2-propyloxy-ethoxymethyl, 2-(2-methoxy-, 2-ethoxy- or 2-propyloxy-ethoxy)ethyl, 3-(3-methoxyor 3-ethoxy-propyloxy)propyl, or 4-(2-methoxybutyloxy)-butyl, especially 2-(3-methoxypropyloxy)ethyl or 2-(4-methoxybutyloxy)ethyl.

Lower alkoxy-lower alkyl is, for example, $C_1$-$C_4$ alkoxy-$C_1$-$C_4$ alkyl, such as ethoxymethyl, propyloxymethyl, butyloxymethyl, 2-methoxy-, 2-ethoxy- or 2-propyloxy-ethyl, 3-methoxy- or 3-ethoxy-propyl or 4-methoxybutyl, especially 3-methoxypropyl, or 4-methoxybutyl.

Piperidino-lower alkyl is, for example, piperidine-$C_1$-$C_4$ alkyl or hydroxypiperidino-$C_1$-$C_4$ alkyl, such as piperidinomethyl or 4-hydroxypiperidinomethyl.

Lower alkoxypiperidino-lower alkyl is, for example, $C_1$-$C_4$ alkoxypiperidino-$C_1$-$C_4$ alkyl, such as 4-($C_1$-$C_4$ alkoxy)-piperidinomethyl, especially 4-methoxypiperidinomethyl.

Lower alkyl may be straight-chained or branched and/or bridged and is, for example, corresponding $C_1$-$C_7$ alkyl, such as methyl, ethyl, propyl, isopropyl, butyl, isobutyl, secondary butyl or tertiary butyl, or a pentyl, hexyl or heptyl group. Lower alkyl $R^2$ or $R^3$ is especially $C_2$-$C_7$ alkyl; lower alkyl $R^5$ or $R^7$ is especially branched $C_3$-$C_7$ alkyl; and lower alkyl $R^8$ or $R^3$ is, for example, straight-chained, branched or bridged $C_3$-$C_7$ alkyl.

Lower alkylamino is, for example, $C_1$-$C_4$ alkylamino, such as methylamino, ethylamino, propylamino, butylamino, isobutylamino, secondary butylamino, or tertiary butylamino.

Lower alkylamino-lower alkoxy is, for example, $C_1$-$C_4$ alkylamino-$C_1$-$C_4$ alkoxy, such as propylaminomethoxy, 2-methylamino-, 2-ethylamino-, 2-propylamino- or 2-butylamino-ethoxy, 3-ethylamino- or 3-propylamino-propyloxy or 4-methylaminobutoxy.

Lower alkylamino-lower alkyl is, for example, $C_1$-$C_4$ alkylamino-$C_1$-$C_4$ alkyl, such as propylaminomethyl, 2-methylamino-, 2-ethylamino-, 2-propylamino- or 2-butylamino-ethyl, 3-ethylamino- or 3-propylamino-propyl or 4-methylaminobutyl.

Lower alkylcarbamoyl-lower alkoxy is, for example, N—$C_1$-$C_7$ alkylcarbamoyl-$C_1$-$C_4$ alkoxy, such as methyl- or dimethyl-carbamoyl-$C_1$-$C_4$ alkoxy, e.g., methylcarbamoylmethoxy, 2-methylcarbamoylethoxy, or 3-methylcarbamoylpropyloxy.

Lower alkylenedioxy is, for example, methylenedioxy or ethylenedioxy, but can also be 1,3- or 1,2-propylenedioxy.

Lower alkylsulfamoyl-lower alkyl is, for example, N—$C_1$-$C_7$ alkylsulfamoyl-$C_1$-$C_4$ alkyl, such as N-methyl-, N-ethyl-, N-propyl- or N-butyl-sulfamoyl-$C_1$-$C_4$ alkyl, such as N-methyl-, N-ethyl-, N-propyl- or N-butyl-sulfamoylmethyl, 2-(N-methylsulfamoyl)ethyl, 2-(N-butylsulfamoyl)ethyl, 3-(N-methylsulfamoyl)propyl, 3-(N-butylsulfamoyl)propyl, or 4-(N-methylsulfamoyl)butyl, 4-(N-butylsulfamoyl)butyl or 4-(N,N-dimethylsulfamoyl)butyl, especially N-methyl-, N-butyl-, or N,N-dimethyl-sulfamoylmethyl.

Lower alkylthio-(hydroxy)-lower alkoxy is, for example, $C_1$-$C_4$ alkylthio-$C_1$-$C_4$ (hydroxy)alkoxy, such as 2-hydroxy-3-methylthiopropyloxy.

Lower alkylthio-lower alkoxy is, for example, $C_1$-$C_4$ alkylthio-$C_1$-$C_4$ alkoxy, such as methylthio-$C_1$-$C_4$ alkoxy, e.g. methylthiomethoxy, 2-methylthioethoxy, or 3-methylthiopropyloxy.

Lower alkylthio-lower alkyl is, for example, $C_1$-$C_4$ alkylthio-$C_1$-$C_4$ alkyl, such as methylthio-$C_1$-$C_4$ alkyl, e.g. methylthiomethyl, 2-methylthioethyl, or 3-methylthiopropyl.

N'-Lower alkanoylpiperazino-lower alkoxy is, for example, N'-lower alkanoylpiperazino-$C_1$-$C_4$ alkoxy, such as 4-acetylpiperazinomethoxy.

N'-Lower alkanoylpiperazino-lower alkyl is, for example, N'-$C_2$-$C_7$-lower alkanoylpiperazino-$C_1$-$C_4$ alkyl, such as 4-acetylpiperazinomethyl.

N'-Lower alkylpiperazino-lower alkyl is, for example, N'-$C_1$-$C_4$ alkylpiperazino-$C_1$-$C_4$ alkyl, such as 4-methylpiperazinomethyl.

Oxo-lower alkoxy is, for example, oxo-$C_1$-$C_4$ alkoxy, such as 3,3-dimethyl-2-oxo-butyloxy.

Piperazino-lower alkyl is, for example, piperazino-$C_1$-$C_4$ alkyl, such as piperazinomethyl, 2-piperazinoethyl, or 3-piperazinopropyl.

Piperidino-lower alkoxy is, for example, piperidino-$C_1$-$C_4$ alkoxy, such as piperidinomethoxy, 2-piperidinoethoxy, or 3-piperidinopropyloxy.

Piperidino-lower alkyl is, for example, piperidino-$C_1$-$C_4$ alkyl, such as piperidinomethyl, 2-piperidinoethyl, or 3-piperidinopropyl.

Polyhalo-lower alkanesulfonylamino-lower alkoxy is, for example, trifluoro-$C_1$-$C_7$ alkanesulfonyl-$C_1$-$C_4$ alkoxy, such as trifluoromethanesulfonylaminobutyloxy.

Polyhalo-lower alkanesulfonylamino-lower alkyl is, for example, trifluoro-$C_1$-$C_7$ alkanesulfonyl-$C_1$-$C_4$ alkyl, such as trifluoromethanesulfonylaminobutyl.

Pyrimidinylthio-lower alkoxy is, for example, pyrimidinylthio-$C_1$-$C_4$ alkoxy, such as pyrimidinylthiomethoxy, 2-(pyrimidinylthio)ethoxy, or 3-(pyrimidinylthio)propyloxy.

Pyrrolidino-lower alkoxy is, for example, pyrrolidino-$C_2$-$C_4$ alkoxy, such as 2-pyrrolidinoethoxy, or 3-pyrrolidinopropyloxy.

Pyrrolidino-lower alkyl is, for example, pyrrolidino-$C_1$-$C_4$ alkyl, such as pyrrolidinomethyl, 2-pyrrolidinoethyl, or 3-pyrrolidinopropyl.

S,S-Dioxothiomorpholino-lower alkyl is, for example, S,S-dioxothiomorpholino-$C_1$-$C_4$ alkyl, such as S,S-dioxothiomorpholinomethyl or 2-(S,S-dioxo)thiomorpholinoethyl.

S-Oxothiomorpholino-lower alkyl is, for example, S-oxothiomorpholino-$C_1$-$C_4$ alkyl, such as S-oxothiomorpholinomethyl or 2-(S-oxo)thiomorpholinoethyl.

Sulfamoyl-lower alkyl is, for example, sulfamoyl-$C_1$-$C_4$ alkyl, such as sulfamoyl-$C_1$-$C_4$ alkyl, such as sulfamoylmethyl, 2-sulfamoylethyl, 3-sulfamoylpropyl, or 4-sulfamoylbutyl.

Thiazolinyl-lower alkoxy is, for example, thiazolinyl-$C_1$-$C_4$ alkoxy, such as thiazolinylmethoxy, 2-(thiazolinyl)ethoxy or 3-(thiazolinyl)propyloxy.

Thiazolinyl-lower alkyl is, for example, thiazolinyl-$C_1$-$C_4$ alkyl, such as thiazolinylmethyl, 2-(thiazolinyl)ethyl, or 3-(thiazolinyl)propyl.

Thiazolyl-lower alkoxy is, for example, thiazolyl-$C_1$-$C_4$ alkoxy, such as thiazolylmethoxy, 2-(thiazolyl)ethoxy, or 3-(thiazolyl)propyloxy.

Thiazolyl-lower alkyl is, for example, thiazolyl-$C_1$-$C_4$ alkyl, such as thiazolylmethyl, 2-(thiazolyl)ethyl, or 3-(thiazolyl)propyl.

Thiomorpholino-lower alkyl or S,S-dioxothiomorpholino-lower alkyl is, for example, thiomorpholino-$C_1$-$C_4$ alkyl, such as -methyl or -ethyl, or S,S-dioxothiomorpholino-$C_1$-$C_4$ alkyl, such as -methyl or -ethyl.

Certain of the disclosed compounds may exist in various tautomeric forms. The invention encompasses all such forms, including those forms not depicted structurally.

Certain of the disclosed compound may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms. Thus, "R*" and "S*" denote the relative configurations of substituents around one or more chiral carbon atoms. When a chiral center is not defined as R or S and the configuration at the chiral center is not defined by other means, either configuration can be present or a mixture of both configurations is present.

"Racemate" or "racemic mixture" means a compound of equimolar quantities of two enantiomers, wherein such mixtures exhibit no optical activity; i.e., they do not rotate the plane of polarized light.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enatiomer over the weight of the enantiomer plus the weight of its optical isomer.

When a disclosed compound is named or depicted by structure without indicating the stereochemistry, and the inhibitor has at least one chiral center, it is to be understood that the name or structure encompasses one enantiomer of inhibitor free from the corresponding optical isomer, a racemic mixture of the inhibitor and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

Salts of compounds having salt-forming groups are especially acid addition salts, salts with bases or, where several salt-forming groups are present, can also be mixed salts or internal salts.

Salts are especially the pharmaceutically acceptable or non-toxic salts of compounds of formula I.

Such salts are formed, for example, by compounds of formula I having an acid group, for example a carboxy group or a sulfo group, and are, for example, salts thereof with suitable bases, such as non-toxic metal salts derived from metals of groups Ia, Ib, IIa and IIb of the Periodic Table of the Elements, for example alkali metal salts, especially lithium, sodium or potassium salts, or alkaline earth metal salts, for example magnesium or calcium salts, also zinc salts or ammonium salts, as well as salts formed with organic amines, such as unsubstituted or hydroxy-substituted mono-, di- or tri-alkylamines, especially mono-, di- or tri-lower alkylamines, or with quaternary ammonium bases, for example with methyl-, ethyl-, diethyl- or triethyl-amine, mono-, his- or tris-(2-hydroxy-lower alkyl)-amines, such as ethanol-, diethanol- or triethanol-amine, tris-(hydroxymethyl)-methylamine or 2-hydroxy-tert-butylamines, N,N-di-lower alkyl-N-(hydroxy-lower alkyl)-amines, such as N,N-dimethyl-N-(2-hydroxyethyl)-amine, or N-methyl-D-glucamine, or quaternary ammonium hydroxides, such as tetrabutylammonium hydroxide. The compounds of formula I having a basic group, for example an amino group, can form acid addition salts, for example with suitable inorganic acids, for example hydrohalic acids, such as hydrochloric acid or hydrobromic acid, or sulfuric acid with replacement of one or both protons, phosphoric acid with replacement of one or more protons, e.g., orthophosphoric acid or metaphosphoric acid, or pyrophosphoric acid with replacement of one or more protons, or with organic carboxylic, sulfonic, sulfo or phosphonic acids or N-substituted sulfamic acids, for example, acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, as well as with amino acids, such as the proteinogenic and non-proteinogenic α-amino acids, and with methanesulfonic acid, ethanesulfonic acid, 2-hydroxyethanesulfonic acid, ethane-1,2-disulfonic acid, benzenesulfonic acid, 4-toluenesulfonic acid, naphthalene-2-sulfonic acid, 2- or 3-phosphoglycerate, glucose-6-phosphate, or N-cyclohexylsulfamic acid (forming cyclamates) or with other acidic organic compounds, such as ascorbic acid. Compounds of formula I having acid and basic groups can also form internal salts.

For isolation and purification purposes it is also possible to use pharmaceutically unacceptable salts.

Another embodiment of the invention is a pharmaceutical composition comprising an effective amount of compounds of formula I, Ia, or Ib and a pharmaceutically acceptable carrier therefor.

The compounds of the invention may be used, for example, in the preparation of pharmaceutical compositions that comprise an effective amount of the active ingredient together or in admixture with a significant amount of inorganic or organic, solid or liquid, pharmaceutically acceptable carriers.

The pharmaceutical compositions of the invention are compositions for enteral, such as nasal, rectal or oral, or parenteral, such as intramuscular or intravenous, administration to warm-blooded animals (mammals, especially human beings) that comprise an effective dose of the pharmacologically active ingredient alone or together with a pharmaceutically acceptable carrier. The dose of the active ingredient depends on the species of warm- blooded animal, body weight, age and individual condition, individual pharmacokinetic data, the disease to be treated, and the mode of administration.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragees, tablets, or capsules.

The pharmaceutical compositions of the invention are prepared in a manner known per se, for example by means of conventional dissolving, lyophilising, mixing, granulating, or confectioning processes.

Solutions of the active ingredient, and also suspensions, and especially isotonic aqueous solutions or suspensions, are preferably used, it being possible, for example in the case of lyophilised compositions that comprise the active ingredient alone or together with a carrier, for such solutions or suspensions to be made up prior to use. The pharmaceutical compositions may be sterilized and/or may comprise excipients, for example preservatives, stabilizers, wetting agents and/or emulsifiers, solubilisers, salts for regulating the osmotic pressure and/or buffers, and are prepared in a manner known per se, for example by means of conventional dissolving or lyophilising processes. The said solutions or suspensions may comprise conventional viscosity-increasing substances, such as sodium carboxymethylcellulose, carboxymethylcellulose, dextran, polyvinylpyrrolidone, and gelatin.

Suspensions in oil comprise as the oil component the vegetable, synthetic or semi-synthetic oils customary for injection purposes, for example, liquid fatty acid esters that contain as the acid component a long-chained fatty acid having from 8 to 22, especially from 12 to 22, carbon atoms. Examples include lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid or linoleic acid, if desired with the addition of antioxidants, for example vitamin E, β-carotene, or 3,5-di-tert-butyl-4-hydroxytoluene. The alcohol component of those fatty acid esters has a maximum of 6 carbon atoms and is a mono- or poly-hydric, for example a mono-, di- or tri-hydric, alcohol, for example methanol, ethanol, propanol, butanol or pentanol, or the isomers thereof, but especially glycol and glycerol. Examples of fatty acid esters include ethyl oleate, isopropyl myristate, isopropyl palmitate, polyoxyethylene glycerol trioleate, triglyceride of saturated fatty acids with a chain length of $C_8$-$C_{12}$, but especially vegetable oils, such as cottonseed oil, almond oil, olive oil, castor oil, sesame oil, soybean oil, and groundnut oil.

The injectable compositions are prepared in the customary manner under sterile conditions. The same applies to introducing the compositions into ampoules or vials and sealing the containers.

Pharmaceutical compositions for oral administration can be obtained by combining the active ingredient with solid carriers, if desired granulating a resulting mixture and processing the mixture, if desired or necessary, after the addition of appropriate excipients, into tablets, dragee cores or capsules. They can also be incorporated into plastics carriers that allow the active ingredients to diffuse or be released in measured amounts.

Suitable carriers are especially fillers, such as sugars, for example lactose, saccharose, mannitol or sorbitol, cellulose preparations and/or calcium phosphates, for example tri-calcium phosphate or calcium hydrogen phosphate, and also binders, such as starch pastes using, for example, corn, wheat, rice or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, also carboxy-methyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragee cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and also soft, sealed capsules made of gelatin and a plasticiser, such as glycerol or sorbitol. The dry-filled capsules may comprise the active ingredient in the form of granules, for example with fillers, such as lactose, binders, such as starches, and/or glidants, such as talc or magnesium stearate, and if desired with stabilizers. In soft capsules the active ingredient is preferably dissolved or suspended in suitable oily excipients, such as fatty oils, paraffin oil or liquid polyethylene glycols, it likewise being possible for stabilizers and/or antibacterial agents to be added. Dyes or pigments may be added to the tablets or dragee coatings or to the capsule casings, for example for identification purposes or to indicate different doses of active ingredient.

The compositions of the invention are renin inhibitors. Said compositions contain compounds having a mean inhibition constant ($IC_{50}$) against renin of between about 50,000 nM to about 0.001 nM; preferably between about 100 nM to about 0.001 nM; and more preferably between about 10 nM to about 0.001 nM.

The compositions of the invention reduce blood pressure. Said compositions include compounds having an $IC_{50}$ for renin of between about 50,000 nM to about 0.001 nM; preferably between about 100 nM to about 0.001 nM; and more preferably between about 10 nM to about 0.001 nM.

The invention includes a therapeutic method for treating or ameliorating a renin mediated disorder in a subject in need thereof comprising administering to a subject in need thereof an effective amount of a compound of formula I, or the enantiomers, diastereomers, or salts thereof or composition thereof. Renin mediated disorders include hypertension; heart failure such as (acute and chronic) congestive heart failure; left ventricular dysfunction; cardiac hypertrophy; cardiac fibrosis; cardiomyopathy (e.g., diabetic cardiac myopathy and post-infarction cardiac myopathy); supraventricular and ventricular arrhythmias; arial fibrillation; atrial flutter; detrimental vascular remodeling; myocardial infarction and its sequelae; atherosclerosis; angina (whether unstable or stable); renal failure conditions, such as diabetic nephropathy; glomerulonephritis; renal fibrosis; scleroderma; glomerular sclerosis; microvascular complications, for example, diabetic retinopathy; renal vascular hypertension; complications from diabetes such as nephropathy, vasculopathy and neuropathy; diseases of the coronary vessels; proteinuria; albumenuria; post-surgical hypertension; metabolic syndrome; obesity; restenosis following angioplasty; ocular vascular complications, for example, raised intra-ocular pressure, glaucoma, and retinopathy; abnormal vascular growth; angiogenesis-related disorders, such as neovascular age related macular degeneration; hyperaldosteronism; anxiety states; and cognitive disorders (Fisher N. D.; Hollenberg N. K. *Expert Opin. Investig. Drugs.* 2001, 10, 417-26).

Administration methods include administering an effective amount (i.e., a therapeutically effective amount) of a compound or composition of the invention at different times during the course of therapy or concurrently in a combination form. The methods of the invention include all known therapeutic treatment regimens.

"Prodrug" means a pharmaceutically acceptable form of an effective derivative of a compound (or a salt thereof) of the invention, wherein the prodrug may be: 1) a relatively active precursor which converts in vivo to a compound of the invention; 2) a relatively inactive precursor which converts in vivo to a compound of the invention; or 3) a relatively less active component of the compound that contributes to therapeutic activity after becoming available in vivo (i.e., as a metabolite). See "Design of Prodrugs", ed. H. Bundgaard, Elsevier, 1985.

"Metabolite" means a pharmaceutically acceptable form of a metabolic derivative of a compound (or a salt thereof) of the invention, wherein the derivative is an active compound that contributes to therapeutic activity after becoming available in vivo.

"Effective amount" means that amount of active compound agent that elicits the desired biological response in a subject. Such response includes alleviation of the symptoms of the disease or disorder being treated. The effective amount of a compound of the invention in such a therapeutic method to be administered to warm-blooded animals, for example human beings, of, for example, approximately 70 kg body weight, especially the doses effective in the inhibition of the enzyme renin, in lowering blood pressure and/or in improving the symptoms of glaucoma, are from approximately 3 mg to approximately 3 g, preferably from approximately 10 mg to approximately 1 g, for example approximately from 20 mg to 200 mg, per person per day, divided preferably into 1 to 4 single doses which may, for example, be of the same size. Usually, children receive about half of the adult dose. The dose necessary for each individual can be monitored, for example by measuring the serum concentration of the active ingredient, and adjusted to an optimum level.

The invention includes the use of a compound of the invention for the preparation of a composition for treating or ameliorating a renin mediated chronic disorder or disease or infection in a subject in need thereof, wherein the composition comprises a mixture one or more compounds of the invention and an optional pharmaceutically acceptable carrier.

"Pharmaceutically acceptable carrier" means compounds and compositions that are of sufficient purity and quality for use in the formulation of a composition of the invention and that, when appropriately administered to an animal or human, do not produce an adverse reaction.

"Renin mediated disorder or disease" includes disorders or diseases associated with the elevated expression or overexpression of renin and conditions that accompany such diseases.

An embodiment of the invention includes administering a renin inhibiting compound of formula I or composition thereof in a combination therapy (see U.S. Pat. No. 5,821, 232, U.S. Pat. No. 6,716,875, U.S. Pat. No. 5,663,188, Fossa, A. A.; DePasquale, M. J.; Ringer, L. J.; Winslow, R. L. "Synergistic effect on reduction in blood pressure with coadministration of a renin inhibitor or an angiotensin-converting enzyme inhibitor with an angiotensin II receptor antagonist" *Drug Development Research* 1994, 33(4), 422-8) with one or more additional agents for the treatment of hypertension including α-blockers, β-blockers, calcium channel blockers, diuretics, natriuretics, saluretics, centrally acting antihypertensives, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, or endothelin receptor antagonists.

α-Blockers include doxazosin, prazosin, tamsulosin, and terazosin.

β-Blockers for combination therapy are selected from atenolol, bisoprol, metoprolol, acetutolol, esmolol, celiprolol, taliprolol, acebutolol, oxprenolol, pindolol, propanolol, bupranolol, penbutolol, mepindolol, carteolol, nadolol, carvedilol, and their pharmaceutically acceptable salts.

Calcium channel blockers include dihydropyridines (DHPs) and non-DHPs. The preferred DHPs are selected from the group consisting of amlodipine, felodipine, ryosidine, isradipine, lacidipine, nicardipine, nifedipine, nigulpidine, niludipine, nimodiphine, nisoldipine, nitrendipine, and nivaldipine and their pharmaceutically acceptable salts. Non-DHPs are selected from flunarizine, prenylamine, diltiazem, fendiline, gallopamil, mibefradil, anipamil, tiapamil, and verampimil and their pharmaceutically acceptable salts.

A diuretic is, for example, a thiazide derivative selected from amiloride, chlorothiazide, hydrochlorothiazide, methylchiorothiazide, and chlorothalidon.

Centrally acting antihypertensives include clonidine, guanabenz, guanfacine and methyldopa.

ACE inhibitors include alacepril, benazepril, benazaprilat, captopril, ceronapril, cilazapril, delapril, enalapril, enalaprilat, fosinopril, lisinopril, moexipiril, moveltopril, perindopril, quinapril, quinaprilat, ramipril, ramiprilat, spirapril, temocapril, trandolapril, and zofenopril. Preferred ACE inhibitors are benazepril, enalpril, lisinopril, and ramipril.

Dual ACE/NEP inhibitors are, for example, omapatrilat, fasidotril, and fasidotrilat.

Preferred ARBs include candesartan, eprosartan, irbesartan, losartan, olmesartan, tasosartan, telmisartan, and valsartan.

Preferred aldosterone synthase inhibitors are anastrozole, fadrozole, and exemestane.

Preferred aldosterone-receptor antagonists are spironolactone and eplerenone.

A preferred endothelin antagonist is, for example, bosentan, enrasentan, atrasentan, darusentan, sitaxentan, and tezosentan and their pharmaceutically acceptable salts.

An embodiment of the invention includes administering an aspartic protease inhibitor disclosed herein or composition thereof in a combination therapy with one or more additional agents for the treatment of AIDS including reverse transcriptase inhibitors, non-nucleoside reverse transcriptase inhibitors, other HIV protease inhibitors, HIV integrase inhibitors, entry inhibitors (including attachment, co-receptor and fusion inhibitors), antisense drugs, and immune stimulators.

Specific reverse transcriptase inhibitors are zidovudine, didanosine, zalcitabine, stavudine, lamivudine, abacavir, tenofovir, and emtricitabine.

Specific non-nucleoside reverse transcriptase inhibitors are nevirapine, delaviridine, and efavirenz.

Specific HIV protease inhibitors are saquinavir, ritonavir, indinavir, nelfinavir, amprenavir, lopinavir, atazanavir, and fosamprenavir.

Specific HIV integrase inhibitors are L-870,810 and S-1360.

A specific attachment and fusion inhibitor is enfuvirtide.

Entry inhibitors include compounds that bind to the CD4 receptor, the CCR5 receptor or the CXCR4 receptor. Specific examples of entry inhibitors include enfuvirtide (a peptidomimetic of the HR2 domain in gp41) and sifurvitide.

An embodiment of the invention includes administering a compound disclosed herein or composition thereof in a combination therapy with one or more additional agents for the treatment of Alzheimer's disease including tacrine, donepezil, rivastigmine, galantamine, and memantine.

An embodiment of the invention includes administering a compound disclosed herein or composition thereof in a combination therapy with one or more additional agents for the treatment of malaria including artemisinin, chloroquine, halofantrine, hydroxychloroquine, mefloquine, primaquine, pyrimethamine, quinine, and sulfadoxine.

Combination therapy includes co-administration of the compound of the invention and said other agent, sequential administration of the compound and the other agent, administration of a composition containing the compound and the other agent, or simultaneous administration of separate compositions containing of the compound and the other agent.

The compounds of the invention have enzyme-inhibiting properties. In particular, they inhibit the action of the natural enzyme renin. The latter passes from the kidneys into the blood where it effects the cleavage of angiotensinogen, releasing the decapeptide angiotensin I which is then cleaved in the blood, lungs, the kidneys and other organs by angiotensin converting enzyme to form the octapeptide angiotensin II. The octapeptide increases blood pressure both directly by binding to its receptor, causing arterial vasoconstriction, and indirectly by liberating from the adrenal glands the sodium-ion-retaining hormone aldosterone, accompanied by an increase in extracellular fluid volume. That increase can be attributed to the action of angiotensin II. Inhibitors of the enzymatic activity of renin bring about a reduction in the formation of angiotensin I. As a result a smaller amount of angiotensin II is produced. The reduced concentration of that active peptide hormone is the direct cause of the hypotensive effect of renin inhibitors.

In the course of the processes described below for the preparation of compounds of formula I, functional groups in starting materials and intermediates which are prone to participate in undesired side reactions, especially amino, carboxy, hydroxy, and mercapto groups, can be protected by suitable conventional protecting groups which are customarily used in the synthesis of peptide compounds, and also in the synthesis of cephalosporins and penicillins as well as nucleic acid derivatives and sugars. Those protecting groups may already be present in the precursors and are intended to protect the functional groups in question against undesired secondary reactions, such as acylation, etherification, esterification, oxidation, solvolysis, etc. In certain cases the protecting groups can additionally cause the reactions to proceed selectively, for example stereoselectively. It is characteristic of protecting groups that they can be removed easily, i.e. without undesired secondary reactions taking place, for example by acid treatment, fluoride treatment, solvolysis, reduction, photolysis, and also enzymatically, for example under physiological conditions. Protecting groups may also be present in the end products. Compounds of formula I having protected functional groups may have greater metabolic stability or pharmacodynamic properties that are better in some other way than the corresponding compounds having free functional groups.

The protection of functional groups by such protecting groups, the protecting groups themselves, and the reactions for their removal are described, for example, in standard works such as T. W. Greene and P. G. M. Wuts "Protective Groups in Organic Synthesis" John Wiley & Sons, Inc., New York 1999. In the schemes below protecting groups are not shown.

The first process of the invention for the preparation of compounds of formula I wherein A=N comprises reacting an amine of formula II with an activated carboxylic acid of formula III followed by removal of any protecting groups.

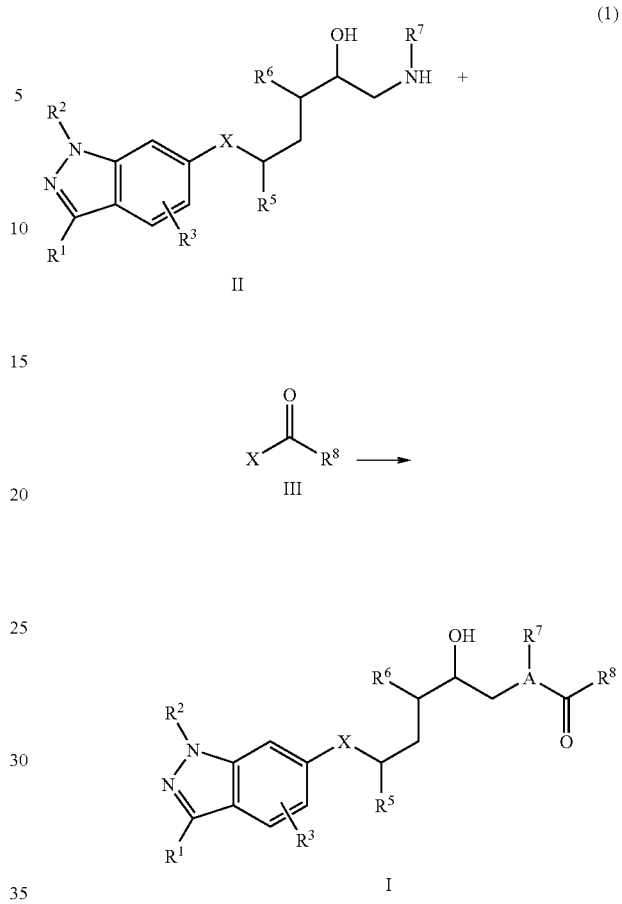

Activated carboxylic acids of formula III may be prepared from carboxylic acids IV and isolated e.g. X=Cl or may be prepared from IV in situ using peptide coupling reagents, such as DCC, EDC, HATU and isobutylchloroformate, well known to those skilled in the art.

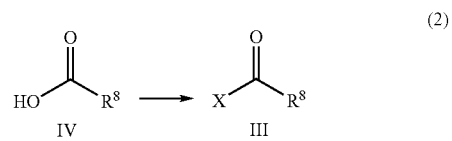

Amine compounds of formula II can be prepared, for example, by reacting an epoxide compound of formula V with an amine of formula VI:

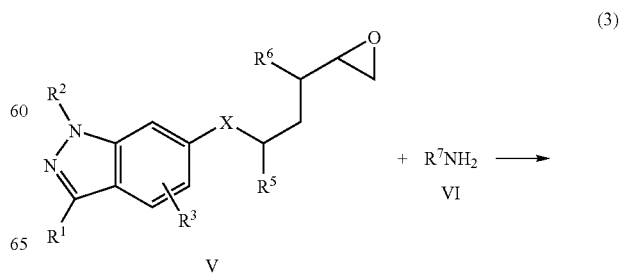

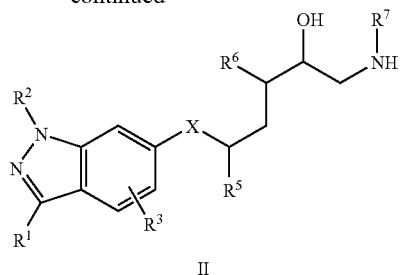

II where $R_7$ is defined as in formula I; followed by appropriate protecting group manipulation.

Amine compounds of formula II wherein $R^7$=H can also be prepared by reduction of azide compounds of formula VII using hydrogen gas in the presence of a transition metal catalyst, for example Raney nickel or platinum or palladium catalysts, for example platinum or palladium on active carbon, or with triphenylphosphine in an aqueous-organic solvent mixture (Staudinger reduction). Azide compounds VII can be prepared by reacting by reacting an epoxide compound of formula V with nucleophilic azide source such as sodium azide in an organic solvent such as DMF or acetonitrile:

(4)

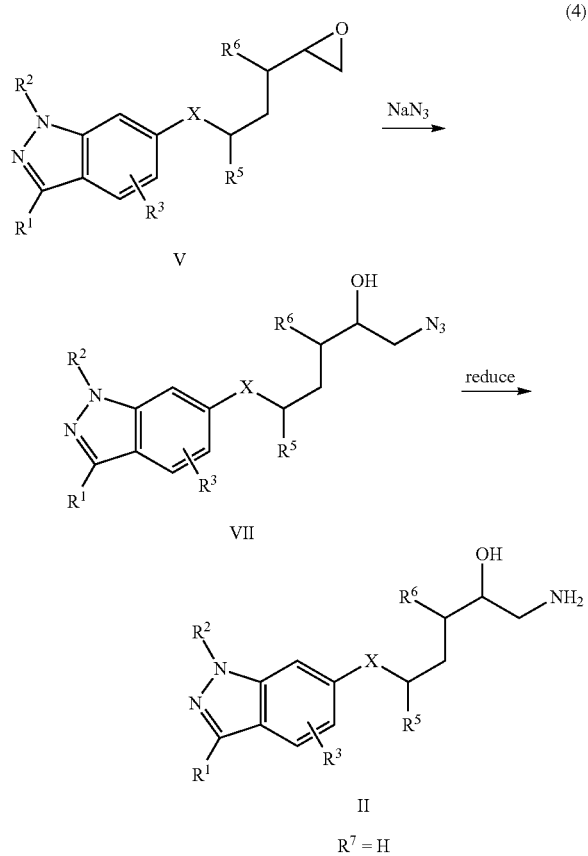

Epoxide compounds of formula V can, in turn, be prepared in a number of ways including, for example, by reacting with aldehyde compounds of formula VIII with trimethylsulfoxonium Iodide or trimethylsulfonium iodide (J. Aube "Epoxidation and Related Processes" Chapter 3.2 in Volume 1 of "Comprehensive Organic Synthesis" Edited by B. M. Trost, I. Fleming and Stuart L. Schreiber, Pergamon Press New York, 1992).

(5)

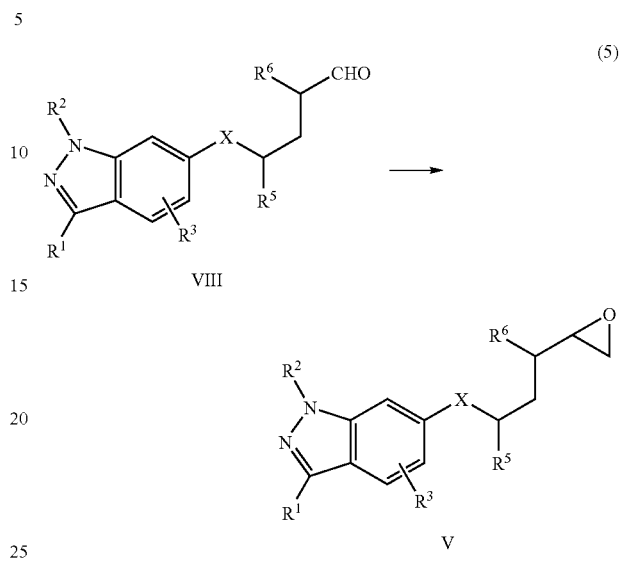

Compounds of formula VIII can be prepared from compounds of formula IX, wherein $R^{20}$ is lower alkyl or aryl-lower alkyl, in a number of ways.

(6)

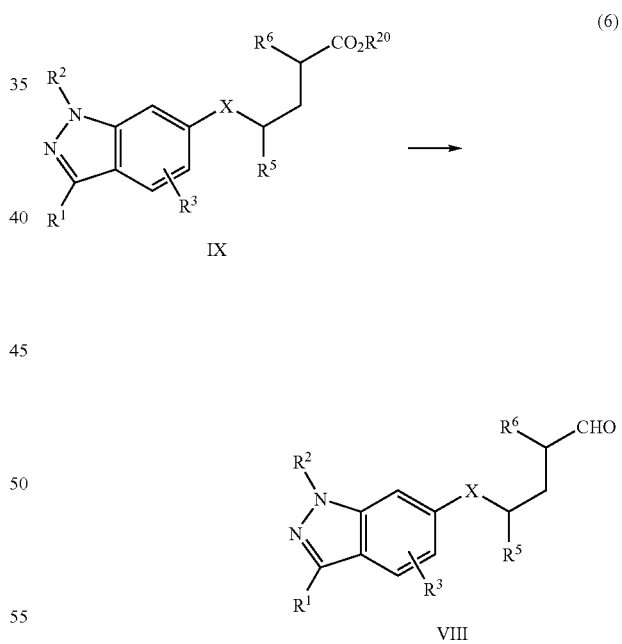

For example, compounds of formula IX can be converted to compounds of formula VIII wherein $R^{20}$ is for example lower alkyl by direct reduction from ester to aldehyde using specialized reagents and conditions known to minimize over-reduction (I. T. Harrison and S. Harrison "Compendium of Organic Synthetic Methods" Section 53, pp 152-153, John Wiley and Sons, New York 1971). One method of carrying out this transformation is by treatment with diisobutyl aluminum hydride in an organic solvent at lowered temperatures.

Alternately, compounds of formula VIII can be prepared from alcohol compounds of formula X:

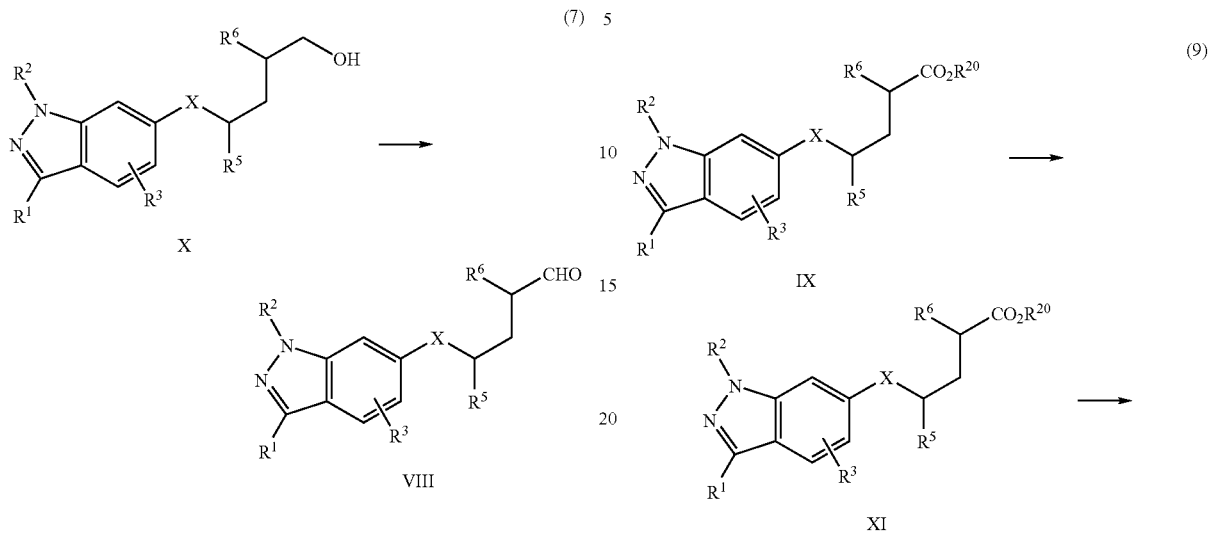

using one of several oxidation protocols which are designed to minimize overoxidation (I. T. Harrison and S. Harrison "Compendium of Organic Synthetic Methods" Section 48, pp 137-143, John Wiley and Sons, New York 1971). Such oxidation protocols include oxalyl chloride/dimethyl sulfoxide (Swern oxidation), (1,1,1-triacetoxy)-1,1-dihydro-1,2-dihydro-1,2-benziodoxol-3(1H)-one (Dess-Martin periodinane), sulfur trioxide/pyridine or tetrapropylammonium perruthenate (TPAP).

Alcohol compounds of formula XI are prepared from ester compounds of formula X by a variety of reducing agents (I. T. Harrison and S. Harrison "Compendium of Organic Synthetic Methods" Section 38, pp 87-91, John Wiley and Sons, New York 1971) including, for example, lithium aluminum hydride.

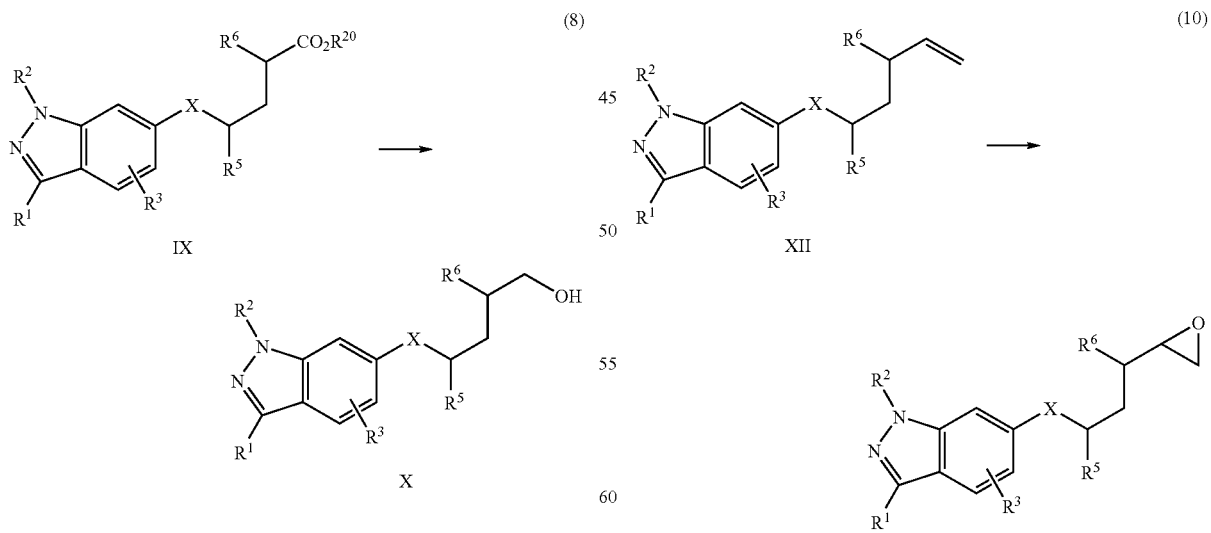

As another example, compounds of formula IX can be hydrolyzed to carboxylic acid compounds of formula XI (I. T. Harrison and S. Harrison "Compendium of Organic Synthetic Methods" Section 23, pp 42-46, John Wiley and Sons, New York 1971). Compounds of formula XI can be converted to alcohol compounds of formula X using a wide variety of reducing agents and conditions (I. T. Harrison and S. Harrison "Compendium of Organic Synthetic Methods" Section 32, pp 76-78, John Wiley and Sons, New York 1971).

Alternately, epoxide compounds of formula V can be prepared from alkene compounds of formula XII by epoxidation of the alkene with for example mCPBA, monoperphthalic acid, peracetic acid, dimethyldioxirane, $H_2O_2$/benzonitrile.

Alkene compounds of formula XII are prepared from aldehyde compounds of formula VIII utilizing the Wittig reaction or the Tebbe reagent.

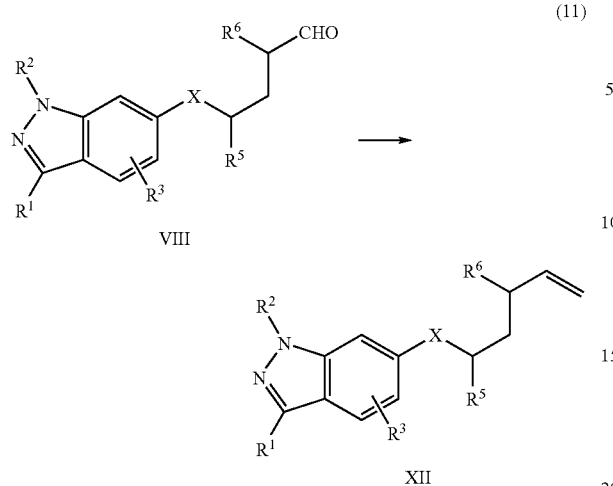

Compounds of formula II in which $R^7$ is a lower alkyl, certain lower haloalkyl groups, certain lower alkoxyalkyl groups or certain lower lower haloalkoxy-lower alkyl groups are prepared by reductive alkylation of primary amines of formula II wherein $R^7$=H with aldehydes of formula XIII wherein $R^{7a}$ is the lower homolog of $R^7$ (E. W. Baxter and A. B. Reitz "Reductive aminations of carbonyl compounds with borohydride and borane reducing agents" in Organic Reactions Volume 59 pp 1-714, Edited by L. E. Overman, John Wiley and Sons, New York, 2002).

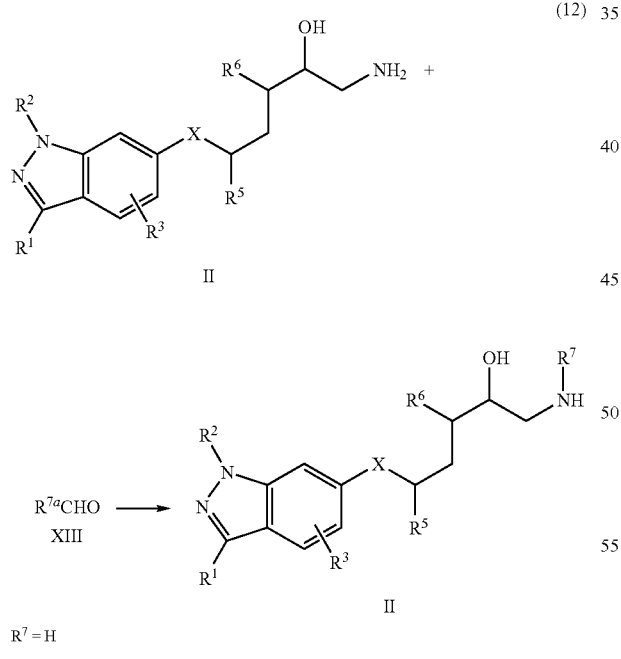

Compounds of Formula IX wherein $R^6$ is an optionally protected amino group are prepared by (i) deprotonation of a dihydropyrazine of formula XIV wherein $R^{20}$ is Me or Et, (ii) alkylation with a halide of formula XV wherein Hal is preferably Br or I and (iii) hydrolysis, optionally followed by (iv) appropriate protecting group manipulations:

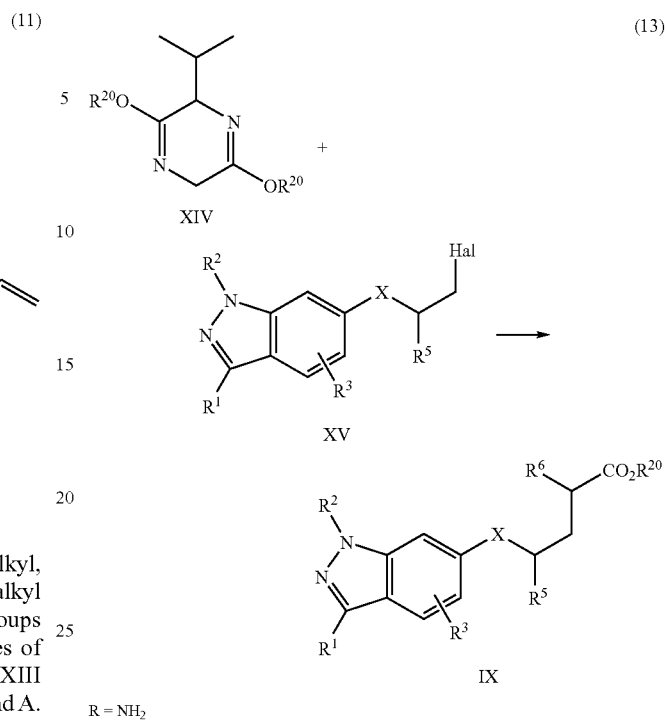

In a second process of the invention a compound of formula I wherein X=CHOH is prepared by addition of an organometallic of formula XVI, wherein X=Li, MgI, MgBr, or MgCl, to an aldehyde of formula XVII followed by removal of any protecting groups:

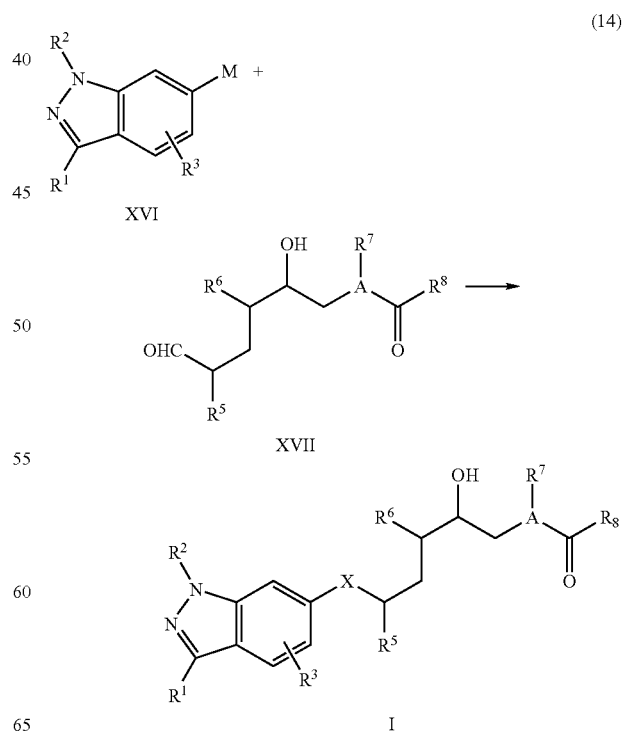

Aldehydes of formula XVII are prepared from alcohols of formula XVIII by oxidation using for example Swern conditions or the Dess-Martin periodinane:

(15)

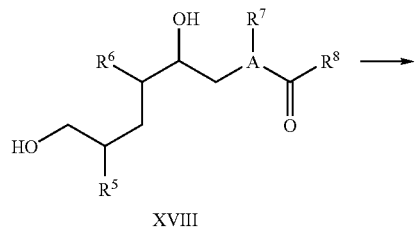

XVIII

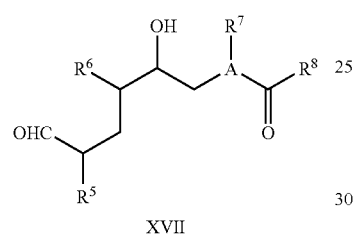

XVII

Alcohols of formula XVIII wherein A=N are prepared by acylation of amines of formula XIX with activated carboxylid acids of formula III:

(16)

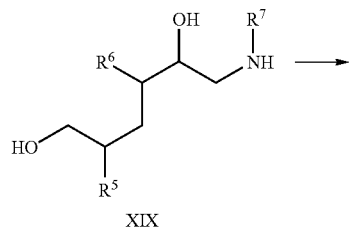

XIX

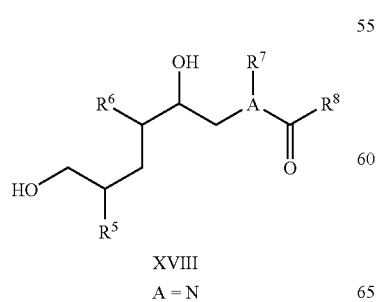

XVIII
A = N

Amines of formula XIX are prepared by processes analogous to those shown in reactions (3) and (4).

Organometallics of formula XVI are prepared from halides of formula XX, wherein Hal is preferably Br or I, by treatment with Mg or alkyllithiums:

(17)

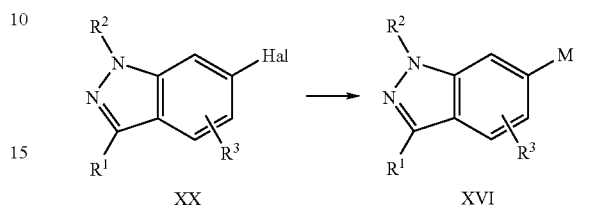

XX          XVI

In a third process of the invention a compound of formula I wherein A=CH and $R^8$ is $NR^9R^{10}$ is prepared by addition of an amine of formula XXII to a lactone XXI followed by removal of any protecting groups:

(18)

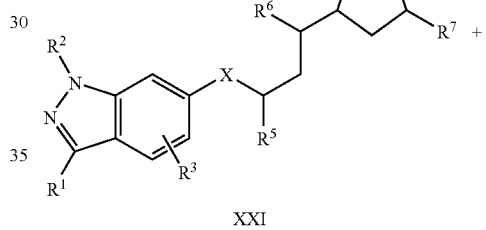

XXI

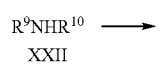

XXII

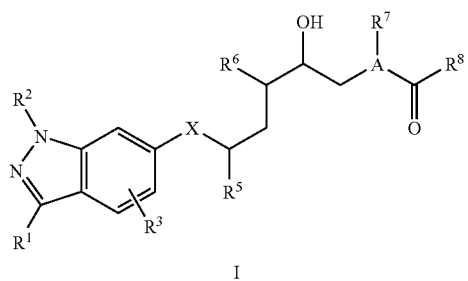

I
A = CH, $R^8$ = $NR^9R^{10}$

Lactones of formula XXI are prepared by oxidation of diols of formula XXIII:

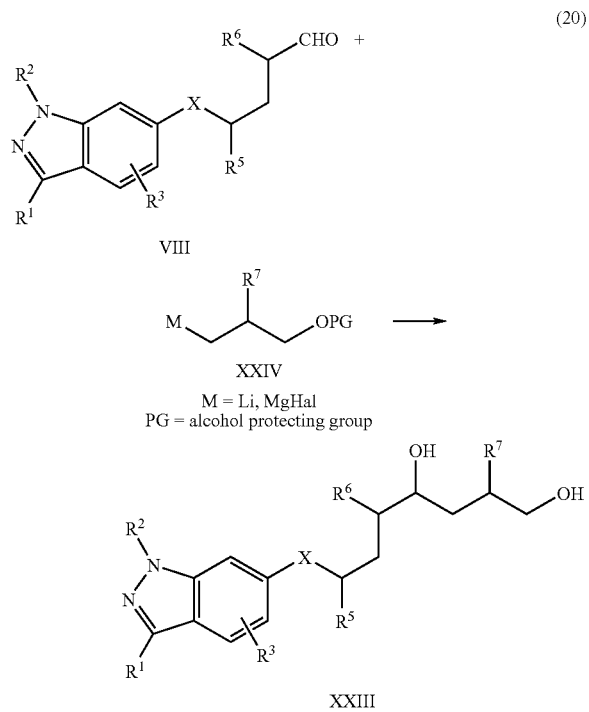

Diols of formula XXIII are prepared by addition of organometallics of formula XXIV to aldehydes of formula VIII followed by protecting group removal:

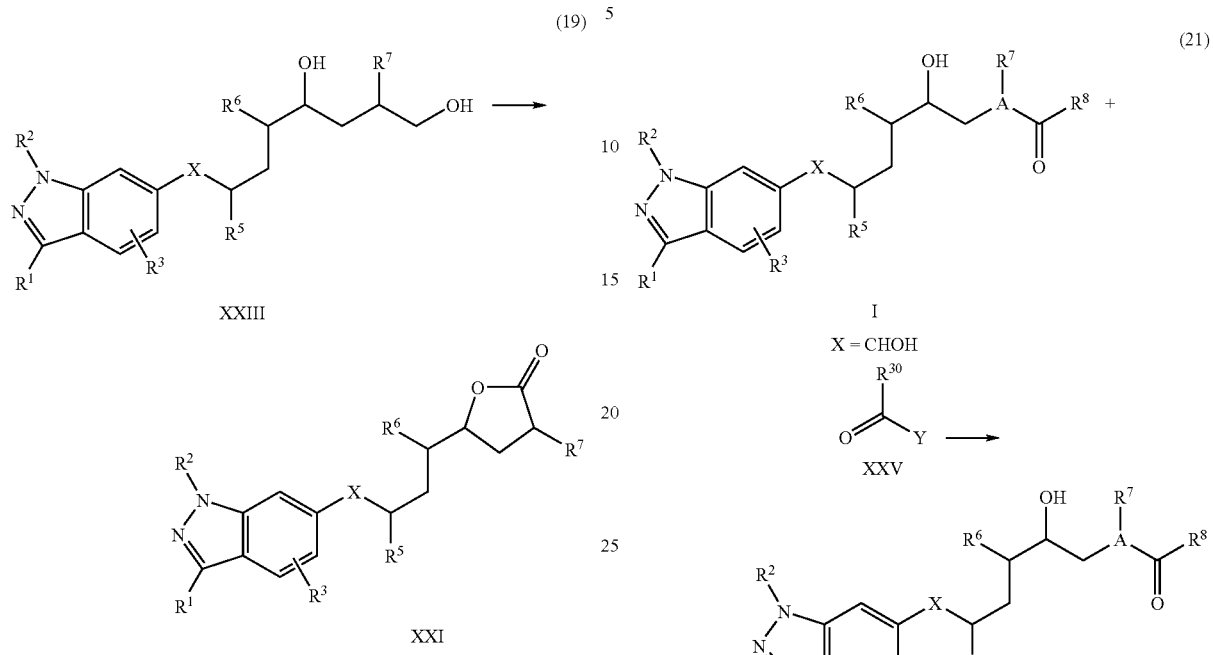

In a fourth process of the invention a compound of formula I wherein X is lower alkanoyloxymethylene is prepared from a formula I wherein X is hydroxymethylene by acylation with an activated carboxylic acid XXV wherein $R^{30}$ is lower alkyl and Y is as described for III above followed by protecting group removal:

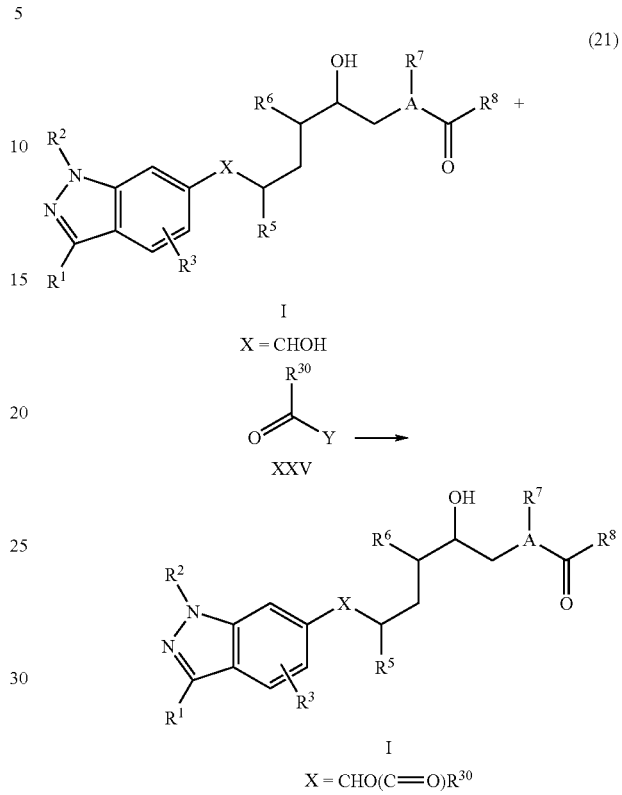

It is also possible for salts of compounds of formula I obtainable in accordance with the process to be converted in a manner known per se into the free compounds, for example by treatment with a base, such as an alkali metal hydroxide, a metal carbonate or metal hydrogen carbonate, or ammonia, or another of the salt-forming bases mentioned at the beginning, or with an acid, such as a mineral acid, for example with hydrochloric acid, or another of the salt-forming acids mentioned at the beginning.

Resulting salts can be converted into different salts in a manner known per se: acid addition salts, for example, by treatment with a suitable metal salt, such as a sodium, barium or silver salt, of a different acid in a suitable solvent in which an inorganic salt being formed is insoluble and is therefore eliminated from the reaction equilibrium, and basic salts by freeing of the free acid and conversion into a salt again.

The compounds of formula I, including their salts, may also be obtained in the form of hydrates or may include the solvent used for crystallization.

As a result of the close relationship between the novel compounds in free form and in the form of their salts, any reference herein to the free compounds and their salts is to be understood as including also the corresponding salts and free compounds, respectively, as appropriate and expedient.

Stereoisomeric mixtures, i.e., mixtures of diastereoisomers and/or enantiomers, such as racemic mixtures, can be separated into the corresponding isomers in a manner known per se by suitable separating processes. For example, mixtures of diastereoisomers can be separated into the individual diastereoisomers by fractional crystallization, chromatography, solvent partition, etc. Racemates can be separated from one another, after conversion of the optical antipodes into diastereoisomers, for example by reaction with optically active compounds, for example optically active acids or bases, by chromatography on column materials charged with optically active compounds or by enzymatic methods, for example by selective reaction of only one of the two enantiomers. This separation can be carried out either at the stage of one of the starting materials or with the compounds of formula I themselves.

In a compound of formula I the configuration at individual chirality centers can be selectively reversed. For example, the configuration of asymmetric carbon atoms that carry nucleophilic substituents, such as amino or hydroxy, can be reversed by second order nucleophilic substitution, optionally after conversion of the bonded nucleophilic substituent into a suitable nucleofugal leaving group and reaction with a reagent introducing the original substituent, or the configuration at carbon atoms having hydroxy groups can be reversed by oxidation and reduction, analogously to patent application EP 236,734.

Another embodiment of the invention is those forms of the process in which a compound obtainable as an intermediate at any stage is used as a starting material and the remaining steps are carried out or the process is interrupted at any stage, or a starting material is formed under the reaction conditions or is used in the form of a reactive derivative or salt, or a compound obtained in accordance with the process of the invention is formed under the process conditions and further processed in situ. It is preferable to use those starting materials which result in the compounds described above.

Representative compounds of the invention can be synthesized in accordance with the general synthetic schemes described above and are illustrated in the examples that follow. The methods for preparing the various starting materials used in the schemes and examples are well within the knowledge of persons skilled in the art.

The following abbreviations have the indicated meanings:
aq aqueous
Boc tert-butoxy carbonyl or t-butoxy carbonyl
(Boc)$_2$O di-tert-butyl dicarbonate
brine saturated aqueous sodium chloride
CH$_2$Cl$_2$ methylene chloride
CH$_3$CN or MeCN acetonitrile
Cpd compound
d day
DBU 1,8-diazabicyclo[5.4.0]undec-7-ene
DMAP 4-(dimethylamino)pyridine
DMF N,N-dimethyl formamide
DMSO Dimethyl sulfoxide
DMPU 1,3-dimethyl-3,4,5,6-tetrahydro-2(1H)-pyrimidinone
EDC.HCl 1-[3-(dimethylamino)propyl]-3-ethylcarbodiimide hydrochloride
eq, equiv equivalents
Et ethyl
EtOAc ethyl acetate
Fmoc 1-[[(9H-fluoren-9-ylmethoxy)carbonyl]oxy]-
Fmoc-OSu 1-[[(9H-fluoren-9-ylmethoxy)carbonyl]oxy]-2,5-pyrrolidinedione
h, hr hour
HBTU O-benzotriazol-1-yl-N,N,N',N'-tetramethyluronium hexafluorophosphate
HOBt 1-hydroxybenzotriazole
KHMDS potassium hexamethyldisilazane
LAH or LiAlH$_4$ lithium aluminum hydride
LHMDS lithium hexamethyldisilazane
Me methyl
MeOH methanol
MsCl methanesulfonyl chloride
min minute
MS mass spectrum
NaH sodium hydride
NaHCO$_3$ sodium bicarbonate
NaN$_3$ sodium azide
NaOH sodium hydroxide
Na$_2$SO$_4$ sodium sulfate
Pd$_2$(dba)$_3$ tris(dibenzylideneacetone)dipalladium(0)
Ph or PH phenyl
RT/rt/r.t. room temperature
satd saturated
SOCl$_2$ thionyl chloride
TEA triethylamine or Et$_3$N
Teoc 1-[2-(trimethylsilyl)ethoxycarbonyloxy]-
Teoc-OSu 1-[2-(trimethylsilyl)ethoxycarbonyloxy]pyrrolidin-2,5-dione
TFA trifluoroacetic acid
THF tetrahydrofuran
tlc thin layer chromatography
TMSCl chlorotrimethylsilane or trimethylsilyl chloride
t$_R$ retention time Compound names were generated with the assistance of ChemDraw® versions 8.0 and 9.0 (CambridgeSoft Corporation, 100 CambridgePark Drive, Cambridge, Mass. 02140 USA). When the stereochemistry at a chiral center is not defined in the compound name this indicates that the sample prepared contained a mixture of isomers at this center.

Preparation 1

6-iodo-1-(3-methoxypropyl)-1H-indazole

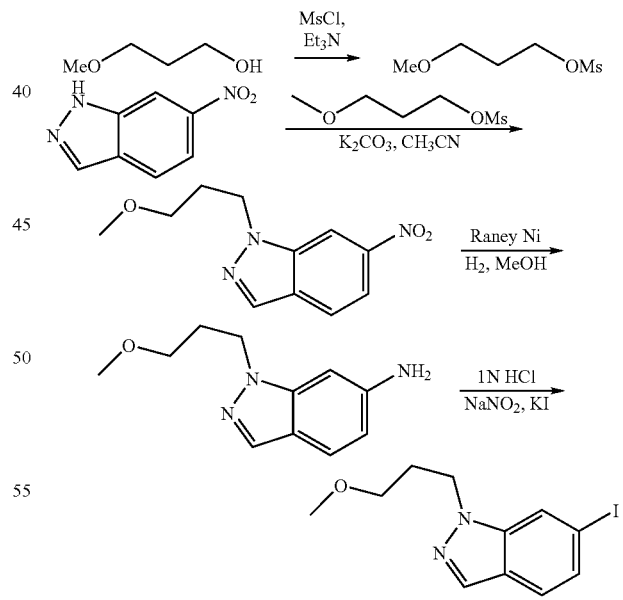

Step 1. 3-Methoxypropyl methanesulfonate

To a stirred solution of 3-methoxy-propan-1-ol (300 g, 3.3 mol) in anhydrous CH$_2$Cl$_2$ (3 L) was added triethylamine (790 mL, 5.7 mol). The mixture was cooled to 0° C. and methanesulfonyl chloride (376 mL, 4.8 mol) in anhydrous CH$_2$Cl$_2$ (1 L) added dropwise. After stirring for 2 h at rt, the mixture was washed with water and brine, dried and evaporated to give the crude product as an oil (540 g, yield 96%) that was used in the next step without purification. $^1$H NMR (400 MHz, CDCl$_3$): δ 3.40-3.37 (t, J=6.0 Hz, 2H), 2.55-2.52 (t, J=6.0 Hz, 2H), 2.40 (s, 3H), 2.06 (s, 3H), 1.08-1.02 (m, 2H).

Step 2. 1-(3-Methoxypropyl)-6-nitro-1H-indazole

A mixture of 6-nitro-1H-indazole (50 g, 0.307 mol), 3-methoxypropyl methanesulfonate (54.3 g, 0.323 mol) and K$_2$CO$_3$ (127 g, 0.921 mol) in CH$_3$CN (1.5 L) was heated at 60° C. overnight. Water (1 L) was added and the CH$_3$CN was removed under reduced pressure and the aqueous residue was extracted with EtOAc (3×500 mL). The combined organic extracts were washed with brine, dried over Na$_2$SO$_4$, filtered and concentrated. The residue was purified by column chromatography on silica gel to give 1-(3-methoxypropyl)-6-nitro-1H-indazole (33 g, 46% yield). $^1$H NMR (400 MHz, CDCl$_3$): δ8.47 (s, 1H), 8.13 (s, 1H), 8.01-7.99 (dd, J=8.8, 2.0 Hz, 1H), 7.83-7.81 (d, J=8.8 Hz, 1H), 4.61-4.57 (t, J=6.4 Hz, 2H), 3.29 (s, 3H), 3.26-3.23 (t, J=5.6 Hz, 2H), 2.23-2.17 (m, 2H).

Step 3. 1-(3-Methoxypropyl)-1H-indazol-6-amine 1-(3-Methoxypropyl)-6-nitro-1H-indazole (33 g, 0.14 mol) was dissolved in methanol (400 mL) and Raney Ni (7 g) was added. The reaction mixture was hydrogenated under an atmosphere of hydrogen at rt for about 2 h. When the starting material has been consumed, the reaction mixture was filtered and the filtrate was concentrated under reduced pressure to give 1-(3-methoxypropyl)-1H-indazol-6-amine (27 g, 94% yield) which was used in the next step without purification. $^1$H NMR (400 MHz, CDCl$_3$): δ 7.84 (s, 1H), 7.51 (d, J=8.4 Hz, 1H), 6.73 (s, 1H), 6.67-6.65 (dd, J=6.8, 2.0 Hz, 1H), 4.36-4.33 (t, J=6.4 Hz, 2H), 4.30-3.80 (brs, 2H), 3.30 (s, 3H), 3.30-3.28 (m, 2H), 2.16-2.10 (m, 2H).

Step 4. 6-Iodo-1-(3-methoxypropyl)-1H-indazole

To a solution of 1-(3-methoxypropyl)-1H-indazol-6-amine (27 g, 0.132 mol) in 1 N aq HCl (264 mL, 0.264 mol) was added dropwise a solution of NaNO$_2$ (11.8 g, 0.171 mol) in water (50 mL) at 0° C. After stirring for an additional 2 h, the reaction mixture was treated with KI (65 g, 0.396 mol) in portions. The reaction mixture was heated at 80° C. for 1 h. The reaction mixture was extracted with EtOAc (3×200 mL). The combined organic extracts were washed with brine, dried over Na$_2$SO$_4$, filtered and concentrated. The residue was purified by column chromatography on silica gel to give 6-iodo-1-(3-methoxypropyl)-1H-indazole (18 g, 43% yield). $^1$H NMR (400 MHz, CDCl$_3$): δ 7.94 (s, 1H), 7.88 (s, 1H), 7.46 (d, J=8.4 Hz, 1H), 7.40-7.38 (dd, J=8.4, 1.2 Hz, 1H), 4.45-4.42 (t, J=6.4 Hz, 2H), 3.30 (s, 3H), 3.25-3.22 (t, J=6.0 Hz, 2H), 2.17-2.11 (m, 2H).

The following intermediates were prepared using procedures analogous to those described above:

1-(3-ethoxypropyl)-6-iodo-1H-indazole using 3-ethoxypropyl methanesulfonate in Step 2;

6-iodo-1-(3-isopropoxypropyl)-1H-indazole using 3-isopropoxypropyl methanesulfonate in Step 2; and 1-(2-cyclopropylethyl)-6-iodo-1H-indazole using 2-cyclopropylethyl methanesulfonate in Step 2.

Preparation 2 tert-Butyl (2S,4S)-4-((1-(3-methoxypropyl)-1H-indazol-6-yl)methyl)-5-methyl-1-oxohexan-2-ylcarbamate

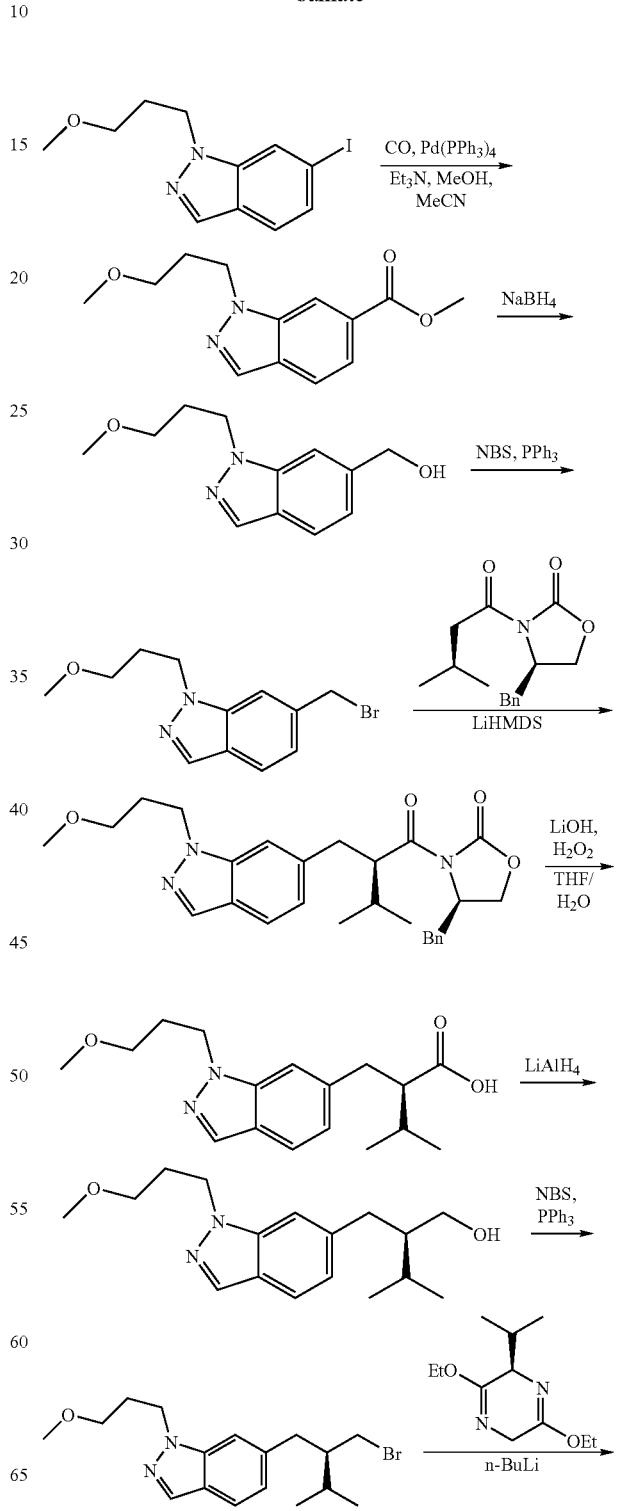

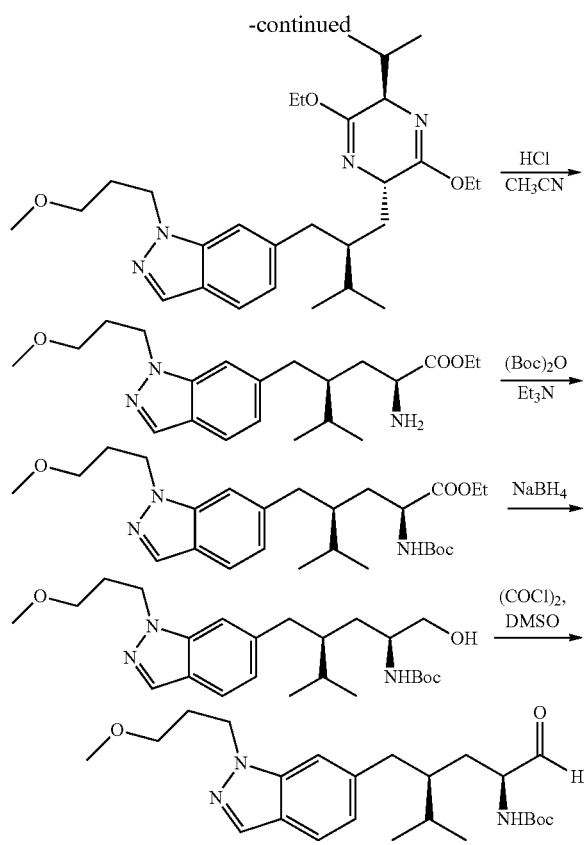

Step 1. Methyl 1-(3-methoxypropyl)-1H-indazole-6-carboxylate

To a solution of 6-iodo-1-(3-methoxypropyl)-1H-indazole (2.0 g, 6.3 mmol) in CH$_3$CN (12 mL) were added Et$_3$N (1.5 mL) and MeOH (5 mL). CO gas was bubbed into the solution. The reaction mixture was stirred at 65° C. under 50 psi of CO for 15 h. The solvent was removed in vacuo and the residue was partitioned between water and EtOAc. The organic layers were washed with H$_2$O and brine, dried over Na$_2$SO$_4$, and evaporated to afford methyl 1-(3-methoxypropyl)-1H-indazole-6-carboxylate (1.3 g, 83%). $^1$H NMR (400 MHz, CDCl$_3$): 2.19 (m, 2H), 3.27 (m, 2H), 3.31 (s, 3H), 3.97 (s, 3H), 4.56 (t, 2H), 7.79 (m, 2H), 8.05 (m, 1H), 8.25 (m, 1H)

Step 2. (1-(3-Methoxypropyl)-1H-indazol-6-yl)methanol

To a solution of methyl 1-(3-methoxypropyl)-1H-indazole-6-carboxylate (1.26 g, 5 mmol) in MeOH (15 mL), NaBH$_4$ (1.52 g, 40 mmol) was added in portions such that the temperature remained below 40° C. The mixture was stirred at rt for 12 h. TLC showed the starting material had been consumed. The solvent was removed in vacuo and the residue was partitioned between water and EtOAc. The organic layers were washed with H$_2$O and brine, dried over Na$_2$SO$_4$, and evaporated to produce (1-(3-methoxypropyl)-1H-indazol-6-yl)methanol (1.05 g, 95%), which was used in the next step without purification.

Step 3. 6-(Bromomethyl)-1-(3-methoxypropyl)-1H-indazole

To a solution of (1-(3-methoxypropyl)-1H-indazol-6-yl)methanol (660 mg, 3 mmol) in dry CH$_2$Cl$_2$ (15 mL) at 0° C., Ph$_3$P (943 mg, 3.6 mmol) and NBS (640 mg, 3.6 mmol) were added in portions. After stirring for 12 h at rt, the mixture was evaporated and the residue was purified by flash chromatography on silica gel to give 6-(bromomethyl)-1-(3-methoxypropyl)-1H-indazole (420 mg, 50%). $^1$H NMR (400 MHz, CDCl$_3$): 2.18 (m, 2H), 3.26 (m, 2H), 3.31 (s, 3H), 4.49 (m, 2H), 4.65 (s, 2H), 7.18 (m, 1H), 7.48 (s,1H), 7.79 (m,1H), 7.99 (m,1H)

Step 4. (R)-4-Benzyl-3-((R)-2-((1-(3-methoxypropyl)-1H-indazol-6-yl)methyl)-3-methylbutanoyl)oxazolidin-2-one To a stirred solution of hexamethyldisilazane (200 mg, 1.24 mmol) in anhydrous THF (2 mL) cooled to −78° C. under N$_2$ was added dropwise 2.5 M n-BuLi (0.5 mL, 1.25 mol) over 30 min. After stirring for an additional 30 min, a solution of (R)-4-benzyl-3-(3-methylbutanoyl)oxazolidin-2-one (313 mg, 1.2 mmol) in THF (2 mL) was added dropwise to the reaction mixture. The mixture was stirred at −78° C. for 2 h and a solution of 6-(bromomethyl)-1-(3-methoxypropyl)-1H-indazole (300 mg, 1.1 mmol) in THF (2 mL) was added. The mixture was allowed to warm from −78° C. to 0° C. over 2 h and stirred at it for 18 h. 10% aq NH$_4$Cl was added and the mixture was extracted with EtOAc (3×10 mL). The combined organic layers were washed with brine, dried over Na$_2$SO$_4$, and concentrated. The residue was purified by flash chromatography on silica gel to give (R)-4-benzyl-3-((R)-2-((1-(3-methoxypropyl)-1H-indazol-6-yl)methyl)-3-methylbutanoyl)-oxazolidin-2-one (250 mg, 49%). $^1$H NMR (400 MHz, CDCl$_3$): 1.09 (m, 6H), 1.96 (m, 1H), 2.09 (m, 3H), 2.61 (m, 1H), 3.12 (m, 2H), 3.22 (m, 2H), 3.29 (s, 3H), 3.89 (m, 1H), 4.02 (m, 1H), 4.35 (m, 1H), 4.40 (m, 1H), 4.59 (m, 1H), 6.75 (m, 2H), 7.07 (m, 3H), 7.13 (m, 1H), 7.26 (m, 1H), 7.33 (m, 1H), 7.61 (m, 1H), 7.91 (m, 1H); MS: 464 (M$^+$+1)

Step 5. (R)-2-((1-(3-Methoxypropyl)-1H-indazol-6-yl)methyl)-3-methylbutanoic acid To a solution of (R)-4-benzyl-3-((R)-2-((1-(3-methoxypropyl)-1H-indazol-6-yl)methyl)-3-methylbutanoyl)oxazolidin-2-one (230 mg, 0.5 mmol) in 3:1 THF/H$_2$O (8 mL) cooled in an ice-water bath, were added 30% aq H$_2$O$_2$ (0.5 mL, 3.5 mmol) and LiOH (60 mg, 1.1 mmol). The mixture was stirred at rt for 12 h. The mixture was cooled to 0° C. and 10% aq Na$_2$SO$_3$ (5 mL) was added dropwise. The solvent was removed in vacuo and the aqueous phase was washed with Et$_2$O. The pH of the aqueous layer was adjusted to 3 by addition of 1 N aq HCl. The mixture was extracted with CH$_2$Cl$_2$ (3×10 mL). The combined organic layers were washed with brine, dried over Na$_2$SO$_4$, and evaporated to give (R)-2-((1-(3-methoxypropyl)-1H-indazol-6-yl)methyl)-3-methylbutanoic acid (123 mg, 81%). $^1$H NMR (400 MHz, CDCl$_3$): 1.07 (m, 6H), 1.99 (m, 1H), 2.56 (m, 1H), 3.00 (m, 2H), 3.24 (m, 2H), 2.99 (s, 3H), 4.10 (m, 1H), 4.40 (m, 2H), 6.98 (m, 1H), 7.23 (m, 1H), 7.59 (m, 1H), 7.92 (m, 1H). MS: 305 (M$^+$+1)

Step 6. (R)-2-((1-(3-Methoxypropyl)-1H-indazol-6-yl)methyl)-3-methylbutan-1-ol To a stirred suspension of LiAlH$_4$ (40 mg, 1 mmol) in anhydrous THF (2 mL) under N$_2$ at −78° C. was added dropwise a solution of (R)-2-((1-(3-methoxypropyl)-1H-indazol-6-yl)methyl)-3-methylbutanoic acid (150 mg, 0.5 mmol) in anhydrous THF (1 mL). The mixture was allowed to warm to rt and stirred for 24 h. TLC showed the starting material had been consumed. The mixture was cooled to 0° C., H₂O (40 uL) was added dropwise, followed by 10% aq NaOH (40 uL). The mixture was filtered and the filtrate was evaporated. The residue was partitioned between EtOAc and water, and extracted with EtOAc (3×10 mL). The combined organic layers were washed with brine, dried over Na₂SO₄, filtered and evaporated to give (R)-2-((1-(3-methoxypropyl)-1H-indazol-6-yl)methyl)-3-methylbutan-1-ol (115 mg, 79%). ¹H NMR (400 MHz, CDCl₃): 1.00 (m, 6H), 1.72 (m, 3H), 2.16 (m, 2H), 2.68 (m, 1H), 2.88 (m, 1H), 3.27 (m, 2H), 3.29 (s, 3H), 3.58 (m, 2H), 4.48 (m, 2H), 7.00 (m, 1H), 7.23 (m, 1H), 7.62 (m, 1H), 7.96 (m, 1H); MS: 291 (M⁺+1)

Step 7. (R)-6-(2-(Bromomethyl)-3-methylbutyl)-1-(3-methoxypropyl)-1H-indazole

To a solution of (R)-2-((1-(3-methoxypropyl)-1H-indazol-6-yl)methyl)-3-methylbutan-1-ol (100 mg, 0.3 mmol) in dry CH₂Cl₂ (3 mL) at 0° C., Ph₃P (140 mg, 0.6 mmol) and NBS (95 mg, 0.6 mmol) were added in portions. After stirring for 12 h at rt, the mixture was evaporated and the residue was purified by flash chromatography on silica gel to afford (R)-6-(2-(bromomethyl)-3-methylbutyl)-1-(3-methoxypropyl)-1H-indazole (70 mg, 62%). ¹H NMR (400 MHz, CDCl₃): 1.02 (m, 6H), 1.74 (m, 1H), 1.89 (m, 1H), 2.17 (m, 2H), 2.71 (m, 1H), 2.95 (m, 1H), 3.32 (s, 3H), 3.43 (m, 1H), 4.45 (m, 2H), 6.98 (d, 1H), 7.27 (s, 1H), 7.63 (d, 1H), 7.95 (s, 1H); MS: 432 (M⁺+1)

Step 8. 6-((S)-2-(((2S,5R)-3,6-Diethoxy-5-isopropyl-2,5-dihydropyrazin-2-yl)methyl)-3-methylbutyl)-1-(3-methoxypropyl)-1H-indazole To a stirred solution of (R)-3,6-diethoxy-2-isopropyl-2,5-dihydropyrazine (480 mg, 2.3 mmol) in anhydrous THF (7 mL) at −78° C. was added dropwise 2.5 M n-BuLi in hexane (0.9 mL, 2.3 mmol). After stirring for 2 h at −78° C., a solution of (R)-6-(2-(bromomethyl)-3-methylbutyl)-1-(3-methoxypropyl)-1H-indazole (530 mg, 1.5 mmol) in THF (2 mL) was added dropwise. The mixture was stirred for 1 h at −78° C., then warmed to rt and stirred for 12 h. The reaction mixture was quenched with satd aq NH₄Cl and extracted with EtOAc (3×10 mL). The combined organic layers were washed with brine, dried over Na₂SO₄, evaporated, and purified by flash chromatography on silica gel to give 6-((S)-2-(((2S,5R)-3,6-diethoxy-5-isopropyl-2,5-dihydropyrazin-2-yl)methyl)-3-methylbutyl)-1-(3-methoxypropyl)-1H-indazole (493 mg, 68%). MS: 485 (M⁺+1).

Step 9. (2S,4S)-Ethyl 2-amino-4-((1-(3-methoxypropyl)-1H-indazol-6-yl)methyl)-5-methylhexanoate To a stirred solution of 6-((S)-2-(((2S,5R)-3,6-diethoxy-5-isopropyl-2,5-dihydropyrazin-2-yl)methyl)-3-methylbutyl)-1-(3-methoxypropyl)-1H-indazole (300 mg, 0.62 mmol) in CH₃CN (5 mL) was added 1 N aq HCl (5 mL) at rt. The mixture was stirred for 5 h, poured into ice-cold, satd aq NaHCO₃ and extracted with CH₂Cl₂ (3×20 mL). The combined organic extracts were washed with brine, dried over Na₂SO₄ and evaporated to give (2S,4S)-ethyl 2-amino-4-((1-(3-methoxypropyl)-1H-indazol-6-yl)methyl)-5-methylhexanoate (220 mg, 95%).

Step 10. (2S,4S)-Ethyl 2-(tert-butoxycarbonylamino)-4-((1-(3-methoxypropyl)-1H-indazol-6-yl)methyl)-5-methylhexanoate To a solution of (2S,4S)-ethyl 2-amino-4-((1-(3-methoxypropyl)-1H-indazol-6-yl)methyl)-5-methylhexanoate (450 mg, 1.2 mmol) in CH₂Cl₂ (10 mL) at 0° C. were added Et₃N (182 mg, 0.18 mmol) and a solution of (Boc)₂O (0.37 g, 1.7 mmol) in CH₂Cl₂ (2 ml). The mixture was stirred for 20 h at rt. Evaporation and flash chromatography on silica gel afforded (2S,4S)-ethyl 2-(tert-butoxycarbonylamino)-4-((1-(3-methoxypropyl)-1H-indazol-6-yl)methyl)-5-methylhexanoate (550 mg, 97%). ¹H NMR: 0.86 (m, 6H), 1.24 (m, 4H), 1.45 (s, 9H), 1.61 (m, 4H), 1.76 (m, 2H), 2.17 (m, 2H), 2.65 (m, 2H), 2.87 (m, 1H), 3.30 (s, 3H), 4.13 (m, 2H), 4.39 (m, 1H), 4.44 (m, 2H), 4.91 m,1H), 6.98 (d, 1H), 7.22 (s, 1H), 7.59 (d, 1H), 7.93 (s, 1H); MS: 476 (M⁺+1)

Step 11. tert-Butyl (2S,4S)-1-hydroxy-4-((1-(3-methoxypropyl)-1H-indazol-6-yl)methyl)-5-methylhexan-2-ylcarbamate To a mixture of (2S,4S)-ethyl 2-(tert-butoxycarbonylamino)-4-((1-(3-methoxypropyl)-1H-indazol-6-yl)methyl)-5-methylhexanoate (7.2 g, 15.2 mmol) in EtOH (100 mL) was added NaBH₄ (5.0 g, 131 mmol) in portions such that the temperature remained lower than 40° C. The mixture was stirred at rt for 12 h. TLC showed the starting material had been consumed. The solvent was removed in vacuo and the residue was partitioned between water and EtOAc. The organic layer was washed with H₂O and brine, dried over Na₂SO₄, and evaporated to produce tert-butyl (2S,4S)-1-hydroxy-4-((1-(3-methoxypropyl)-1H-indazol-6-yl)methyl)-5-methylhexan-2-ylcarbamate (5.8 g, 88%). MS: 434 (M⁺+1)

Step 12. tert-Butyl (2S,4S)-4-((1-(3-methoxypropyl)-1H-indazol-6-yl)methyl)-5-methyl-1-oxohexan-2-ylcarbamate To a solution of oxalyl chloride (0.25 mL, 2.6 mmol) in anhydrous CH₂Cl₂ (15 mL) was added a solution of DMSO (0.4 mL, 5.2 mmol) in anhydrous CH₂Cl₂ (2 mL) dropwise under N₂ at −50° C. to −60° C. After 45 min a solution of tert-butyl (2S,4S)-1-hydroxy-4-((1-(3-methoxypropyl)-1H-indazol-6-yl)methyl)-5-methylhexan-2-ylcarbamate (860 mg, 2 mmol) in CH₂Cl₂ (2 mL) was added dropwise. The mixture was stirred for 1 h and Et₃N (1.7 mL, 10 mmol) was added. The mixture was allowed to warm to rt and satd aq NaHCO₃ (20 mL) was added. The organic layer was separated, and the aqueous layer was extracted with CH₂Cl₂. The combined organic layers were washed with brine, dried over Na₂SO₄, concentrated and purified by flash chromatography on silica gel to afford tert-butyl (2S,4S)-4-((1-(3-methoxypropyl)-1H-indazol-6-ypmethyl)-5-methyl-1-oxohexan-2-ylcarbamate (733 mg, 85%); MS: 432 (M⁺+1)

Preparation 3

(4S,5R)-tert-butyl 5-((2,2-dimethylhexanamido)methyl)-4-((S)-2-formyl-3-methylbutyl)-2,2-dimethyloxazolidine-3-carboxylate

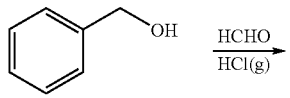

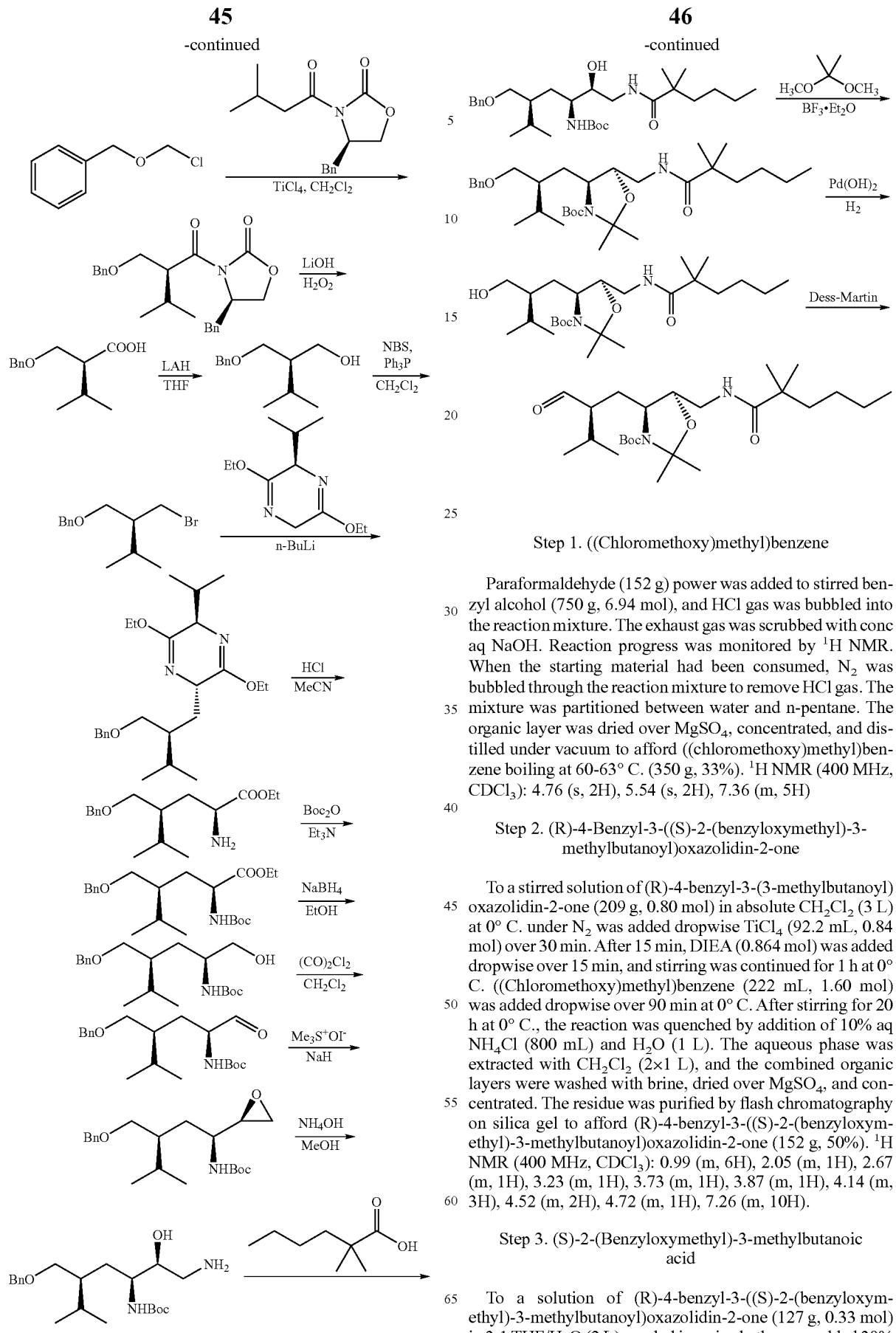

Step 1. ((Chloromethoxy)methyl)benzene

Paraformaldehyde (152 g) power was added to stirred benzyl alcohol (750 g, 6.94 mol), and HCl gas was bubbled into the reaction mixture. The exhaust gas was scrubbed with conc aq NaOH. Reaction progress was monitored by $^1$H NMR. When the starting material had been consumed, $N_2$ was bubbled through the reaction mixture to remove HCl gas. The mixture was partitioned between water and n-pentane. The organic layer was dried over $MgSO_4$, concentrated, and distilled under vacuum to afford ((chloromethoxy)methyl)benzene boiling at 60-63° C. (350 g, 33%). $^1$H NMR (400 MHz, $CDCl_3$): 4.76 (s, 2H), 5.54 (s, 2H), 7.36 (m, 5H)

Step 2. (R)-4-Benzyl-3-((S)-2-(benzyloxymethyl)-3-methylbutanoyl)oxazolidin-2-one To a stirred solution of (R)-4-benzyl-3-(3-methylbutanoyl) oxazolidin-2-one (209 g, 0.80 mol) in absolute $CH_2Cl_2$ (3 L) at 0° C. under $N_2$ was added dropwise $TiCl_4$ (92.2 mL, 0.84 mol) over 30 min. After 15 min, DIEA (0.864 mol) was added dropwise over 15 min, and stirring was continued for 1 h at 0° C. ((Chloromethoxy)methyl)benzene (222 mL, 1.60 mol) was added dropwise over 90 min at 0° C. After stirring for 20 h at 0° C., the reaction was quenched by addition of 10% aq $NH_4Cl$ (800 mL) and $H_2O$ (1 L). The aqueous phase was extracted with $CH_2Cl_2$ (2×1 L), and the combined organic layers were washed with brine, dried over $MgSO_4$, and concentrated. The residue was purified by flash chromatography on silica gel to afford (R)-4-benzyl-3-((S)-2-(benzyloxymethyl)-3-methylbutanoyl)oxazolidin-2-one (152 g, 50%). $^1$H NMR (400 MHz, $CDCl_3$): 0.99 (m, 6H), 2.05 (m, 1H), 2.67 (m, 1H), 3.23 (m, 1H), 3.73 (m, 1H), 3.87 (m, 1H), 4.14 (m, 3H), 4.52 (m, 2H), 4.72 (m, 1H), 7.26 (m, 10H).

Step 3. (S)-2-(Benzyloxymethyl)-3-methylbutanoic acid

To a solution of (R)-4-benzyl-3-((S)-2-(benzyloxymethyl)-3-methylbutanoyl)oxazolidin-2-one (127 g, 0.33 mol) in 3:1 THF/$H_2O$ (2 L), cooled in an ice bath, were added 30% aq H$_2$O$_2$ (235 mL, 2.07 mol) and LiOH (28 g, 0.66 mol). The mixture was stirred at 20° C. for 3 h, followed by cooling to 0° C. Then 1.5 M aq Na$_2$SO$_3$ (1.38 L, 3.83 mol) was added dropwise within 30 min. After addition of satd aq NaHCO$_3$ (500 mL), volatiles were evaporated, and the aqueous phase was washed with Et$_2$O (3×600 mL). The organic layers were discarded. The aqueous layer was adjusted to pH 3 by adding 2 N aq HCl and extracted with CH$_2$Cl$_2$ (3×800 mL). The combined organic layers were washed with satd aq NaCl (1 L), dried over Na$_2$SO$_4$, and evaporated to give (S)-2-(benzyloxymethyl)-3-methylbutanoic acid (60 g, 82%). $^1$H NMR (400 MHz, CDCl$_3$): 0.98 (m, 6H), 2.01 (m, 1H), 2.53 (m, 1H), 3.67 (m, 2H), 4.55 (s, 2H), 7.30 (m, 6H)

Step 4. (R)-2-(Benzyloxymethyl)-3-methylbutan-1-ol

To a stirred suspension solution of LiAlH$_4$ (28.5 g, 0.75 mol) in anhydrous THF (1 L) at 0° C. under N$_2$ was added dropwise over 30 min a solution of (S)-2-(benzyloxymethyl)-3-methylbutanoic acid (66 g, 0.30 mol) in anhydrous THF (500 mL). The reaction mixture was warmed to rt and stirred overnight. After the mixture was cooled to 0° C., water (29 mL) was added dropwise, followed by 10% aq NaOH (29 mL). The mixture was filtered and the filtrate was evaporated. The residue was partitioned between EtOAc and water and extracted with EtOAc (3×). The combined organic layers were washed with brine, dried over Na$_2$SO$_4$, filtered and evaporated to give (R)-2-(benzyloxymethyl)-3-methylbutan-1-ol (54 g, 86%). $^1$H NMR (400 MHz, CDCl$_3$): 0.92 (m, 6H), 1.66 (m, 1H), 1.77 (m, 1H), 2.70 (brs, 1H), 3.59 (m, 4H), 4.51 (m, 2H), 7.30 (m, 5H).

Step 5. (S)-((2-(Bromomethyl)-3-methylbutoxy)methyl)benzene

To a solution of (R)-2-(benzyloxymethyl)-3-methylbutan-1-ol (54 g, 0.26 mol) in dry CH$_2$Cl$_2$ (2 L) at 0° C., Ph$_3$P (88 g, 0.31 mol) and NBS (55.5 g, 0.31 mol) were added in portions. After stirring for 18 h at rt, the mixture was evaporated and the residue was purified by flash chromatography on silica gel to give (S)-((2-(bromomethyl)-3-methylbutoxy)methyl)benzene (43 g, 61%). $^1$H NMR (400 MHz, CDCl$_3$): 0.94 (m, 6H), 1.71 (m, 1H), 1.85 (m, 1H), 3.48 (m, 1H), 3.57 (m, 1H), 3.62 (m, 1H), 3.68 (m, 1H), 4.52 (s, 2H), 7.31 (m, 5H)

Step 6. (2S,5R)-2-((S)-2-(Benzyloxymethyl)-3-methylbutyl)-3,6-diethoxy-5-isopropyl-2,5-dihydropyrazine To a solution of (R)-3,6-diethoxy-2-isopropyl-2,5-dihydropyrazine (15.4 g, 0.084 mol) in anhydrous THF (250 mL) at −78° C. was added dropwise 2.5 M n-BuLi in hexanes (34 mL, 0.085 mol) over 45 min. After stirring for 30 min at −78° C., a solution of (S)-((2-(bromomethyl)-3-methylbutoxy)methyl)benzene (15.6 g, 0.056 mol) in THF (100 L) was added dropwise over 30 min. The mixture was stirred for 2 h at −78° C. and then at −20° C. for 18 h. After evaporation, the residue was partitioned between H$_2$O (200 mL) and EtOAc (3×200 mL). The combined organic layers were washed with brine (0.5 L), dried over MgSO$_4$, evaporated, and purified by flash chromatography on silica gel eluting with 1:25 EtOAc/hexane to give (2S,5R)-2-((S)-2-(benzyloxymethyl)-3-methylbutyl)-3,6-diethoxy-5-isopropyl-2,5-dihydropyrazine (18.5 g, 80%). $^1$H NMR (400 MHz, CDCl$_3$): δ8.00 (s, 1H), 7.34-7.24 (m, 5H), 4.50 (s, 2H), 4.03 (m, 1H), 3.93 (m, 1H), 3.72 (s, 3H), 3.62 (s, 3H), 3.54-3.42 (m, 2H), 2.27 (m, 1H), 1.94-1.88 (m, 1H), 1.80-1.61 (m, 1H), 1.47-1.42 (m, 1H), 1.05 (d, J=6.4 Hz, 3H), 0.88 (d, J=6.4 Hz, 3H), 0.80 (d, J=6.4 Hz, 3H), 0.68 (d, J=6.4 Hz, 3H); MS: 403 (M$^+$+1).

Step 7. (2S,4S)-Ethyl 2-amino-4-(benzyloxymethyl)-5-methylhexanoate

To a solution of (2S,5R)-2-((S)-2-(benzyloxymethyl)-3-methylbutyl)-3,6-diethoxy-5-isopropyl-2,5-dihydropyrazine (17.5 g, 46.8 mmol) in CH$_3$CN (187 mL) was added 1 N aq HCl (187 mL, 187.2 mol) at rt and stirring was continued for 1.5 h. The mixture was poured into ice-cold, satd aq NaHCO$_3$ and extracted with EtOAc (3×200 mL). The combined organic layers were washed with brine, dried and evaporated to afford (2S,4S)-ethyl 2-amino-4-(benzyloxymethyl)-5-methylhexanoate as a pale yellow oil (13.5 g) which was used in the next step without purification.

Step 8. (2S,4S)-Ethyl 4-(benzyloxymethyl)-2-(tert-butoxycarbonylamino)-5-methylhexanoate To a stirred solution of the (2S,4S)-ethyl 2-amino-4-(benzyloxymethyl)-5-methylhexanoate (13.5 g, 48.4 mmol) in CH$_2$Cl$_2$ (150 mL) at 0° C. were added Et$_3$N (10 mL, 72.6 mmol) and a solution of Boc$_2$O (12.7 g, 58.1 mmol) in CH$_2$Cl$_2$ (80 mL). The mixture was stirred for 20 h at rt. Evaporation and flash chromatography on silica gel afforded (2S,4S)-ethyl 4-(benzyloxymethyl)-2-(tert-butoxycarbonylamino)-5-methylhexanoate (15.2 g, 82% for two steps). $^1$H NMR (400 MHz, CDCl$_3$): δ7.35-7.27 (m, 5H), 4.95 (brs, 1H), 4.51 (d, J=4 Hz, 2H), 4.32 (m, 1H), 3.71 (s, 3H), 3.48-3.40 (m, 2H), 1.78-1.60 (m, 4H), 1.42 (s, 9H), 0.85-0.82 (m, 6H). MS: 394 (M$^+$+1).

Step 9. tert-Butyl (2S,4S)-4-(benzyloxymethyl)-1-hydroxy-5-methylhexan-2-ylcarbamate To a solution of (2S,4S)-ethyl 4-(benzyloxymethyl)-2-(tert-butoxycarbonylamino)-5-methylhexanoate (16 g, 42.2 mmol) in EtOH (200 mL) at rt was added NaBH$_4$ (12.8 g, 0.338 mol) in portions. The mixture was stirred for 16 h. The solvent was evaporated and the residue was partitioned between H$_2$O (300 mL) and EtOAc (3×200 mL). The combined organic extracts were washed with brine, dried over MgSO$_4$ and evaporated to give tert-butyl (2S,4S)-4-(benzyloxymethyl)-1-hydroxy-5-methylhexan-2-ylcarbamate (14.4 g, 97%). $^1$H NMR (400 MHz, CDCl$_3$): δ7.35-7.29 (m, 5H), 4.95 (brs, 1H), 4.50 (s, 2H), 3.62 (brs, 3H), 3.50 (m, 1H), 3.35 (m, 1H), 1.75 (m, 1H), 1.54-1.45 (m, 3H), 1.43 (s, 9H), 0.88 (m, 6H); MS: 352 (M$^+$+1)

Step 10. tert-Butyl (2S,4S)-4-(benzyloxymethyl)-5-methyl-1-oxohexan-2-ylcarbamate A solution of DMSO (7.58 g, 97.2 mmol) in anhydrous CH$_2$Cl$_2$ (100 mL) was added dropwise to a stirred solution of oxalyl chloride (4.2 mL, 48.6 mmol) in anhydrous CH$_2$Cl$_2$ (150 mL) under N$_2$ at −50° C. to −60° C. After 15 min, tert-butyl (2S,4S)-4-(benzyloxymethyl)-1-hydroxy-5-methylhexan-2-ylcarbamate (14.2 g, 40.5 mmol) in CH$_2$Cl$_2$ (100 mL) was added dropwise over 30 min, and stirred for about 60 min. Triethylamine (27 mL, 203 mmol) was added and the mixture was stirred overnight. Water was added, the organic layer was separated, and the aqueous layer was extracted with CH$_2$Cl$_2$. The combined organic layers were washed with 5% aq Na$_2$CO$_3$ and brine, dried over Na$_2$SO$_4$ and evaporated. The residue was purified by flash chromatography on silica gel to give tert-butyl (2S,4S)-4-(benzyloxymethyl)-5-methyl-1-oxohexan-2-ylcarbamate (14 g, 99%), which was used for next step without purification; MS: 350 (M$^+$+1).

Step 11. tert-Butyl (1S,3S)-3-(benzyloxymethyl)-4-methyl-1-((R)-oxiran-2-yl)pentylcarbamate A flame dried 250-mL, round-bottom flask was charged with sodium hydride (2.4 g, 60.0 mmol) and trimethyloxosulfonium iodide (13.2 g, 60 mmol). The flask was evacuated and refilled with N$_2$, and dry DMSO (100 mL) was added. The mixture was stirred at rt for 1 h to afford a solution. A second 500-mL, round-bottom flask was charged with tert-butyl (2S,4S)-4-(benzyloxymethyl)-5-methyl-1-oxohexan-2-ylcarbamate (14 g, 40 mmol) and THF (150 mL). The flask was evacuated and refilled with N$_2$, and the sulfur ylid solution prepared above was added through a cannula. The resulting mixture was stirred for 1 h at rt. The reaction mixture was quenched with brine and extracted with EtOAc (3×200 mL). The combined organic phases were dried over Na$_2$SO$_4$, filtered and concentrated in vacuo. The residue was purified by column chromatography on silica gel to afford tert-butyl (1S, 3S)-3-(benzyloxymethyl)-4-methyl-1-((R)-oxiran-2-yl)pentylcarbamate (7.2 g, 50%). $^1$H NMR (400 MHz, CD$_3$OD): δ 8.00 (s, 1H), 7.74 (d, J=8.4 Hz, 1H), 7.55 (m, 1H), 7.17 (m, 1H), 4.50 (m, 2H), 3.84-3.68 (m, 2H), 3.45 (m, 1H), 3.27 (s, 3H), 3.25-3.18 (m, 3H), 2.13 (m, 2H), 1.89-1.72 (m, 2H), 1.55 (m, 3H), 1.32-1.11 (m, 9H), 0.99-0.80 (m, 12H); MS: 364 (M$^+$+1)

Step 12. tert-Butyl (2S,3S,5S)-1-amino-5-(benzyloxymethyl)-2-hydroxy-6-methylheptan-3-ylcarbamate To a solution of tert-butyl (1S,3S)-3-(benzyloxymethyl)-4-methyl-1-((R)-oxiran-2-yl)pentylcarbamate (500 mg, 1.38 mmol) in MeOH (5 mL), was added NH$_4$OH (5 mL). The mixture was stirred at rt for 18 h. The mixture was concentrated in vacuo to give tert-butyl (2S,3S,5S)-1-amino-5-(benzyloxymethyl)-2-hydroxy-6-methylheptan-3-ylcarbamate (510 mg, 97.3%). $^1$H NMR (400 MHz, CD$_3$OD): 0.86 (m, 6H), 1.41 (s, 12H), 1.82 (brs, 1H), 2.50 (m, 1H), 3.42 (m, 2H), 3.61 (m, 2H), 3.71 (m, 3H), 3.90 (m, 4H), 6.61 (m, 1H), 7.31 (m, 5H), 7.71 (m, 1H); MS: 381 (M$^+$+1)

Step 13. tert-Butyl (2S,3S,5S)-5-(benzyloxymethyl)-1-(2,2-dimethylhexanamido)-2-hydroxy-6-methylheptan-3-ylcarbamate To a solution of tert-butyl (2S,3S,5S)-1-amino-5-(benzyloxymethyl)-2-hydroxy-6-methylheptan-3-ylcarbamate (500 mg, 1.32 mmol) in CH$_2$Cl$_2$ (15 mL), were added 2,2-dimethylhexanoic acid (220 mg, 1.45 mmol), HOBt (360 mg, 2.65 mmol) and EDCl (500 mg, 2.65 mmol). The mixture was cooled to 0° C. and DIEA (850 mg, 6.6 mmol) was added. The resulting mixture was allowed to warm to rt and stirred for 5 h. The reaction mixture was washed with water and brine, dried over Na$_2$SO4, filtered and concentrated in vacuo to give crude product, which was purified by column chromatography on silica gel to produce tert-butyl (2S,3S,5S)-5-(benzyloxymethyl)-1-(2,2-dimethylhexanamido)-2-hydroxy-6-methylheptan-3-ylcarbamate (310 mg, 46%); MS: 507 (M$^+$+1)

Step 14. (4S,5R)-tert-Butyl 4-((S)-2-(benzyloxymethyl)-3-methylbutyl)-5-((2,2-dimethylhexanamido) methyl)-2,2-dimethyloxazolidine-3-carboxylate To a solution of tert-butyl (2S,3S,5S)-5-(benzyloxymethyl)-1-(2,2-dimethylhexanamido)-2-hydroxy-6-methylheptan-3-ylcarbamate (3.8 g, 7.5 mmol) in acetone (50 mL) was added 2,2-dimethoxy-propane (6.0 g, 57.7 mmol). The resulting mixture was cooled to 0° C., BF$_3$Et$_2$O (100 mg, 0.7 mmol) was added. The reaction mixture was allowed to warm to rt and stirred for 2 h. TLC showed the starting material had been consumed. The reaction mixture was quenched with Et$_3$N. The solvent was removed in vacuo and the residue was partitioned between water and EtOAc. The organic layers were washed with H$_2$O and brine, dried over Na$_2$SO$_4$, and evaporated to produce (4S,5R)-tert-butyl 4-((S)-2-(benzyloxymethyl)-3-methylbutyl)-5-((2,2-dimethylhexanamido) methyl)-2,2-dimethyloxazolidine-3-carboxylate (3.0 g, 73%); MS: 547 (M$^+$+1).

Step 15. (4S,5R)-tert-Butyl 5-((2,2-dimethylhexanamido)methyl)-4-((S)-2-(hydroxymethyl)-3-methylbutyl)-2,2-dimethyloxazolidine-3-carboxylate (4S,5R)-tert-Butyl 4-((S)-2-(benzyloxymethyl)-3-methylbutyl)-5-((2,2-dimethylhexanamido)methyl)-2,2-dimethyloxazolidine-3-carboxylate (3.0 g, 5.5 mol) was dissolved in EtOH (30 mL) and Pd(OH)$_2$/C (300 mg) was added. The reaction mixture was stirred under an atmosphere of hydrogen at rt for about 3-4 h. TLC showed the starting material had been consumed. The reaction mixture was filtered and the filtrate was concentrated under reduced pressure to give (4S, 5R)-tert-butyl 5-((2,2-dimethylhexanamido)methyl)-4-((S)-2-(hydroxymethyl)-3-methylbutyl)-2,2-dimethyloxazolidine-3-carboxylate (2.40 g, 96%) which was used in the next step without purification. $^1$H NMR (400 MHz, CDCl$_3$): 0.87 (m, 6H), 1.16 (m, 6H), 1.47 (s, 9H), 1.59 (s, 1H), 2.16 (m, 1H), 2.88 (m, 1H), 3.49 (m, 1H), 3.98 (m, 1H); MS: 457 (M$^+$+1)

Step 16. (4S,5R)-tert-Butyl 5-((2,2-dimethylhexanamido)methyl)-4-((S)-2-formyl-3-methylbutyl)-2,2-dimethyloxazolidine-3-carboxylate To a solution of (4S,5R)-tert-butyl 5-((2,2-dimethylhexanamido)methyl)-4-((S)-2-(hydroxymethyl)-3-methylbutyl)-2,2-dimethyloxazolidine-3-carboxylate (100 mg, 0.22 mmol) in anhydrous CH$_2$Cl$_2$ (5 mL) was added Dess-Martin reagent (120 mg, 0.283 mmol). The reaction mixture was stirred at rt for 5 h. The reaction mixture was filtered and the filtrate was concentrated under reduced pressure to (4S,5R)-tert-butyl 5-((2,2-dimethylhexanamido)methyl)-4-((S)-2-formyl-3-methylbutyl)-2,2-dimethyloxazolidine-3-carboxylate (80 mg, 80%), which was used without purification; MS: 455 (M$^+$+1).

EXAMPLE 1

N-((2S,3S,5S)-3-amino-2-hydroxy-5-((1-(3-methoxypropyl)-1H-indazol-6-yl)methyl)-6-methylheptyl)-2,2-dimethylhexanamide (I-1A)

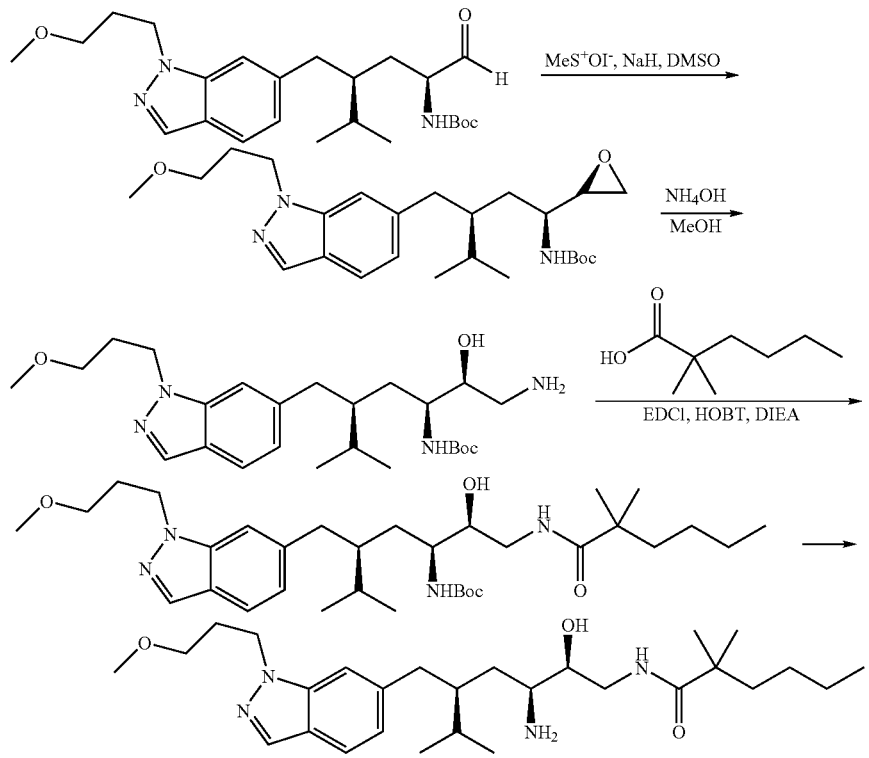

Step 1. tert-Butyl (1S,3S)-3-((1-(3-methoxypropyl)-1H-indazol-6-yl)methyl)-4-methyl-1-((S)-oxiran-2-yl)pentylcarbamate A flame dried 100-mL, round-bottom flask was charged with sodium hydride (1.45 g, 60.0 mmol) and trimethyloxosulfonium iodide (8.0 g, 36 mmol). The flask was evacuated and refilled with N$_2$, and dry DMSO (50 mL) was added. The mixture was stirred at rt for 2 h to give a solution of the sulfur ylid. A second 100-mL, round-bottom flask was charged with tert-butyl (2S,4S)-4-((1-(3-methoxypropyl)-1H-indazol-6-yl)methyl)-5-methyl-1-oxohexan-2-ylcarbamate (830 mg, 1.92 mmol) and THF (10 mL). The flask was evacuated and refilled with N$_2$, and the sulfur ylid solution (6.0 mL) was added through a cannula. The resulting mixture was stirred for 2-3 h at rt. The reaction mixture was quenched with brine and extracted with ethyl acetate (3×25 mL). The combined organic phases were dried over Na$_2$SO$_4$, filtered and concentrated in vacuo. The residue was purified by chromatography to afford tert-butyl (1S,3S)-3-((1-(3-methoxypropyl)-1H-indazol-6-yl)methyl)-4-methyl-1-((S)-oxiran-2-yl)pentylcarbamate (410 mg, 48%). $^1$H NMR (400 MHz, CDCl$_3$): 0.81-0.92 (m, 5H), 1.26 (m, 2H), 1.47 (s, 6H), 1.65 (m, 6H), 2.17 (m, 2H), 2.68 (m, 1H), 2.95 (m, 1H), 3.30 (s, 3H), 4.11 (m, 1H), 4.47 (m, 2H), 6.99 (m, 1H), 7.21 (m, 1H), 7.60 (m, 1H), 7.95 (m, 1H); MS: 446 (M$^+$+1)

Step 2. tert-Butyl (2S,3S,5S)-1-amino-2-hydroxy-5-((1-(3-methoxypropyl)-1H-indazol-6-yl)methyl)-6-methylheptan-3-ylcarbamate To a solution of tert-butyl (1S,3S)-3-((1-(3-methoxypropyl)-1H-indazol-6-yl)methyl)-4-methyl-1-((S)-oxiran-2-yl)pentylcarbamate (400 mg, 0.9 mmol) in MeOH (5 mL), NH$_4$OH (5 mL) was added dropwise. The reaction mixture was stirred at rt for 18 h. The mixture was concentrated in vacuo to give tert-butyl (2S,3S,5S)-1-amino-2-hydroxy-5-((1-(3-methoxypropyl)-1H-indazol-6-yl)methyl)-6-methylheptan-3-ylcarbamate (405 mg, 98%), which was used for next step without further purification. MS: 463 (M$^+$+1)

Step 3. tert-Butyl (2S,3S,5S)-1-(2,2-dimethylhexanamido)-2-hydroxy-5-((1-(3-methoxypropyl)-1H-indazol-6-yl)methyl)-6-methylheptan-3-ylcarbamate To a solution of tert-butyl (2S,3S,5S)-1-amino-2-hydroxy-5-((1-(3-methoxypropyl)-1H-indazol-6-yl)methyl)-6-methylheptan-3-ylcarbamate (350 mg, 0.76 mmol) in CH$_2$Cl$_2$ (15 mL), 2,2-dimethylhexanoic acid (176 mg, 1.22 mmol), HOBt (290 mg, 2.1 mmol) and EDCl (400 mg, 2.1 mmol) were added. The mixture cooled to 0° C. and DIEA (700 mg, 5.4 mmol) was added. The resulting mixture was allowed to warm to rt and stirred for 5 h. The reaction mixture was washed with water and brine, dried over Na$_2$SO$_4$, filtered and concentrated in vacuo to give tert-butyl (2S,3S,5S)-1-(2,2-dimethylhexanamido)-2-hydroxy-5-((1-(3-methoxypropyl)-1H-indazol-6-yl)methyl)-6-methylheptan-3-ylcarbamate (335 mg, 75%). $^1$H NMR (400 MHz, CDCl$_3$): 0.86 (m, 3H), 0.92 (m, 3H), 0.99 (m, 3H), 1.13 (s, 6H), 1.16 (m, 2H), 1.27 (m, 3H), 1.49 (m, 2H), 1.70 (m, 3H), 1.88 (m, 1H), 2.11 (m, 2H), 2.62 (m, 1H), 2.85 (m, 1H), 2.97 (m, 1H), 3.10 (m, 1H), 3.28 (s, 3H), 3.36 (m, 1H), 3.62 (m, 1H), 4.48 (m, 2H), 7.06 (m, 1H), 7.39 (s, 1H), 7.67 (m, 1H), 7.99 (s, 1H); MS: 588 (M⁺+1)

Step 4. N-((2S,3S,5S)-3-Amino-2-hydroxy-5-((1-(3-methoxypropyl)-1H-indazol-6-yl)methyl)-6-methylheptyl)-2,2-dimethylhexanamide tert-Butyl (2S,3S,5S)-1-(2,2-dimethylhexanamido)-2-hydroxy-5-((1-(3-methoxypropyl)-1H-indazol-6-yl)methyl)-6-methylheptan-3-ylcarbamate (335 mg, 75%) (83 mg, 0.15 mmol) was dissolved in a solution of 2N HCl in methanol (6 mL) and the reaction mixture was stirred at 40° C. for 2 h. The solvent was removed in vacuo to produce N-((2S,3S,5S)-3-amino-2-hydroxy-5-((1-(3-methoxypropyl)-1H-indazol-6-yl)methyl)-6-methylheptyl)-2,2-dimethylhexanamide (58 mg, 80%). ¹H NMR (400 MHz, CDCl₃): 0.86 (m, 3H), 0.92 (m, 3H), 0.99 (m, 3H), 1.13 (s, 6H), 1.16 (m, 2H), 1.27 (m, 3H), 1.49 (m, 2H), 1.70 (m, 3H), 1.88 (m, 1H), 2.11 (m, 2H), 2.62 (m, 1H), 2.85 (m, 1H), 2.97 (m, 1H), 3.10 (m, 1H), 3.28 (s, 3H), 3.36 (m, 1H), 3.64 (m, 1H), 4.49 (m, 2H), 7.06 (d, 1H), 7.39 (s, 1H), 7.67 (d, 1H), 7.97 (s, 1H); MS: 488 (M+1).

EXAMPLE 2

N-((2R,3S,5S)-2-hydroxy-5-(hydroxy(1-(3-methoxypropyl)-1H-indazol-6-yl)methyl)-3,6-dimethylheptyl)-2,2-dimethylhexanamide (I-2A)

Step 1. (4S,5S)-tert-Butyl 5-((2,2-dimethylhexanamido)methyl)-4-((S)-2-(hydroxy(1-(3-methoxypropyl)-1H-indazol-6-yl)methyl)-3-methylbutyl)-2,2-dimethyloxazolidine-3-carboxylate To a solution of 6-iodo-1-(3-methoxypropyl)-1H-indazole (1.1 g, 3.48 mmol) in anhydrous THF (15 mL) at −78° C. under N₂ was added dropwise n-BuLi (2.5 M in hexanes, 1.4 mL, 3.5 mmol). After stirring at −78° C. for 2 h, the reaction mixture was added through a cannula to a solution of (4S,5S)-tert-butyl 5-((2,2-dimethylhexanamido)methyl)-4-((S)-2-formyl-3-methylbutyl)-2,2-dimethyloxazolidine-3-carboxylate (160 mg, 0.35 mmol) in anhydrous THF (10 mL) at −78° C. The mixture was stirred at this temperature for 2 h, allowed to warm to rt and stirred overnight. Satd aq NH₄Cl (25 mL) was added and the mixture was extracted with EtOAc (3×15 mL). The combined organic extracts were washed with brine, dried over Na₂SO₄ and evaporated. The residue was purified by column chromatography on silica gel to give (4S,5S)-tert-butyl 5-((2,2-dimethylhexanamido)methyl)-4-((S)-2-(hydroxy(1-(3-methoxypropyl)-1H-indazol-6-yl)methyl)-3-methylbutyl)-2,2-dimethyloxazolidine-3-carboxylate (45 mg, 20% yield). MS: 645 (M⁺+1)

Step 2. N-((2R,3S,5S)-2-Hydroxy-5-(hydroxy(1-(3-methoxypropyl)-1H-indazol-6-yl)methyl)-3,6-dimethylheptyl)-2,2-dimethylhexanamide To a stirred solution of (4S,5S)-tert-butyl 5-((2,2-dimethylhexanamido)methyl)-4-((S)-2-(hydroxy(1-(3-methox-

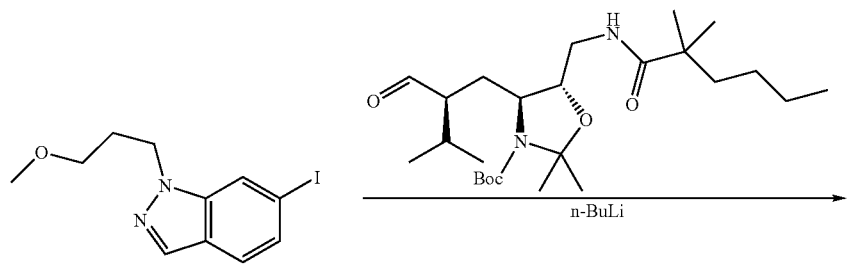

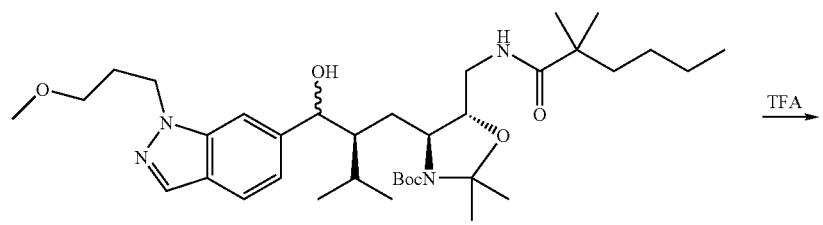

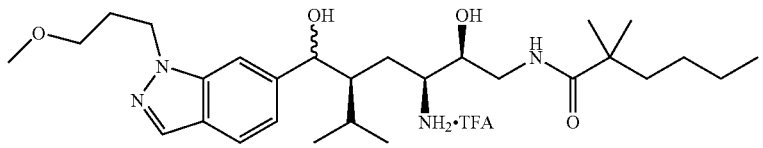

ypropyl)-1H-indazol-6-yl)methyl)-3-methylbutyl)-2,2-dimethyloxazolidine-3-carboxylate (45 mg, 0.07 mmol) in CH$_2$Cl$_2$ (8 mL) at 0° C. was added TFA (2 mL). The mixture was stirred for ~1 h and concentrated. The residue was purified by preparative HPLC to give N-((2S,3S,5S)-3-amino-2-hydroxy-5-(hydroxy(1-(3-methoxypropyl)-1H-indazol-6-yl)methyl)-6-methylheptyl)-2,2-dimethylhexanamide as its TFA salt (15 mg, 42%). $^1$H NMR (400 MHz, CD$_3$OD): δ 8.00 (s, 1H), 7.74 (d, J=8.4 Hz, 1H), 7.55 (m, 1H), 7.17 (m, 1H), 4.50 (m, 2H), 3.84-3.68 (m, 2H), 3.45 (m, 1H), 3.27 (s, 3H), 3.25-3.18 (m, 3H), 2.13 (m, 2H), 1.89-1.72 (m, 2H), 1.55 (m, 3H), 1.32-1.11 (m, 9H), 0.99-0.80 (m, 12H); MS: 489 (M$^+$+1).

EXAMPLE 3

N-((3S,5S)-3-amino-5-((1-(2-cyclopropylethyl)-1H-indazol-6-yl)(hydroxy)methyl)-2-hydroxy-6-methylheptyl)-2,2-dimethylhexanamide (I-3A, I-3B, I-3C, I-3D)

Four isomers of N-((3S,5S)-3-amino-5-((1-(2-cyclopropylethyl)-1H-indazol-6-yl)(hydroxy)methyl)-2-hydroxy-6-methylheptyl)-2,2-dimethylhexanamide were prepared from 1-(2-cyclopropylethyl)-6-iodo-1H-indazole using procedures similar to those described in Example 2. In Step 1, two fractions each containing two isomers of tert-butyl (3S,5S)-5-((1-(2-cyclopropylethyl)-1H-indazol-6-yl)(hydroxy)methyl)-1-(2,2-dimethylhexanamido)-2-hydroxy-6-methylheptan-3-ylcarbamate were separated by preparative HPLC. The first fraction was subjected to the conditions of Step 2 to give two isomeric products which were separated by preparative HPLC and designated I-3A and I-3B. The second fraction was subjected to the conditions of Step 2 to give two isomeric products which were separated by preparative HPLC and designated I-3C and I-3D.

EXAMPLE 4

N-((3S,5S)-3-amino-5-((1-(3-ethoxypropyl)-1H-indazol-6-yl)(hydroxy)methyl)-2-hydroxy-6-methylheptyl)-2,2-dimethylhexanamide (I-4A, I-4B)

Two isomers of N-((3S,5S)-3-amino-5-((1-(3-ethoxypropyl)-1H-indazol-6-yl)(hydroxy)methyl)-2-hydroxy-6-methylheptyl)-2,2-dimethylhexanamide were prepared from 1-(3-ethoxypropyl)-6-iodo-1H-indazole using procedures similar to those described in Example 2. In Step 1, two fractions each containing isomers of tert-butyl (3S,5S)-1-(2,2-dimethylhexanamido)-5-((1-(3-ethoxypropyl)-1H-indazol-6-yl)(hydroxy)methyl)-2-hydroxy-6-methylheptan-3-ylcarbamate were separated by preparative HPLC. The first fraction was subjected to the conditions of Step 2 to give two isomers of N-((3S,5S)-3-amino-5-((1-(3-ethoxypropyl)-1H-indazol-6-yl)(hydroxy)methyl)-2-hydroxy-6-methylheptyl)-2,2-dimethylhexanamide as a mixture which was designated I-4A. The second fraction was subjected to the conditions of Step 2 to give two isomers of N-((3S,5S)-3-amino-5-((1-(3-ethoxypropyl)-1H-indazol-6-yl)(hydroxy)methyl)-2-hydroxy-6-methylheptyl)-2,2-dimethylhexanamide as a mixture which was designated I-4B.

EXAMPLE 5

N-((3S,5S)-3-amino-2-hydroxy-5-(hydroxy(1-(3-isopropoxypropyl)-1H-indazol-6-yl)methyl)-6-methylheptyl)-2,2-dimethylhexanamide (I-5A)

Two isomers of N-((3S,5S)-3-amino-2-hydroxy-5-(hydroxy(1-(3-isopropoxypropyl)-1H-indazol-6-yl)methyl)-6-methylheptyl)-2,2-dimethylhexanamide were prepared from 6-iodo-1-(3-isopropoxypropyl)-1H-indazole using procedures similar to those described in Example 2. In Step 1, two fractions each containing isomers of tert-butyl (3S,5S)-1-(2,2-dimethylhexanamido)-2-hydroxy-5-(hydroxy(1-(3-isopropoxypropyl)-1H-indazol-6-yl)methyl)-6-methylheptan-3-ylcarbamate were separated by preparative HPLC. The first fraction was subjected to the conditions of Step 2 to give two isomers of N-((3S,5S)-3-amino-2-hydroxy-5-(hydroxy(1-(3-isopropoxypropyl)-1H-indazol-6-yl)methyl)-6-methylheptyl)-2,2-dimethylhexanamide as a mixture which was designated I-5A.

EXAMPLE 6

(2S,4S,5S,7S)-5-amino-N-(3-amino-2,2-dimethyl-3-oxopropyl)-4-hydroxy-2-isopropyl-7-((1-(3-methoxypropyl)-1H-indazol-6-yl)methyl)-8-methylnonanamide (I-6A)

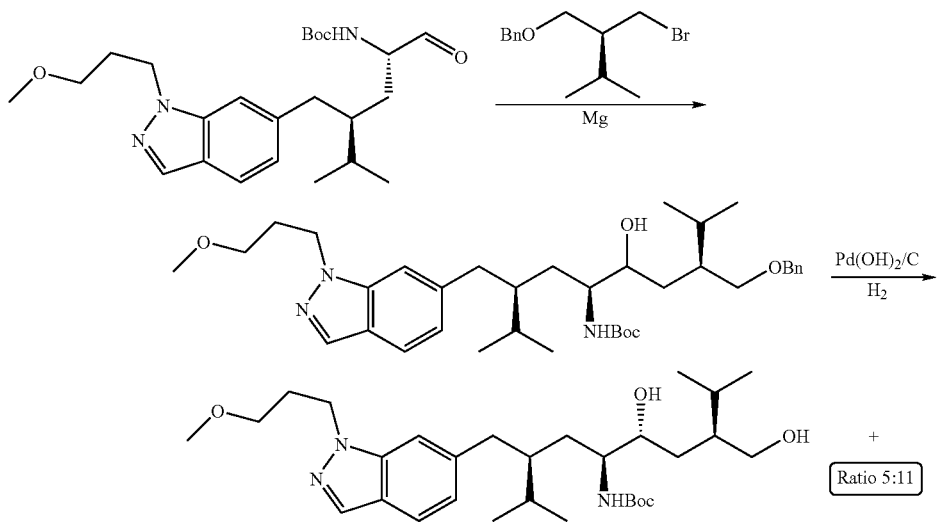

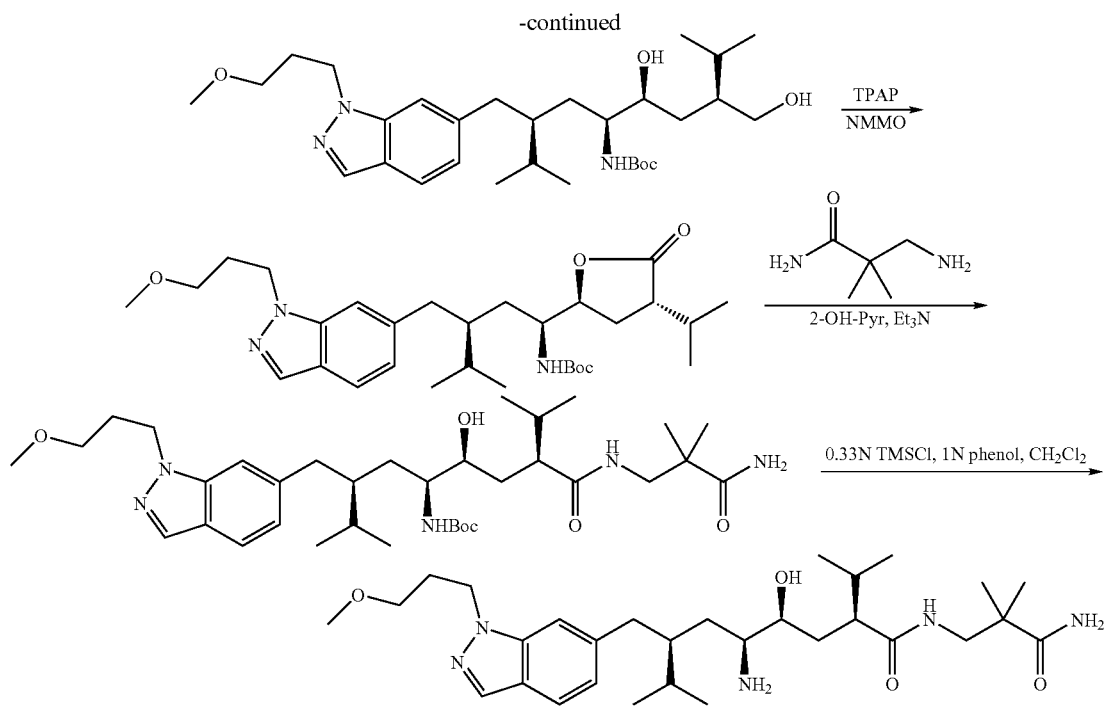

Step 1. tert-Butyl (3S,5S,8S)-8-(benzyloxymethyl)-6-hydroxy-3-((1-(3-methoxypropyl)-1H-indazol-6-yl)methyl)-2,9-dimethyldecan-5-ylcarbamate A 250-mL, three-neck, round-bottom flask equipped with a condenser under $N_2$ was charged with Mg powder (1.36 g, 56.7 mmol). The mixture was warmed briefly with a heat gun and a solution (S)-((2-(bromomethyl)-3-methylbutoxy)methyl)benzene (10.5 g, 37.8 mmol) in anhydrous THF (100 mL) was added dropwise. When the reaction mixture reached reflux temperature the heat gun was stopped. The mixture was stirred for an additional 30 min to afford a solution of (S)-(2-(benzyloxymethyl)-3-methylbutyl)magnesium bromide. A second 250-mL, three-neck round-bottom flask was charged with a solution of tert-butyl (2S,4S)-4-((1-(3-methoxypropyl)-1H-indazol-6-yl)methyl)-5-methyl-1-oxohexan-2-ylcarbamate (2.7 g, 6.3 mmol) in anhydrous THF (50 mL) and cooled to −78° C. under $N_2$ and the solution was stirred for 30 min. The freshly prepared solution of (S)-(2-(benzyloxymethyl)-3-methylbutyl)magnesium bromide prepared above was added dropwise and the mixture was warmed to rt and stirred overnight. 10% aq $NH_4Cl$ was added and the mixture was extracted with EtOAc (3×50 mL). The combined organic layers were washed brine, dried and evaporated. The residue was purified by flash chromatography on silica gel to afford the crude tert-butyl (3S,5S,8S)-8-(benzyloxymethyl)-6-hydroxy-3-((1-(3-methoxypropyl)-1H-indazol-6-yl)methyl)-2,9-dimethyldecan-5-ylcarbamate (1.3 g, 33% yield) as an 11:5 mixture of diastereomers at the alcohol center.

Step 2. tert-Butyl (3S,5S,6S,8S)-6-hydroxy-8-(hydroxymethyl)-3-((1-(3-methoxypropyl)-1H-indazol-6-yl)methyl)-2,9-dimethyldecan-5-ylcarbamate To a solution of tert-butyl (3S,5S,8S)-8-(benzyloxymethyl)-6-hydroxy-3-((1-(3-methoxypropyl)-1H-indazol-6-yl)methyl)-2,9-dimethyldecan-5-ylcarbamate (1.3 g, 2.1 mmol) in methanol 30 mL) was added 20% $Pd(OH)_2/C$ (26 mg). The mixture was hydrogenated under a balloon of $H_2$ at rt overnight and filtered. The filtrate was evaporated and purified by preparative HPLC to give tert-butyl (3S,5S,6S,8S)-6-hydroxy-8-(hydroxymethyl)-3-((1-(3-methoxypropyl)-1H-indazol-6-yl)methyl)-2,9-dimethyldecan-5-ylcarbamate (0.33 g, 30% yield) as an oil and tert-butyl (3S,5S,6R,8S)-6-hydroxy-8-(hydroxymethyl)-3-((1-(3-methoxypropyl)-1H-indazol-6-yl)methyl)-2,9-dimethyldecan-5-ylcarbamate (0.15 g, 14%) as an oil. MS: 534 ($M^+$+1)

Step 3. tert-Butyl (1S,3S)-1-((2S,4S)-4-isopropyl-5-oxotetrahydrofuran-2-yl)-3-((1-(3-methoxypropyl)-1H-indazol-6-yl)methyl)-4-methylpentylcarbamate To a stirred solution of N-methylmorpholine-N-oxide (270 mg, 2 mmol) in dry $CH_2Cl_2$ (10 mL) was added activated 4 Å molecular sieves (500 mg) at rt under $N_2$. After stirring for 2 h this mixture was added to a mixture of tetrapropylammonium perruthenate (22 mg, 0.062 mmol) and tert-butyl (3S,5S,6S,8S)-6-hydroxy-8-(hydroxymethyl)-3-((1-(3-methoxypropyl)-1H-indazol-6-yl)methyl)-2,9-dimethyldecan-5-ylcarbamate (0.33 g, 0.62 mmol) in dry $CH_2Cl_2$ (20 mL). The mixture was stirred overnight and filtered through a pad of silica gel. The filtrate was washed with water and brine, evaporated, and purified by flash chromatography on silica gel to afford tert-butyl (1S,3S)-1-((2S,4S)-4-isopropyl-5-oxotetrahydrofuran-2-yl)-3-((1-(3-methoxypropyl)-1H-indazol-6-yl)methyl)-4-methylpentylcarbamate (120 mg, 37%). $^1$H NMR (400 MHz, $CDCl_3$): δ7.93 (s, 1H), 7.60 (d, J=8.4 Hz, 1H), 7.20 (s, 1H), 6.98 (d, J=8.0 Hz, 1H), 4.46-4.38 (m, 4H), 3.89 (m, 1H), 3.29 (s, 6H), 2.86 (m, 1H), 2.58-2.52 (m, 2H), 2.18-2.2.08 (m, 5H), 1.70 (m, 2H), 1.47 (s, 9H), 1.04 (d, J=6.4 Hz, 3H), 1.00 (d, J=6.8 Hz, 3H), 0.92 (d, J=6.4 Hz, 3H), 0.89 (d, J=6.4 Hz, 3H); MS: 530 ($M^+$+1)

Step 4. tert-Butyl (3S,5S,6S,8S)-8-(3-amino-2,2-dimethyl-3-oxopropylcarbamoyl)-6-hydroxy-3-((1-(3-methoxypropyl)-1H-indazol-6-yl)methyl)-2,9-dimethyldecan-5-ylcarbamate A mixture of tert-butyl (1S,3S)-1-((2S,4S)-4-isopropyl-5-oxotetrahydrofuran-2-yl)-3-((1-(3-methoxypropyl)-1H-indazol-6-yl)methyl)-4-methylpentylcarbamate (120 mg, 0.25 mmol), Et₃N (1.5 mL), 2-hydroxypyridine (71.3 mg, 0.75 mmol), and 3-amino-2,2-dimethylpropanamide (87 mg, 0.75 mmol) was stirred at 80° C. overnight. The mixture was evaporated and purified by flash chromatography on silica gel to give tert-butyl (3S,5S,6S,8S)-8-(3-amino-2,2-dimethyl-3-oxopropylcarbamoyl)-6-hydroxy-3-((1-(3-methoxypropyl)-1H-indazol-6-yl)methyl)-2,9-dimethyldecan-5-ylcarbamate (120 mg, 65%). MS: 646 (M⁺+1)

Step 5. (2S,4S,5S,7S)-5-Amino-N-(3-amino-2,2-dimethyl-3-oxopropyl)-4-hydroxy-2-isopropyl-7-((1-(3-methoxypropyl)-1H-indazol-6-yl)methyl)-8-methylnonanamide A stock solution of 0.33 M Me₃SiCl and 1 M phenol in CH₂Cl₂ was prepared for Boc removal. tert-Butyl (3S,5S,6S,8S)-8-(3-amino-2,2-dimethyl-3-oxopropylcarbamoyl)-6-hydroxy-3-((1-(3-methoxypropyl)-1H-indazol-6-yl)methyl)-2,9-dimethyldecan-5-ylcarbamate (50 mg, 0.078 mmol) was dissolved in the Boc removal solution (15 mL) and stirred for 15 min at rt. Satd aq NaHCO₃ was added at 0° C. and the layers were separated. The aqueous layer was extracted with CH₂Cl₂ (3×20 mL). The combined organic layers were washed with brine, dried over Na₂SO₄, evaporated and purified by preparative HPLC to afford (2S,4S,5S,7S)-5-amino-N-(3-amino-2,2-dimethyl-3-oxopropyl)-4-hydroxy-2-isopropyl-7-((1-(3-methoxypropyl)-1H-indazol-6-yl)methyl)-8-methylnonanamide (10 mg, 24%). ¹H NMR (400 MHz, CDCl₃): δ7.92 (d, J=2.8 Hz, 1H), 7.60 (d, J=8.4 Hz, 1H), 7.22 (d, J=9.6 Hz, 1H), 6.98 (t, J=7.2 Hz, 1H), 6.53 (brs, 2H), 4.45(t, J=6.0 Hz, 1H), 3.54-3.44 (m, 2H), 3.31 (s, 3H), 3.31-3.14 (m, 3H), 2.87-2.42 (m, 5H), 2.17-2.14 (m, 3H), 1.84- 1.67 (m, 4H), 1.57-1.33 (m, 5H), 1.28 (m, 6H), 1.00 (d, J=8.0 Hz, 2H), 0.92-0.88 (m, 12 H); MS: 546 (M⁺+1)

EXAMPLE 7

(2S,4S,5S)-4-amino-6-(2,2-dimethylhexanamido)-5-hydroxy-2-isopropyl-1-(1-(3-methoxypropyl)-1H-indazol-6-yl)hexylacetate (I-7A)

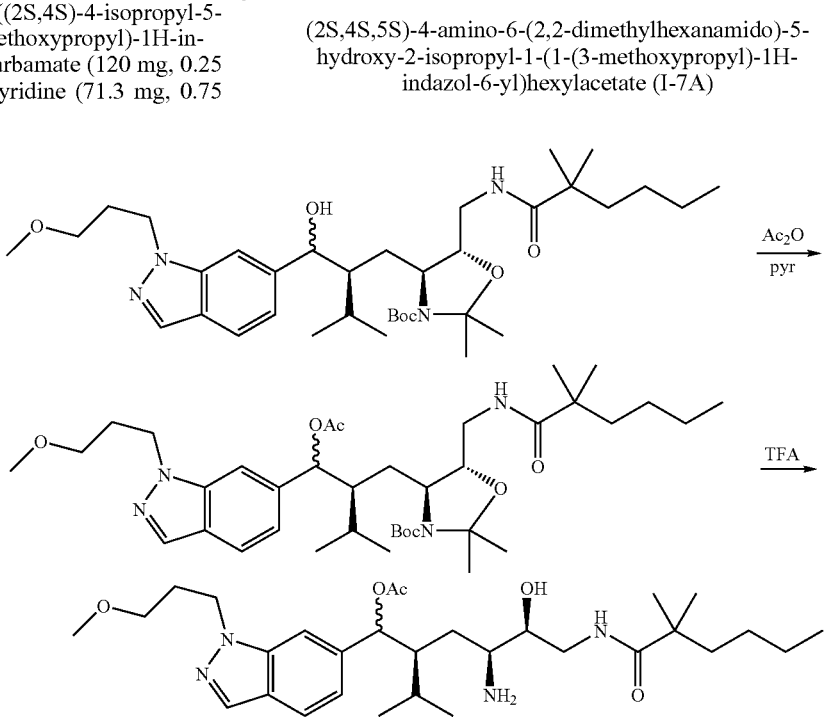

Step 1. (4S,5S)-tert-Butyl 4-((S)-2-(acetoxy(1-(3-methoxypropyl)-1H-indazol-6-yl)methyl)-3-methylbutyl)-5-((2,2-dimethylhexanamido)methyl)-2,2-dimethyloxazolidine-3-carboxylate To a solution of (4S,5S)-tert-butyl 5-((2,2-dimethylhexanamido)methyl)-4-((S)-2-(hydroxy(1-(3-methoxypropyl)-1H-indazol-6-yl)methyl)-3-methylbutyl)-2,2-dimethyloxazolidine-3-carboxylate (32 mg, 0.05 mmol) in Ac₂O (6 mL) was added pyridine (0.5 mL) dropwise. The reaction mixture was stirred at rt overnight. Satd aq NH₄Cl (10 mL) was added and the mixture was extracted with EtOAc (3×15 mL). The combined organic extracts were washed with brine, dried over Na₂SO₄ and evaporated. The residue was purified by column chromatography on silica gel to give (4S,5S)-tert-butyl 4-((S)-2-(acetoxy(1-(3-methoxypropyl)-1H-indazol-6-yl)methyl)-3-methylbutyl)-5-((2,2-dimethylhexanamido)methyl)-2,2-dimethyloxazolidine-3-carboxylate (25 mg, 73%). MS: 687 (M+1)

Step 2. (2S,4S,5S)-4-Amino-6-(2,2-dimethylhexanamido)-5-hydroxy-2-isopropyl-1-(1-(3-methoxypropyl)-1H-indazol-6-yl)hexyl acetate (4S,5S)-tert-butyl 4-((S)-2-(acetoxy(1-(3-methoxypropyl)-1H-indazol-6-yl)methyl)-3-methylbutyl)-5-((2,2-dimethylhexanamido)methyl)-2,2-dimethyloxazolidine-3-carboxylate (25 mg, 0.036 mmol) was dissolved 20% TFA/CH₂Cl₂ (6 mL) at 0° C. and the stirred for 2 h. The solvent was removed in vacuo and the residue was purified by preparative HPLC to give (2S,4S,5S)-4-amino-6-(2,2-dimethylhexanamido)-5-hydroxy-2-isopropyl-1-(1-(3-methoxypropyl)-1H- indazol-6-yl)hexyl acetate (12 mg, 52%). $^1$H NMR (400 MHz, CD$_3$OD): 0.84-1.00 (m, 9H), 1.11-1.32 (m, 10H), 1.58 (m, 3H), 1.95 (m, 1H), 2.14 (m, 6H), 3.12 (m, 2H), 3.45 (m, 1H), 3.83 (m, 1H), 4.50 (m, 2H), 5.91 (m, 1H), 7.12 (m, 1H), 7.53 (m, 1H), 7.75 (t, 3H), 8.04 (m, 1H). MS: 644 (M$^+$+1).

NaCl, 0.25 mg/mL bovine serum albumin, pH7.0) was added to 4 μL of test compound in DMSO at various concentrations ranging from 10 μM to 1 nM final concentrations. Next, 100 μL of trypsin-activated recombinant human renin (final enzyme concentration of 0.2-2 nM) in assay buffer was Table of Compounds

| Cpd. No. | Mass observed | $^1$H NMR solvent | Selected $^1$H NMR resonances |
|---|---|---|---|
| I-1A | 489 | CD$_3$OD | 0.86 (t, 3H), 0.94 (d, 3H), 0.98 (d, 3H), 1.13 (s, 6H), 1.27 (m, 4H), 1.48 (m, 2H), 1.67 (m, 3H), 1.88 (m, 1H), 2.12 (m, 2H), 2.62 (m, 1H), 2.85 (m, 1H), 2.97 (m, 1H), 3.12 (m, 1H), 3.28 (s, 3H), 3.36 (m, 1H), 3.64 (m, 1H), 4.47 (m, 2H), 7.06 (d, 1H), 7.39 (s, 1H), 7.67 (d, 1H), 7.97 (s, 1H) |
| I-1B | 489 | CD$_3$OD | 0.83 (t, 3H), 0.90 (d, 3H), 0.98 (d, 3H), 1.13 (s, 6H), 1.26 (m, 4H), 1.47 (m, 2H), 1.82 (m, 3H), 2.12 (m, 2H), 2.62 (m, 1H), 2.80 (m, 1H), 3.00 (m, 1H), 3.17 (m, 1H), 3.28 (s, 3H), 3.40 (m, 1H), 3.76 (m, 1H), 4.96 (m, 2H), 7.02 (d, 1H), 7.35 (s, 1H), 7.67 (d, 1H), 7.96 (s, 1H) |
| I-2A | 505 | CD$_3$OD | 0.86 (m, 3H), 0.89 (m, 3H), 0.97 (m, 3H), 2.15 (m, 2H), 3.28 (m, 3H), 3.46 (m, 1H), 3.70&3.82 (m, 1H), 4.48 (m, 2H), 7.20 (m, 1H), 7.55 (m, 1H), 7.74 (m, 1H), 7.98 (s, 1H) |
| I-3A | 501 | CD$_3$OD | 0.00 (m, 2H), 0.30 (m, 2H), 0.56 (m, 1H), 0.89 (m, 9H) 1.15 (m, 6H), 1.50 (m, 3H), 1.80 (m, 5H), 2.14 (m, 1H), 3.15 (m, 1H), 3.46 (m, 1H), 3.72 (m, 1H), 4.50 (m, 2H), 7.18 (d, 1H), 7.58 (s, 1H), 7.73 (d, 1H), 7.98 (s, 1H) |
| I-3B | | CD$_3$OD | 0.00 (m, 2H), 0.32 (m, 2H), 0.58 (m, 1H), 0.90 (m, 9H), 1.17 (m, 6H), 1.50 (m, 3H), 1.74 (m, 4H), 2.06 (m, 1H), 2.12 (m, 1H), 2.54 (m, 1H), 2.76 (m, 1H), 3.50 (m, 1H), 4.48 (m, 2H), 7.20 (d, 1H), 7.62 (s, 1H), 7.74 (d, 1H), 7.99 (s, 1H) |
| I-3C | 501 | CD$_3$OD | 0.00 (m, 2H), 0.29 (m, 2H), 0.56 (m, 1H), 0.89 (m, 9H) 1.11 (m, 6H), 1.48 (m, 3H), 1.80 (m, 5H), 2.12 (m, 1H), 2.76 (m, 1H), 3.12 (m, 1H), 3.70 (m, 1H), 4.48 (m, 2H), 7.15 (d, 1H), 7.60 (s, 1H), 7.73 (d, 1H), 7.98 (s, 1H) |
| I-3D | 501 | CD$_3$OD | 0.00 (m, 2H), 0.29 (m, 2H), 0.55 (m, 1H), 0.86 (m, 9H) 1.17 (m, 6H), 1.53 (m, 3H), 1.75 (m, 4H), 1.97 (m, 1H), 3.19 (m, 2H), 3.46 (m, 1H), 3.82 (m, 1H), 4.49 (m, 2H), 4.65 (m, 1H), 7.20 (d, 1H), 7.57 (s, 1H), 7.73 (d, 1H), 7.99 (s, 1H) |
| I-4A | 519 | CD$_3$OD | 0.90 (m, 6H), 0.96 (m, 3H), 1.17 (m, 9H), 1.54 (m, 3H), 2.15 (m, 2H), 3.42 (m, 5H), 3.70 (m, 1H), 4.51 (m, 1H), 7.18 (d, 1H), 7.56 (s, 1H), 7.75 (d, 1H), 8.00 (s, 1H) |
| I-4B | 519 | CD$_3$OD | 0.89 (m, 9H), 1.17 (m, 6H), 1.52 (m, 2H), 1.74 (m, 2H), 1.96 (m, 1H), 2.14 (m, 2H), 3.17 (m, 2H), 3.40 (m, 5H), 3.70 (m, 1H), 4.48 (m, 1H), 4.65 (m, 1H), 7.20 (d, 1H), 7.54 (s, 1H), 7.74 (d, 1H), 8.00 (s, 1H) |
| I-5A | 533 | CD$_3$OD | 0.91 (m, 9H), 1.12 (m, 6H), 1.53 (m, 3H), 1.86 (m, 2H), 2.12 (m, 2H), 3.30 (s, 3H), 3.72 (m, 1H), 4.50 (m, 2H), 7.19 (m, 1H), 7.56 (m, 1H), 7.73 (m, 1H), 7.99 (s, 1H) |
| I-6A | 546 | CDCl$_3$ | 0.88 (m, 12H), 1.18 (m, 6H), 2.15 (m, 2H), 2.47 (m, 2H), 2.68 (m, 2H), 2.87 (m, 2H), 3.16 (m, 1H), 3.29 (s, 3H), 3.50 (m, 2H), 4.46 (m, 2H), 5.92 (m, 1H), 6.50 (m, 2H), 6.99 (m, 1H), 7.22 (m, 1H), 7.60 (m, 1H), 7.92 (m, 1H) |
| I-6B | 546 | CDCl$_3$ | 0.83 (m, 12H), 1.19 (m, 6H), 2.16 (m, 2H), 2.65 (m, 2H), 2.87 (m, 4H), 3.20 (m, 1H), 3.30 (s, 3H), 3.45 (m, 2H), 4.46 (m, 2H), 5.84 (m, 1H), 6.32 (m, 1H), 6.46 (m, 1H), 6.98 (m, 1H), 7.21 (m, 1H), 7.61 (m, 1H), 7.93 (m, 1H) |
| I-7A | 547 | CD$_3$OD | 0.90 (m, 9H), 1.15 (m, 6H), 3.27 (s, 3H), 3.45 (m, 1H), 3.66&3.82 (m, 1H), 4.50 (m, 2H), 5.92 (m, 1H), 7.15 (m, 1H), 7.50 (m, 1H), 7.76 (m, 1H), 8.03 (m, 1H) |

EXAMPLE 8

In Vitro Activity Studies—IC$_{50}$ Values for Renin Inhibition

The action of renin inhibitors was demonstrated experimentally by means of an in vitro test which measures the increase in fluorescence of an internally quenched peptide substrate. The sequence of this peptide corresponds to the sequence of human angiotensinogen. The following test protocol was used:

All reactions were carried out in a flat bottom white opaque microtiter plate. A 4 μL aliquot of 400 μM renin substrate (DABCYL-γ-Abu-Ile-His-Pro-Phe-His-Leu-Val-Ile-His-Thr-EDANS) in 192 μL assay buffer (50 mM BES, 150 mM added, and the solution was mixed by pipetting. The increase in fluorescence at 495 nm (excitation at 340 nm) was measured for 60-360 minutes at room temperature using a Perkin-Elmer Fusion microplate reader. The slope of a linear portion of the plot of fluorescence increase as a function of time was then determined, and the rate was used for calculating percent inhibition in relation to uninhibited control. The percent inhibition values were plotted as a function of inhibitor concentration, and the IC$_{50}$ was determined from a fit of this data to a four parameter equation. The IC$_{50}$ was defined as the concentration of a particular inhibitor that reduces the formation of product by 50% relative to a control sample containing no inhibitor.

In the in vitro systems the compounds of the invention exhibited inhibiting activities at minimum concentrations of from approximately $5\times10^{-5}$ M to approximately $10^{-12}$ M. Preferred compounds of the invention exhibited inhibiting activities at minimum concentrations of from approximately $5\times10^{-6}$ M to approximately $10^{-12}$ M. More preferred compounds of the invention exhibited inhibiting activities at minimum concentrations of from approximately $5\times10^{-8}$ M to approximately $10^{-12}$ M. (Wang G. T. et al. *Anal. Biochem.* 1993, 210, 351; Nakamura, N. et al. *J. Biochem.* (*Tokyo*) 1991, 109, 741; Murakami, K. et al. *Anal Biochem.* 1981, 110, 232).

EXAMPLE 9

Inhibition of Human Plasma

The action of renin inhibitors in vitro in human plasma can also be demonstrated experimentally by the decrease in plasma renin activity (PRA) levels observed in the presence of the compounds. Incubations mixtures contain in the final volume of 250 µL 95.5 mM N,N-bis(2-hydroxyethyl)-2-aminoethanesulfonic acid, pH 7.0, 8 mM EDTA, 0.1 mM neomycin sulfate, 1 mg/mL sodium azide, 1 mM phenylmethanesulfonyl fluoride, 2% DMSO and 87.3% of pooled mixed-gender human plasma stabilized with EDTA. For plasma batches with low PRA (less than 1 ng/ml/hr) ~2 pM of recombinant human renin is added to achieve PRA of 3-4 ng/ml/hr. The cleavage of endogenous angiotensinogen in plasma is carried out at 37° C. for 90 min and the product angiotensin I is measured by competitive radioimmunoassay using Dia-Sorin PRA kit. Uninhibited incubations containing 2% DMSO and fully inhibited controls with 2 µM of isovaleryl-Phe-Nle-Sta-Ala-Sta-OH are then used for deriving percent of inhibition for each concentration of inhibitors and fitting dose-response data into a four parametric model from which $IC_{50}$ values, defined as concentrations of inhibitors at which 50% inhibition occurs, are determined.

EXAMPLE 10

In Vivo Activity

The cardiac and systemic hemodynamic efficacy of selective renin inhibitors can be evaluated in vivo in sodium-depleted, normotensive cynomolgus monkeys and in sodium-depleted, normotensive beagle dogs following a single oral and intravenous administration of the test compound. Arterial blood pressure is monitored by telemetry in freely moving, conscious animals.

Cynomolgus Monkey: Six male naïve cynomolgus monkeys weighing between 2.5 and 3.5 kg can be used in the studies. At least 4 weeks before the experiment, the monkeys are anesthetized with ketamine hydrochloride (15 mg/kg, i.m.) and xylazine hydrochloride (0.7 mg/kg, i.m.), and are implanted into the abdominal cavity with a transmitter (Model #TL11M2-D70-PCT, Data Sciences, St. Paul, Minn.). The pressure catheter is inserted into the lower abdominal aorta via the femoral artery. The bipotential leads are placed in Lead II configuration. The animals are Housed under constant temperature (19-25° C.), humidity (>40%) and lighting conditions (12 h light and dark cycle), are fed once daily, and are allowed free access to water. The animals are sodium depleted by placing them on a low sodium diet (0.026%, Expanded Primate Diet 829552 MP-VENaCl (P), Special Diet Services, Ltd., UK) 7 days before the experiment and furosemide (3 mg/kg, intramuscularly i.m., Aventis Pharmaceuticals) is administered at −40 h and −16 h prior to administration of test compound.

For oral dosing, the renin inhibitors are formulated in 0.5% methylcellulose at dose levels of 10 and 30 mg/kg (5 mL/kg) by infant feeding tubes. For intravenous delivery, a silastic catheter is implanted into posterior vena cava via a femoral vein. The catheter is attached to the delivery pump via a tether system and a swivel joint. Test compound (dose levels of 0.1 to 10 mg/kg, formulated at 5% dextrose) is administered by continuous infusion (1.67 mL/kg/h) or by bolus injection (3.33 mL/kg in 2 min).

Arterial blood pressures (systolic, diastolic and mean) and body temperature are recorded continuously at 500 Hz and 50 Hz, respectively, using the Dataquest™ A.R.T. (Advanced Research Technology) software. Heart rate is derived from the phasic blood pressure tracing. During the recording period, the monkeys are kept in a separate room without human presence to avoid pressure changes secondary to stress. All data are expressed as mean±SEM. Effects of the renin inhibitors on blood pressure are assessed by ANOVA, taking into account the factors dose and time compared with the vehicle group.

Beagle Dogs: Non-naive Beagle dogs (2 per sex) weighing between 9 and 11 kg can be used in the studies. Each animal is implanted subcutaneously with a telemetry transmitter (Data Sciences) and the blood pressure catheter is inserted into the left femoral artery. The electrocardiogram leads are also tunneled subcutaneously to the appropriate anatomical regions. The animals are housed under constant temperature and lighting conditions, are fed once daily, and are allowed free access to water. A sodium depleted state is produced by placing them on a low-sodium diet (<4 meq/day, a combination of canned Prescription Diet canine h/d, from Hill's Pet Products and dry pellets from Bio-Serv Inc., Frenchtown, N.J.) beginning 10 days before the experiment, and furosemide (3 mg/kg i.m.; Aventis Pharmaceuticals) is administered at −40 and −16 h prior to administration of test compound.

A renin inhibitor is orally administered by orogastric gavage to all overnight fasted animals at a dose level of 30 mg/kg (4 mL/kg formulated in 0.5% methylcellulose). Food is given 4 h postdose. In some experiments, the renin inhibitor is administered by bolus i.v. at increasing dose levels of 1, 3 and 6 mg/kg (2, 6 and 20 mg/mL formulated in sterile saline). Cardiovascular parameters are collected continuously at least 80 min predose and 3 h postdose, followed by every 10 min for 5 h and every 30 min for 16 h postdose. The Dataquest™ ART (version 2.2) software package from DSI (Data Sciences International) is used to collect telemetered cardiovascular data.

EXAMPLE 11

The efficacy of the renin inhibitors can also be evaluated in vivo in double transgenic rats engineered to express human renin and human angiotensinogen (Bohlender J, Fukamizu A, Lippoldt A, Nomura T, Dietz R, Menard J, Murakami K, Luft F C, Ganten D. High human renin hypertension in transgenic rats. *Hypertension* 1997, 29, 428-434). Experiments are conducted in 6-week-old double transgenic rats (dTGRs). The model has been described in detail earlier. Briefly, the human renin construct used to generate transgenic animals made up the entire genomic human renin gene (10 exons and 9 introns), with 3.0 kB of the 5'-promoter region and 1.2 kB of 3' additional sequences. The human angiotensinogen construct made up the entire human angiotensinogen gene (5 exons and 4 introns), with 1.3 kB of 5'-flanking and 2.4 kB of 3'-flanking sequences. The rats can be purchased from RCC Ltd (Füllinsdorf, Switzerland). Radio telemetry transmitters can be surgically implanted at 4 weeks of age. The telemetry system provides 24-h recordings of systolic, mean, diastolic arterial pressure (SAP, MAP, DAP, respectively) and heart rate (HR). Beginning on day 42, animals are transferred to telemetry cages. A 24 h telemetry reading is obtained. Rats are then dosed orally on the following 4 consecutive days (days 43-46). The rats are monitored continuously and allowed free access to standard 0.3%-sodium rat chow and drinking water.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound of formula I

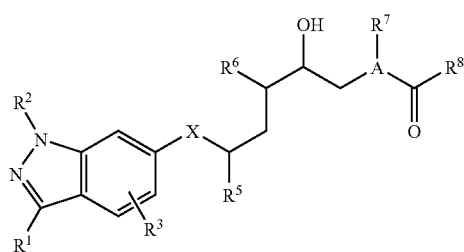

wherein $R^1$ is H, lower alkyl, cycloalkyl, lower haloalkyl, halocycloalkyl, amino, cyano, carboxy, aminocarbonyl, N-mono-lower alkyl-aminocarbonyl, N,N-di-lower alkyl-aminocarbonyl, cycloalkyl-lower alkyl, halocycloalkyl-loweralkyl, cyano-lower alkyl, hydroxy-lower alkyl, lower alkoxy-lower alkyl, lower haloalkoxy-lower alkyl, lower alkoxy-lower alkoxy-lower alkyl, lower haloalkoxy-lower alkoxy-lower alkyl, cycloalkoxy-lower alkyl, halocycloalkoxy-lower alkyl, lower alkanoylamino-lower alkyl, lower alkoxycarbonyl-amino-lower alkyl, aminocarbonylamino-lower alkyl, lower alkylaminocarbonylamino-lower alkyl, di(lower alkyl)aminocarbonylamino-lower alkyl, aminosulfonylamino-lower alkyl, lower alkylaminosulfonylamino-lower alkyl, di(lower alkyl)aminosulfonylamino-lower alkyl, lower haloalkoxy-lower alkyl, aminocarbonyl-lower alkyl, N-mono-lower alkyl-aminocarbonyl-lower alkyl, N,N-di-lower alkyl-aminocarbonyl-lower alkyl, carbamoyl-lower alkyl, or N-mono- or N,N -di-lower alkylcarbamoyl-lower alkyl;

$R^2$ is lower alkyl, lower haloalkyl, cycloalkyl, halocycloalkyl, cycloalkyl-lower alkyl, halocycloalkyl-loweralkyl, cyano-lower alkyl, hydroxy-lower alkyl, lower alkoxy-lower alkyl, lower haloalkoxy-lower alkyl, lower alkoxy-lower alkoxy-lower alkyl, lower haloalkoxy-lower alkoxy-lower alkyl, cycloalkoxy-lower alkyl, halocycloalkoxy-lower alkyl, lower alkanoylamino -lower alkyl, lower alkoxycarbonyl-amino-lower alkyl, aminocarbonylamino-lower alkyl, lower alkylaminocarbonylamino-lower alkyl, di(lower alkyl)aminocarbonylamino-lower alkyl, aminosulfonyl-amino-lower alkyl, lower alkylaminosulfonylamino-lower alkyl, di(lower alkyl)aminosulfonylamino-lower alkyl, lower haloalkoxy-lower alkyl, aminocarbonyl-lower alkyl, N-mono-lower alkyl-aminocarbonyl-lower alkyl, N,N-di-lower alkyl-aminocarbonyl-lower alkyl, carbamoyl-lower alkyl, or N-mono- or N,N-di-lower alkylcarbamoyl-lower alkyl;

$R^3$ is H, halogen, cyano, lower alkyl, or lower haloalkyl;

X is methylene, hydroxymethylene, or lower alkanoyloxymethylene;

$R^5$ is lower alkyl, lower haloalkyl, cycloalkyl, halocycloalkyl, lower alkyl-cycloalkyl, lower haloalkyl-cycloalkyl, cycloalkyl-lower alkyl, aryl, aryl-lower alkyl, heterocyclyl, or heterocyclyl-lower alkyl;

$R^6$ is amino or lower alkylamino;

A is N or CH;

$R^7$ is hydrogen, lower alkyl, lower haloalkyl, cycloalkyl, lower alkoxy-lower alkyl, or lower haloalkoxy-lower alkyl;

$R^8$ is 1) lower alkyl, lower haloalkyl, $C_8$-$C_{15}$alkyl, $C_8$-$C_{15}$haloalkyl, cycloalkyl, halocycloalkyl, lower alkyl-cycloalkyl, cycloalkyl-lower alkyl, halocycloalkyl-lower alkyl, lower alkoxy -loweralkyl, lower haloalkoxy-lower alkyl, cycloalkoxy-lower alkyl, cycloalkoxy-cycloalkyl, lower alkylthio-lower alkyl, lower haloalkylthio-lower alkyl, lower alkanesulfonyl-lower alkyl, lower haloalkanesulfonyl-lower alkyl, lower alkylthio-cycloalkyl, lower haloalkylthio-cycloalkyl, lower alkanesulfonyl-cycloalkyl, lower haloalkanesulfonyl-cycloalkyl, aryl, aryl-lower alkyl, aryl-lower hydroxyalkyl, arylcycloalkyl, aryloxy-lower alkyl, aryloxy cycloalkyl, arylthio-lower alkyl, arylsulfonyl-lower alkyl, arylthio-cycloalkyl, arylsulfonyl-cycloalkyl, lower alkanoyl-lower alkyl, hydroxy-lower alkyl, amino-lower alkyl, ower alkanoylamino-lower alkyl, N-mono- lower alkylamino-lower alkyl, N,N-di-lower alkylamino-lower alkyl, piperidino-lower alkyl, hydroxypiperidino-lower alkyl, lower alkoxypiperidino-lower alkyl, morpholino-lower alkyl, dimethylmorpholino-lower alkyl, thiomorpholino-lower alkyl, S,S-dioxothiomorpholino-lower alkyl, carboxy-lower alkyl, lower alkoxycarbonyl-lower alkyl, carbamoyl-lower alkyl, N-mono -lower alkylcarbamoyl-lower alkyl, N,N-di-lower alkylcarbamoyl-lower alkyl, carboxy-(hydroxy) -lower alkyl, lower alkoxycarbonyl-(hydroxy)-lower alkyl, carbamoyl-(hydroxy)-lower alkyl, N -mono- lower alkylcarbamoyl-(hydroxy)-lower alkyl, N,N-di-lower alkylcarbamoyl-(hydroxy)-lower alkyl, 5- or 6-membered carboxycycloalkyl-lower alkyl, 5- or 6-membered lower alkoxycarbonyl-cycloalkyl-lower alkyl, 5- or 6-membered carbamoylcycloalkyl-lower alkyl, 5- or 6-membered N-mono-alkylcarbamoylcycloalkyl-lower alkyl, N,N-di-lower alkylcarbamoylcycloalkyl-lower alkyl, cyano-lower alkyl, sulfamoyl-lower alkyl, lower alkylsulfamoyl-lower alkyl, di-lower alkylsulfamoyl-lower alkyl, imidazolyl-lower alkyl, oxopyrrolidinyl-lower alkyl, benzimidazolyl-lower alkyl, oxadiazolyl-lower alkyl, pyridyl-lower alkyl, oxopiperidinyl-lower alkyl, quinolinyl-lower alkyl, piperidin-4-yl-lower alkyl, or lower alkanoylpiperidin-4-yl-lower alkyl, wherein said aryl, imidazolyl, benzimidazolyl, oxadiazolyl, pyridyl, quinolinyl, aryloxy, arylthio, and arylsulfonyl groups are optionally substituted with up to four groups independently selected from halo, cyano, nitro, optionally halogenated lower alkyl, optionally halogenated lower alkoxy, optionally halogenated lower alkylthio, optionally halogenated lower alkanesulfonyl, and lower alkoxycarbonyl; or

2) NR$^9$R$^{10}$;

R$^9$ is 1) hydrogen, lower alkyl, lower haloalkyl, lower alkenyl, (C$_8$-C$_{15}$)alkyl, (C$_8$-C$_{15}$)haloalkyl, cycloalkyl, halocycloalkyl, lower alkyl-cycloalkyl, cycloalkyl-lower alkyl, halocycloalkyl-lower alkyl, lower alkoxy-loweralkyl, lower haloalkoxy-lower alkyl, cycloalkoxy-lower alkyl, cycloalkoxy-cycloalkyl, lower alkylthio-lower alkyl, lower haloalkylthio-lower alkyl, lower alkanesulfonyl-lower alkyl, lower haloalkanesulfonyl-lower alkyl, lower alkylthio-cycloalkyl, lower haloalkylthio-cycloalkyl, lower alkanesulfonyl-cycloalkyl, lower haloalkanesulfonyl-cycloalkyl, aminocarbonyl-lower alkyl, lower alkyl-aminocarbonyl-lower alkyl, or di(lower alkyl)-aminocarbonyl-lower alkyl, or 2) aryl, aryl-lower alkyl, aryloxy-lower alkyl, arylthio-lower alkyl, or arylsulfonyl-lower alkyl
    wherein the aryl groups are optionally substituted with up to four groups independently selected from halo, cyano, optionally halogenated lower alkyl, optionally halogenated lower alkoxy, optionally halogenated lower alkylthio, and optionally halogenated lower alkanesulfonyl;

R$^{10}$ is 1) hydrogen, lower alkyl, lower haloalkyl, (C$_8$-C$_{15}$)alkyl, (C$_8$-C$_{15}$)haloalkyl, cycloalkyl, halocycloalkyl, cycloalkyl-lower alkyl, halocycloalkyl-lower alkyl, lower alkoxy-lower alkyl, lower haloalkoxy-lower alkyl, alkylthio-lower alkyl, lower haloalkylthio-lower alkyl, lower alkanesulfonyl-lower alkyl, lower haloalkanesulfonyl-lower alkyl, or 2) aryl or aryl-lower alkyl
    wherein the aryl groups are optionally substituted with up to four groups independently selected from halo, cyano, optionally halogenated lower alkyl, optionally halogenated lower alkoxy, optionally halogenated lower alkylthio, and optionally halogenated lower alkanesulfonyl;

or an enantiomer, diastereomer, or salt thereof.

2. The compound of claim 1 or an enantiomer, diastereomer, or salt thereof, wherein R$^1$ is is H, lower alkyl, cycloalkyl, lower haloalkyl or halocycloalkyl.

3. A compound of claim 2 wherein:
R$^1$ is H or methyl;
R$^2$ is lower alkyl, cycloalkyl-lower alkyl, cyano-lower alkyl, hydroxy-lower alkyl, lower alkoxy-lower alkyl, lower alkoxy-lower alkoxy-lower alkyl, lower haloalkoxy-lower alkoxy-lower alkyl, cycloalkoxy-lower alkyl, halocycloalkoxy-lower alkyl, lower alkanoylamino-lower alkyl, lower alkoxycarbonyl-amino-lower alkyl, aminocarbonylamino-lower alkyl, lower alkylaminocarbonylamino-lower alkyl, di(lower alkyl)aminocarbonylamino-lower alkyl, aminosulfonylamino-lower alkyl, lower alkylaminosulfonylamino-lower alkyl, di(lower alkyl)aminosulfonylamino-lower alkyl, aminocarbonyl-lower alkyl, N-mono-lower alkyl-aminocarbonyl-lower alkyl, carbamoyl-lower alkyl, or N-mono-lower alkylcarbamoyl-lower alkyl;
R$^3$ is H, fluorine, cyano, methyl, or trifluoromethyl;
X is methylene, hydroxymethylene, or acetoxymethylene;
R$^5$ is lower alkyl or cycloalkyl;
R$^6$ is amino,
A is N or CH;
R$^7$ is H, lower alkyl, or cycloalkyl;
R$^8$ is 1) (C$_3$-C$_{11}$)alkyl, (C$_3$-C$_{11}$)haloalkyl, (C$_3$-C$_7$)cycloalkyl, (C$_3$-C$_{11}$)cycloalkylalkyl, (C$_3$-C$_{11}$)-alkoxyalkyl, aryl, aryl(C$_1$-C$_3$)alkyl, aryl(C$_3$-C$_6$)cycloalkyl, arylhydroxy(C$_1$-C$_3$)alkyl, aryloxy(C$_1$-C$_6$) alkyl, or aryloxy(C$_3$-C$_6$)cycloalkyl wherein aryl or aryloxy may be unsubstituted or substituted with one to three groups independently selected from halogen, cyano, (C$_1$-C$_3$) alkyl, halo(C$_1$-C$_3$) alkyl, (C$_1$-C$_3$)alkoxy, halo(C$_1$-C$_3$) alkoxy; or

2) NR$_9$R$_{10}$;

R$^9$ is 1) hydrogen, (C$_1$-C$_{10}$)alkyl, (C$_3$-C$_7$)alkenyl, (C$_3$-C$_7$) cycloalkyl, (C$_3$-C$_6$)cycloalkyl(C$_1$-C$_6$) alkyl, (C$_1$-C$_6$) alkoxy(C$_1$-C$_6$)alkyl, or aminocarbonyl(C$_1$-C$_6$)alkyl, or 2) aryl or aryl(C$_1$-C$_4$)alkyl
    wherein the aryl moiety is optionally substituted with up to 4 groups independently selected from fluorine, chlorine, cyano, (C$_1$-C$_3$)alkyl, halo(C$_1$-C$_3$) alkyl, (C$_1$-C$_3$)alkoxy, halo(C$_1$-C$_3$)alkoxy, and (C$_1$-C$_3$)alkanesulfonyl;

R$^{10}$ 1'1 is hydrogen, lower alkyl, or lower haloalkyl; and or an enantiomer, diastereomer, or salt thereof.

4. A compound of claim 2 wherein
R$^1$=R$^3$=R$^7$=H;
R$^2$ is lower alkyl, cycloalkyl-lower alkyl, hydroxy-lower alkyl, lower alkoxy-lower alkyl, cycloalkoxy-lower alkyl, lower alkanoylamino-lower alkyl, lower alkoxycarbonyl-amino-lower alkyl, aminocarbonyl-lower alkyl, or N-mono-lower alkyl-aminocarbonyl-lower alkyl;
X is methylene or hydroxymethylene;
R$^5$ is isopropyl;
R$^6$ is amino,
A is N;
R$^8$ is (C$_1$-C$_{10}$)alkyl, (C$_3$-C$_7$)cycloalkyl, (C$_3$-C$_6$)cycloalkyl(C$_1$-C$_5$)alkyl, (C$_1$-C$_6$)alkoxy(C$_1$-C$_6$)alkyl, aminocarbonyl(C$_1$-C$_5$)alkyl, or phenyl(C$_1$-C$_4$)alkyl;

or an enantiomer, diastereomer, or salt thereof.

5. A compound of claim 2 wherein:
R$^1$=R$^3$=R$^{10}$=H;
R$^2$ is lower alkyl, cycloalkyl-lower alkyl, hydroxy-lower alkyl, lower alkoxy-lower alkyl, cycloalkoxy-lower alkyl, lower alkanoylamino-lower alkyl, lower alkoxycarbonyl-amino-lower alkyl, aminocarbonyl-lower alkyl, or N-mono-lower alkyl-aminocarbonyl-lower alkyl;
X is methylene or hydroxymethylene;
R$^5$ is isopropyl;
R$^6$ is amino,
A is CH;
R$^7$ is isopropyl;
R$^8$ is NR$^9$R$^{10}$;
R$^9$ is (C$_1$-C$_{10}$)alkyl, (C$_3$-C$_7$)cycloalkyl, (C$_3$-C$_6$)cycloalkyl(C$_1$-C$_5$)alkyl, (C$_1$-C$_6$)alkoxy(C$_1$-C$_6$)alkyl, aminocarbonyl(C$_1$-C$_5$)alkyl, or phenyl(C$_1$-C$_4$)alkyl;

or an enantiomer, diastereomer, or salt thereof.

6. A compound of claim 2 wherein:
R$^1$=R$^3$=R$^7$=H;
R$^2$ is cyclopropylethyl, 3-methoxypropyl, 3-ethoxypropyl, or 3-isopropoxypropyl;
X is methylene or hydroxymethylene;
R$^5$ is isopropyl;
R$^6$ is amino;
A is N;
R$^8$ is 2-methyl-2-hexyl;

or an enantiomer, diastereomer, or salt thereof.

7. A compound of claim 2 wherein:
R$^1$=R$^3$=R$^{10}$H;
R$^2$ is cyclopropylethyl, 3-methoxypropyl, 3-ethoxypropyl, or 3-isopropoxypropyl;
X is methylene or hydroxymethylene;
R$^5$ is isopropyl;
R$^6$ is amino;

A is CH;
R⁷ is isopropyl;
R⁸ is NR9R10;
R⁹ is —CH₂C(Me)₂CONH₂;
or an enantiomer, diastereomer, or salt thereof.

8. A compound of claim 2 wherein at least one, two, or preferably all three of the asymmetric carbon atoms of the main chain have the stereochemical configuration shown in formula Ia

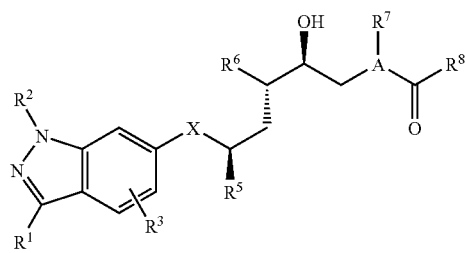

or a pharmaceutically acceptable salt thereof.

9. A compound of claim 2 which is:
I-1 N-(3-amino-2-hydroxy-5-((1-(3-methoxypropyl)-1H-indazol-6-yl)methyl)-6-methylheptyl)-2,2-dimethylhexanamide
I-2 N-(3-amino-5-(1-(2-cyclopropylethyl)-1H-indazol-6-yl)(hydroxy)methyl)-2-hydroxy-6-methylheptyl)-2,2-dimethylhexanamide
I-3 N-(3-amino-2-hydroxy-5-(hydroxy(1-(3-methoxypropyl)-1H-indazol-6-yl)methyl)-6-methylheptyl)-2,2-dimethylhexanamide
I-4 N-(3-amino-5-((1-(3-ethoxypropyl)-1H-indazol-6-yl)(hydroxy)methyl)-2-hydroxy-6-methylheptyl)-2,2-dimethylhexanamide
I-5 N-(3-amino-2-hydroxy-5-(hydroxy(1-(3-isopropoxypropyl)-1H-indazol-6-yl)methyl)-6-methylheptyl)-2,2-dimethylhexanamide
I-6 5-amino-N-(3-amino-2,2-dimethyl-3-oxopropyl)-4-hydroxy-2-isopropyl-7-((1-(3-methoxypropyl)-1H-indazol-6-y)methyl)-8-methylnonanamide or
I7 4-amino-6-(2,2-dimethylhexanamido)-5-hydroxy-2-isopropyl-1-(1-(3-methoxypropyl)-1H -indazol-6-yl) hexyl acetate
or an enantiomer, diastereomer, or a salt thereof.

10. A compound of claim 2 which is:

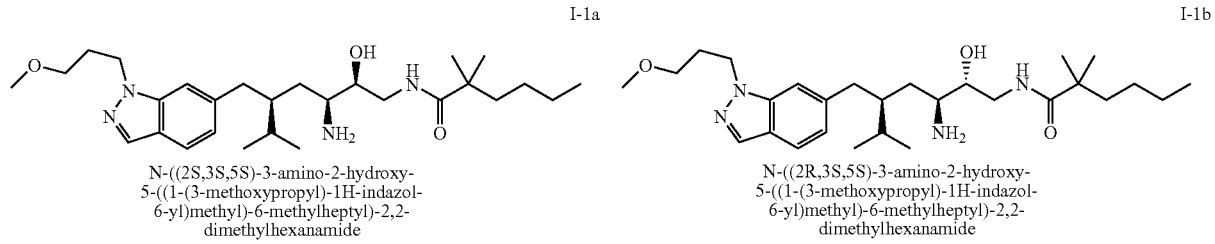

N-((2S,3S,5S)-3-amino-2-hydroxy-5-((1-(3-methoxypropyl)-1H-indazol-6-yl)methyl)-6-methylheptyl)-2,2-dimethylhexanamide N-((2R,3S,5S)-3-amino-2-hydroxy-5-((1-(3-methoxypropyl)-1H-indazol-6-yl)methyl)-6-methylheptyl)-2,2-dimethylhexanamide

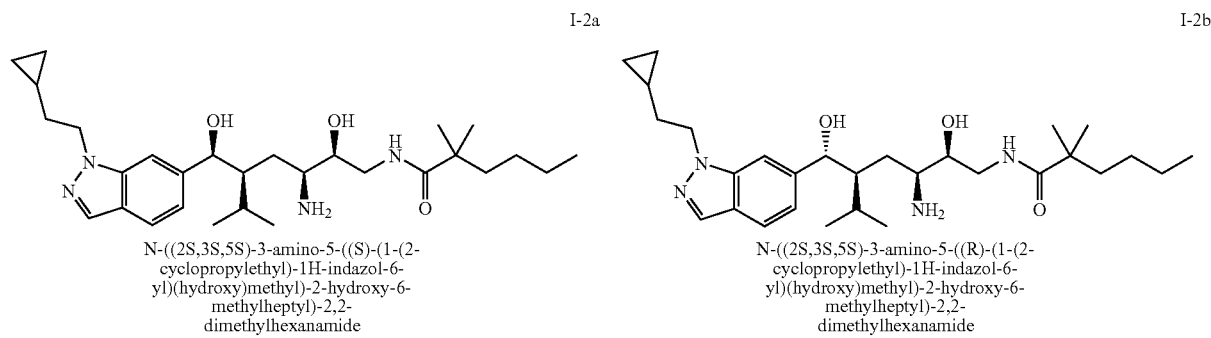

N-((2S,3S,5S)-3-amino-5-((S)-(1-(2-cyclopropylethyl)-1H-indazol-6-yl)(hydroxy)methyl)-2-hydroxy-6-methylheptyl)-2,2-dimethylhexanamide N-((2S,3S,5S)-3-amino-5-((R)-(1-(2-cyclopropylethyl)-1H-indazol-6-yl)(hydroxy)methyl)-2-hydroxy-6-methylheptyl)-2,2-dimethylhexanamide

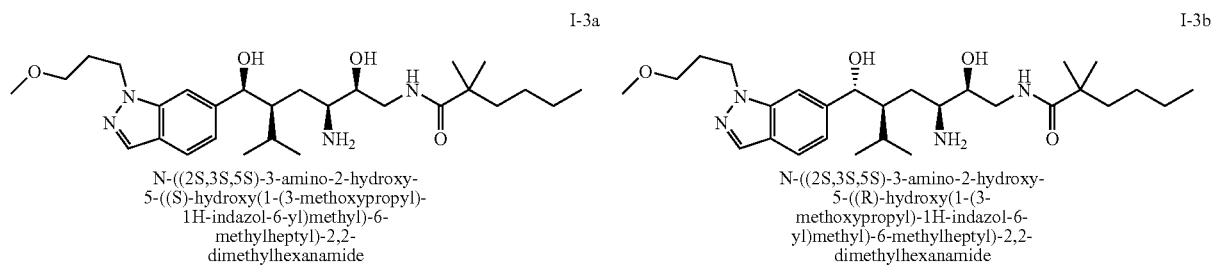

N-((2S,3S,5S)-3-amino-2-hydroxy-5-((S)-hydroxy(1-(3-methoxypropyl)-1H-indazol-6-yl)methyl)-6-methylheptyl)-2,2-dimethylhexanamide N-((2S,3S,5S)-3-amino-2-hydroxy-5-((R)-hydroxy(1-(3-methoxypropyl)-1H-indazol-6-yl)methyl)-6-methylheptyl)-2,2-dimethylhexanamide

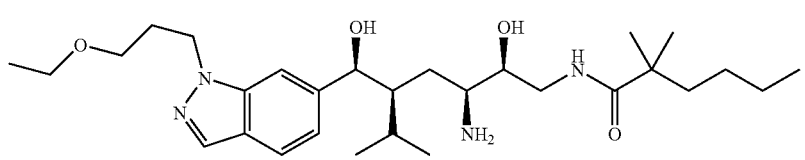

N-((2S,3S,5S)-3-amino-5-((S)-(1-(3-
ethoxypropyl-1H-indazol-6-
yl)(hydroxy)methyl)-2-hydroxy-6-
methylheptyl)-2,2-
dimethylhexanamide I-4a

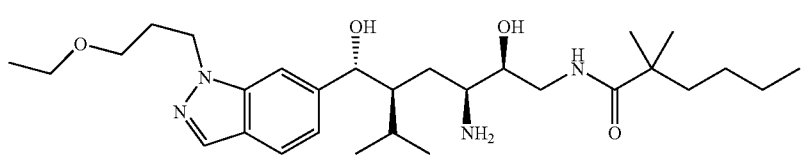

N-((2S,3S,5S)-3-amino-5-((R)-(1-(3-
ethoxypropyl-1H-indazol-6-
yl)(hydroxy)methyl)-2-hydroxy-6-
methylheptyl)-2,2-
dimethylhexanamide I-4b I-5a

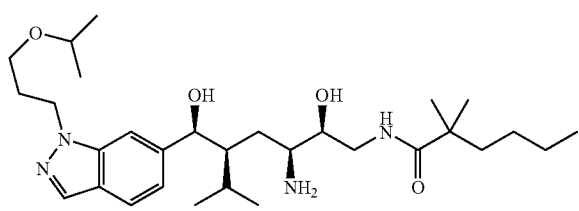

N-((2S,3S,5S)-3-amino-2-hydroxy-
5-((S)-hydroxy(1-(3-
isopropoxypropyl)-1H-indazol-6-
yl)methyl)-6-methylheptyl)-2,2-
dimethylhexanamide I-5b

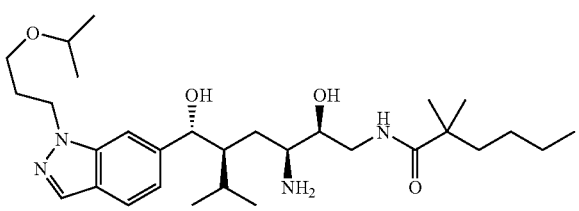

N-((2S,3S,5S)-3-amino-2-hydroxy-
5-((R)-hydroxy(1-(3-
isopropoxypropyl)-1H-indazol-6-
yl)methyl)-6-methylheptyl)-2,2-
dimethylhexanamide I-6a

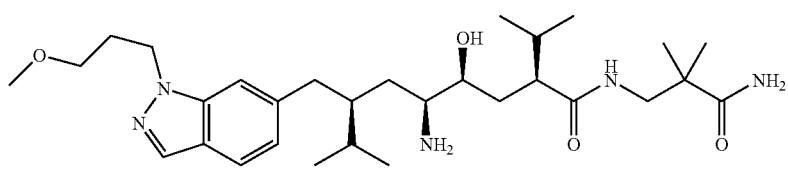

(2S,4S,5S,7S)-5-amino-N-(3-amino-
2,2-dimethyl-3-oxopropyl)-4-
hydroxy-2-isopropyl-7-((1-(3-
methoxypropyl)-1H-indazol-6-
yl)methyl)-8-methylnonanamide I-6b

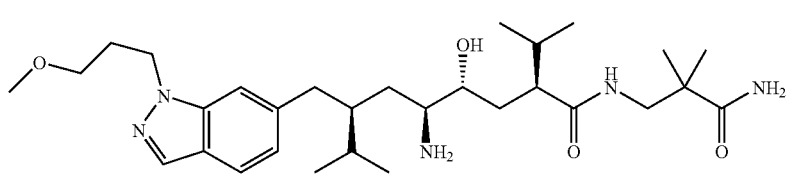

(2S,4R,5S,7S)-5-amino-N-(3-
amino-2,2-dimethyl-3-oxopropyl)-4-
hydroxy-2-isopropyl-7-((1-(3-
methoxypropyl)-1H-indazol-6-
yl)methyl)-8-methylnonanamide -continued

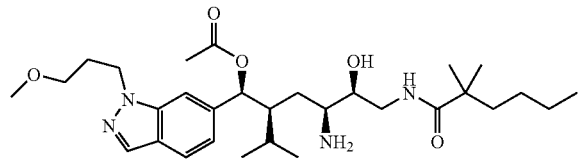

I-7a (1S,2S,4S,5S)-4-amino-6-(2,2-dimethylhexanamido)-5-hydroxy-2-isopropyl-1-(1-(3-methoxypropyl)-1H-indazol-6-yl)hexyl acetate or

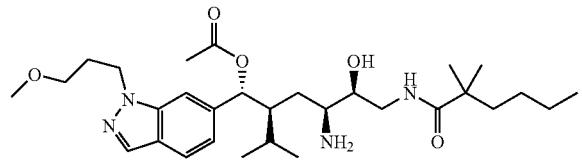

I-7b (1R,2S,4S,5S)-4-amino-6-(2,2-dimethylhexanamido)-5-hydroxy-2-isopropyl-1-(1-(3-methoxypropyl)-1H-indazol-6-yl)hexyl acetate.

or a pharmaceutically acceptable salt thereof.

11. A composition comprising an effective amount of a compound of claim 1, or an enantiomer, diastereomer, or salt thereof, and a pharmaceutically acceptable carrier therefor.

12. A composition of claim 11 further comprising α-blockers, β-blockers, calcium channel blockers, diuretics, natriuretics, saluretics, centrally acting antihypertensives, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, or endothelin receptor antagonists.

13. A composition of claim 11 comprising compounds having a mean inhibition constant ($IC_{50}$) against renin of between about 50,000 nM to about 0.001 nM; preferably between about 100 nM to about 0.001 nM; and more preferably between about 10 nM to about 0.001 nM.

14. A method of inhibiting renin which comprises administering to a subject in need thereof a therapeutically effective amount of a compound of claim 1, or an enantiomer, diastereomer, or salt thereof.

15. A method of claim 14 which comprisies administering compounds having an $IC_{50}$ for renin of between about 50,000 nM to about 0.001 nM; preferably between about 100 nM to about 0.001 nM; and more preferably between about 10 nM to about 0.001 nM.

* * * * *

UNITED STATES PATENT AND TRADEMARK OFFICE
CERTIFICATE OF CORRECTION

| | |
|---|---|
| PATENT NO. | : 8,084,485 B2 |
| APPLICATION NO. | : 12/225756 |
| DATED | : December 27, 2011 |
| INVENTOR(S) | : John J. Baldwin et al. |

It is certified that error appears in the above-identified patent and that said Letters Patent is hereby corrected as shown below:

In Claim 1, column 66, line 41, please delete the extra spaces between the words "N-mono" and "-lower".

In Claim 1, column 66, line 43, please delete the extra spaces between the words "(hydroxy)" and "-lower".

In Claim 1, column 66, line 45, please delete the extra spaces between the words "N" and "-mono".

In Claim 1, column 67, line 12, please delete the extra spaces between the words "haloalkanesulfonyl" and "-cycloalkyl".

In Claim 1, column 67, line 14, please delete the extra spaces between the words "di(lower alkyl)" and "-aminocarbonyl-lower".

In Claim 3, column 67, line 66, please delete the "(C1-C6)" and insert -- (C1-C5) --.

In Claim 3, column 68, line 7, please delete the first "(C1-C6)" and insert -- (C1-C5) --.

In Claim 3, column 68, line 8, please delete the second "(C1-C6)" and insert -- (C1-C5) --.

In Claim 3, column 68, line 15, please delete "1'1".

In Claim 9, column 70, line 20, please delete "I7" and insert -- I-7 --.

In Claim 9, column 70, line 21, please delete the extra spaces between the words "1H" and "indazol-6-yl)".

Signed and Sealed this
Third Day of July, 2012

David J. Kappos
*Director of the United States Patent and Trademark Office*